US006297018B1

(12) United States Patent
French et al.

(10) Patent No.: US 6,297,018 B1
(45) Date of Patent: Oct. 2, 2001

(54) METHODS AND APPARATUS FOR DETECTING NUCLEIC ACID POLYMORPHISMS

(75) Inventors: Todd E. French, Cupertino; Douglas N. Modlin, Palo Alto; John C. Owicki, Palo Alto; James S. Richey, Palo Alto; Lev J. Leytes, Palo Alto; Enal S. Razvi, San Francisco, all of CA (US)

(73) Assignee: LJL BioSystems, Inc., Sunnyvale, CA (US)

( * ) Notice: Subject to any disclaimer, the term of this patent is extended or adjusted under 35 U.S.C. 154(b) by 0 days.

(21) Appl. No.: 09/494,407

(22) Filed: Jan. 28, 2000

Related U.S. Application Data

(63) Continuation-in-part of application No. PCT/US00/00895, filed on Jan. 14, 2000, and a continuation-in-part of application No. 09/468,440, filed on Dec. 21, 1999, and a continuation-in-part of application No. 09/349,733, filed on Jul. 8, 1999, and a continuation-in-part of application No. PCT/US99/08410, filed on Apr. 16, 1999, and a continuation-in-part of application No. PCT/US99/01656, filed on Jan. 25, 1999, and a continuation-in-part of application No. 09/160,533, filed on Sep. 24, 1998, and a continuation-in-part of application No. 09/062,472, filed on Apr. 17, 1998, now Pat. No. 6,071,748.

(60) Provisional application No. 60/124,686, filed on Mar. 16, 1999, provisional application No. 60/125,346, filed on Mar. 19, 1999, provisional application No. 60/135,284, filed on May 21, 1999, and provisional application No. 60/167,463, filed on Nov. 24, 1999.

(51) Int. Cl.$^7$ .............................. C02Q 1/68; C12P 19/34; C07M 21/02

(52) U.S. Cl. ........................... 435/6; 435/91.2; 536/23.1; 536/24.3

(58) Field of Search ...................... 455/6, 912; 536/24.3, 536/23.1

(56) References Cited

U.S. PATENT DOCUMENTS

| | | |
|---|---|---|
| D. 303,149 | 8/1989 | Anderson . |
| 2,056,791 | 10/1936 | Logan . |
| 2,719,214 | 9/1955 | Potter . |
| 3,013,467 | 12/1961 | Minsky . |
| 3,423,581 | 1/1969 | Baer . |
| 3,516,736 | 6/1970 | Weaver . |
| 3,540,858 | 11/1970 | Rochte et al. . |
| 3,849,654 | 11/1974 | Malvin . |
| 3,885,162 | 5/1975 | Geertz . |
| 3,925,162 | 12/1975 | Kanno . |
| 3,932,023 | 1/1976 | Humer . |
| 4,011,451 | 3/1977 | Nelson . |
| 4,053,381 | 10/1977 | Hamblen et al. . |
| 4,067,653 | 1/1978 | Fletcher et al. . |
| 4,074,939 | 2/1978 | Rabl . |
| 4,076,420 | 2/1978 | De Maeyer et al. . |
| 4,100,416 | 7/1978 | Hirschfeld . |
| 4,144,452 | 3/1979 | Harte . |
| 4,150,870 | 4/1979 | d'Auria . |
| 4,203,670 | 5/1980 | Bromberg . |
| 4,240,751 | 12/1980 | Linnecke et al. . |
| 4,245,052 | 1/1981 | Lund . |
| 4,292,273 | 9/1981 | Butz et al. . |
| 4,296,326 | 10/1981 | Haslop et al. . |
| 4,374,120 | 2/1983 | Soini et al. . |
| 4,397,560 | 8/1983 | Andresen . |
| 4,425,427 | 1/1984 | Luderer . |
| 4,451,149 | 5/1984 | Noeller . |
| 4,451,433 | 5/1984 | Yamashita et al. . |
| 4,459,300 | 7/1984 | Kasman . |
| 4,459,360 | 7/1984 | Marinkovich . |
| 4,485,430 | 11/1984 | Achiaga Fustel . |
| 4,490,216 | 12/1984 | McConnell . |
| 4,501,970 | 2/1985 | Nelson . |
| 4,545,958 | 10/1985 | Dopatka . |
| 4,547,527 | 10/1985 | Ingram . |
| 4,567,847 | 2/1986 | Linner . |
| 4,591,550 | 5/1986 | Hafeman et al. . |
| 4,599,315 | 7/1986 | Terasaki et al. . |

(List continued on next page.)

FOREIGN PATENT DOCUMENTS

| | | |
|---|---|---|
| 2099542 | 1/1994 | (CA) . |
| 29805613 U1 | 7/1998 | (DE) . |
| 0 204 109 A2 | 12/1986 | (EP) . |

(List continued on next page.)

OTHER PUBLICATIONS

Pastinen et al, "Multiplex fluorescent solid phase minisequencing for efficient screening of DNA sequence variation", Clin. Chem. 42(9):1391–1397, Sep. 1996.*

*Structural Concepts in Immunology and Immunochemistry*, Kabat, $2^{nd}$ Ed., pp. 103–105, 1976.

*Standard Handbook for Electrical Engineers*, Fink et al., pp. 22–2 through 22–5 ($11^{th}$ ed. 1978).

*Fundamentals of Light Microscopy*, Spencer, Cambridge University Press, 1982.

*Principles of Fluorescence Spectroscopy*, Lakowicz, First Edition, Sep. 1983.

(List continued on next page.)

*Primary Examiner*—Jeffrey Fredman
(74) *Attorney, Agent, or Firm*—Kolisch, Hartwell, Dickinson, McCormack & Heuser

(57) ABSTRACT

Methods and apparatus for detecting polynucleotide hybridization in luminescence-based assays. The methods may include (1) allele-specific hybridization, using luminescence detection, (2) allele-specific oligonucleotide ligation, using dye-labeled oligonucleotide ligation with luminescence resonance energy transfer (FRET) detection, and (3) allele-specific nucleotide incorporation, using primer extension with luminescence polarization (FP) detection. More specifically, the methods may include (1) locating a sample containing a nucleic acid material at an examination site, (2) illuminating the sample, (3) detecting light transmitted from the sample, and (4) determining the presence, absence, and/or identity of a nucleic acid target in the sample using the light transmitted from the sample.

12 Claims, 23 Drawing Sheets

U.S. PATENT DOCUMENTS

| | | |
|---|---|---|
| 4,622,208 | 11/1986 | Namba et al. . |
| 4,626,684 | 12/1986 | Landa . |
| 4,646,214 | 2/1987 | Mendleski . |
| 4,656,127 | 4/1987 | Mundy . |
| 4,685,801 | 8/1987 | Minekane . |
| 4,699,512 | 10/1987 | Koshi . |
| 4,699,978 | 10/1987 | Barton . |
| 4,704,255 | 11/1987 | Jolley . |
| 4,704,353 | 11/1987 | Humphries et al. . |
| 4,707,067 | 11/1987 | Haberland et al. . |
| 4,707,440 | 11/1987 | Stavrianopoulos . |
| 4,721,669 | 1/1988 | Barton . |
| 4,730,921 | 3/1988 | Klein et al. . |
| 4,735,778 | 4/1988 | Maruyama et al. . |
| 4,737,464 | 4/1988 | McConnell et al. . |
| 4,738,825 | 4/1988 | Kelln et al. . |
| 4,741,619 | 5/1988 | Humphries et al. . |
| 4,753,501 | 6/1988 | Battle . |
| 4,758,786 | 7/1988 | Hafeman . |
| 4,762,420 | 8/1988 | Bowley . |
| 4,772,453 | 9/1988 | Lisenbee . |
| 4,784,275 | 11/1988 | Fridge . |
| 4,801,804 | 1/1989 | Rosenthal . |
| 4,802,768 | 2/1989 | Gifford et al. . |
| 4,808,828 | 2/1989 | Kitamori et al. . |
| 4,810,096 | 3/1989 | Russell et al. . |
| 4,822,733 | 4/1989 | Morrison . |
| 4,826,660 | 5/1989 | Smith et al. . |
| 4,849,330 | 7/1989 | Humphries et al. . |
| 4,851,331 | 7/1989 | Vary et al. . |
| 4,855,930 | 8/1989 | Chao et al. . |
| 4,863,849 | 9/1989 | Melamede . |
| 4,868,103 | 9/1989 | Stavrianopoulos et al. . |
| 4,873,633 | 10/1989 | Mezei et al. . |
| 4,877,965 | 10/1989 | Dandliker et al. . |
| 4,883,579 | 11/1989 | Humphries et al. . |
| 4,885,087 | 12/1989 | Kopf . |
| 4,892,409 | 1/1990 | Smith . |
| 4,897,548 | 1/1990 | Döme et al. . |
| 4,911,794 | 3/1990 | Parce et al. . |
| 4,915,812 | 4/1990 | Parce et al. . |
| 4,923,819 | 5/1990 | Fernandez et al. . |
| 4,931,402 | 6/1990 | Abplanalp . |
| 4,936,682 | 6/1990 | Hoyt . |
| 4,942,127 | 7/1990 | Wada et al. . |
| 4,948,442 | 8/1990 | Manns . |
| 4,956,275 | 9/1990 | Zuk et al. . |
| 4,962,020 | 10/1990 | Tabor et al. . |
| 4,963,658 | 10/1990 | Kung et al. . |
| 4,963,815 | 10/1990 | Hafeman . |
| 4,968,148 | 11/1990 | Chow et al. . |
| 4,978,608 | 12/1990 | Kung et al. . |
| 4,979,093 | 12/1990 | Laine et al. . |
| 4,979,821 | 12/1990 | Schutt et al. . |
| 5,004,806 | 4/1991 | Kung . |
| 5,009,488 | 4/1991 | Fay et al. . |
| 5,011,770 | 4/1991 | Kung et al. . |
| 5,018,866 | 5/1991 | Osten . |
| 5,020,995 | 6/1991 | Levy . |
| 5,034,613 | 7/1991 | Denk et al. . |
| 5,039,219 | 8/1991 | James et al. . |
| 5,047,215 | 9/1991 | Manns . |
| 5,058,045 | 10/1991 | Ma . |
| 5,082,628 | 1/1992 | Andreotti et al. . |
| 5,084,246 | 1/1992 | Lyman et al. . |
| 5,091,652 | 2/1992 | Mathies et al. . |
| 5,095,517 | 3/1992 | Monguzzi et al. . |
| 5,096,807 | 3/1992 | Leaback . |
| 5,104,804 | 4/1992 | Humphries et al. . |
| 5,110,556 | 5/1992 | Lyman et al. . |
| 5,112,134 | 5/1992 | Chow et al. . |
| 5,160,702 | 11/1992 | Kopf-Sill et al. . |
| 5,164,319 | 11/1992 | Hafeman et al. . |
| 5,169,601 | 12/1992 | Ohta et al. . |
| 5,192,510 | 3/1993 | Zoha et al. . |
| 5,196,709 | 3/1993 | Berndt et al. . |
| 5,198,670 | 3/1993 | VanCauter et al. . |
| 5,206,568 | 4/1993 | Björnson et al. . |
| 5,208,161 | 5/1993 | Saunders et al. . |
| 5,208,651 | 5/1993 | Buican . |
| 5,216,488 | 6/1993 | Tuunanen et al. . |
| 5,225,164 | 7/1993 | Astle . |
| 5,225,543 | 7/1993 | Eppler et al. . |
| 5,232,858 | 8/1993 | Wolfbeis et al. . |
| 5,246,867 | 9/1993 | Lakowicz et al. . |
| 5,252,293 | 10/1993 | Drbal et al. . |
| 5,256,535 | 10/1993 | Ylikoski et al. . |
| 5,257,202 | 10/1993 | Fedderson et al. . |
| 5,262,128 | 11/1993 | Leighton et al. . |
| 5,270,788 | 12/1993 | Cercek et al. . |
| 5,273,718 | 12/1993 | Skold et al. . |
| 5,275,951 | 1/1994 | Chow et al. . |
| 5,278,048 | 1/1994 | Parce et al. . |
| 5,279,943 | 1/1994 | Mathis et al. . |
| 5,281,825 | 1/1994 | Berndt et al. . |
| 5,283,173 | 2/1994 | Fields et al. . |
| 5,289,407 | 2/1994 | Strickler et al. . |
| 5,302,509 | 4/1994 | Cheeseman . |
| 5,307,144 | 4/1994 | Hiroshi et al. . |
| 5,315,015 | 5/1994 | Hui et al. . |
| 5,317,485 | 5/1994 | Merjanian . |
| 5,319,436 | 6/1994 | Manns et al. . |
| 5,323,008 | 6/1994 | Studholme et al. . |
| 5,323,010 | 6/1994 | Gratton et al. . |
| 5,334,353 | 8/1994 | Blattner . |
| 5,340,716 | 8/1994 | Ullman et al. . |
| 5,340,747 | 8/1994 | Eden . |
| 5,341,215 | 8/1994 | Seher . |
| 5,349,436 | 9/1994 | Fisch . |
| 5,353,112 | 10/1994 | Smith . |
| 5,355,215 | 10/1994 | Schroeder et al. . |
| 5,357,095 | 10/1994 | Weyrauch et al. . |
| 5,361,626 | 11/1994 | Colligan et al. . |
| 5,384,093 | 1/1995 | Ootani et al. . |
| 5,395,503 | 3/1995 | Parce et al. . |
| 5,401,465 | 3/1995 | Smethers et al. . |
| 5,409,666 | 4/1995 | Nagel et al. . |
| 5,409,835 | 4/1995 | Lakowicz et al. . |
| 5,418,371 | 5/1995 | Aslund et al. . |
| 5,420,408 | 5/1995 | Weyrauch et al. . |
| 5,436,718 | 7/1995 | Fernandes et al. . |
| 5,443,791 | 8/1995 | Cathcart et al. . |
| 5,445,935 | 8/1995 | Royer . |
| 5,449,921 | 9/1995 | Baba . |
| 5,457,527 | 10/1995 | Manns et al. . |
| 5,480,804 | 1/1996 | Niwa et al. . |
| 5,485,530 | 1/1996 | Lakowicz et al. . |
| 5,487,872 | 1/1996 | Hafeman et al. . |
| 5,491,343 | 2/1996 | Brooker . |
| 5,496,697 | 3/1996 | Parce et al. . |
| 5,497,670 | 3/1996 | Carl . |
| 5,500,188 | 3/1996 | Hafeman et al. . |
| 5,501,956 | 3/1996 | Wada et al. . |
| 5,504,337 | 4/1996 | Lakowicz et al. . |
| 5,512,492 | 4/1996 | Herron et al. . |
| 5,516,490 | 5/1996 | Sanadi . |
| 5,518,900 | 5/1996 | Nikiforov et al. . |
| 5,523,573 | 6/1996 | Hänninen et al. . |
| 5,525,479 | 6/1996 | Anthony et al. . |
| 5,527,684 | 6/1996 | Mabile et al. . |
| 5,527,688 | 6/1996 | Mallia . |

| | | | | | | |
|---|---|---|---|---|---|---|
| 5,528,046 | 6/1996 | Ishikawa . | | 5,772,966 | 6/1998 | Maracas et al. . |
| 5,529,752 | 6/1996 | Pontis et al. . | | 5,772,967 | 6/1998 | Wannlund et al. . |
| 5,531,697 | 7/1996 | Olsen et al. . | | 5,773,257 | 6/1998 | Nielson et al. . |
| 5,531,698 | 7/1996 | Olsen . | | 5,780,857 | 7/1998 | Harju et al. . |
| 5,536,662 | 7/1996 | Humphries et al. . | | 5,786,139 | 7/1998 | Burke et al. . |
| 5,537,343 | 7/1996 | Kikinis et al. . | | 5,798,035 | 8/1998 | Kirk et al. . |
| 5,540,889 | 7/1996 | Gordon et al. . | | 5,798,083 | 8/1998 | Massey et al. . |
| 5,541,113 | 7/1996 | Siddigi et al. . | | 5,798,085 | 8/1998 | Seaton et al. . |
| 5,542,012 | 7/1996 | Fernandes et al. . | | 5,800,778 | 9/1998 | Chen et al. . |
| 5,557,398 | 9/1996 | Wechsler et al. . | | 5,800,989 | 9/1998 | Linn et al. . |
| 5,560,811 | 10/1996 | Briggs et al. . | | 5,801,055 | 9/1998 | Henderson . |
| 5,561,051 | 10/1996 | Silverman . | | 5,811,256 | 9/1998 | Bryant . |
| 5,561,068 | 10/1996 | Rounbehler et al. . | | 5,820,849 | 10/1998 | Schmitt-Willich et al. . |
| 5,567,302 | 10/1996 | Song et al. . | | 5,824,557 | 10/1998 | Burke et al. . |
| 5,571,684 | 11/1996 | Lawrence et al. . | | 5,824,772 | 10/1998 | Vincent et al. . |
| 5,589,136 | 12/1996 | Northrup et al. . | | 5,825,617 | 10/1998 | Kochis et al. . |
| 5,589,350 | 12/1996 | Bochner . | | 5,827,653 | 10/1998 | Sammes et al. . |
| 5,589,351 | 12/1996 | Harootunian . | | 5,840,256 | 11/1998 | Demers et al. . |
| 5,592,289 | 1/1997 | Norris . | | 5,842,582 | 12/1998 | DeStefano, Jr. . |
| 5,593,867 | 1/1997 | Walker et al. . | | 5,846,710 | 12/1998 | Bajaj . |
| 5,595,710 | 1/1997 | Van Dusen et al. . | | 5,846,722 | 12/1998 | Kauvar et al. . |
| 5,599,500 | 2/1997 | Jones . | | 5,849,547 | 12/1998 | Cleuziat et al. . |
| 5,599,681 | 2/1997 | Epstein et al. . | | 5,853,894 | 12/1998 | Brown . |
| 5,604,130 | 2/1997 | Warner et al. . | | 5,858,309 | 1/1999 | Mathus . |
| 5,610,075 | 3/1997 | Stahl-Rees . | | 5,858,671 | 1/1999 | Jones . |
| 5,610,287 | 3/1997 | Nikiforov et al. . | | 5,861,239 | 1/1999 | Kleyn et al. . |
| 5,620,894 | 4/1997 | Barger et al. . | | 5,873,394 | 2/1999 | Meltzer . |
| 5,622,821 | 4/1997 | Selvin et al. . | | 5,874,214 | 2/1999 | Nova et al. . |
| 5,624,847 | 4/1997 | Lakowicz et al. . | | 5,879,632 | 3/1999 | Demers . |
| 5,626,134 | 5/1997 | Zuckerman . | | 5,880,096 | 3/1999 | Barrett et al. . |
| 5,631,127 | 5/1997 | Sundrehagen . | | 5,880,296 | 3/1999 | Imbert et al. . |
| 5,631,169 | 5/1997 | Lakowicz et al. . | | 5,882,597 | 3/1999 | Astle . |
| 5,631,734 | 5/1997 | Stern et al. . | | 5,882,930 | 3/1999 | Baier . |
| 5,632,982 | 5/1997 | Sussman et al. . | | 5,885,779 | 3/1999 | Sadowski et al. . |
| 5,633,724 | 5/1997 | King et al. . | | 5,888,454 | 3/1999 | Leistner et al. . |
| 5,635,402 | 6/1997 | Alfano et al. . | | 5,888,728 | 3/1999 | Olson et al. . |
| 5,637,463 | 6/1997 | Dalton et al. . | | 5,888,819 | 3/1999 | Goelet et al. . |
| 5,639,615 | 6/1997 | Selvin et al. . | | 5,891,621 | 4/1999 | Chabin et al. . |
| 5,641,633 | 6/1997 | Linn et al. . | | 5,891,674 | 4/1999 | Hillman et al. . |
| 5,645,800 | 7/1997 | Masterson et al. . | | 5,891,696 | 4/1999 | Shaw et al. . |
| 5,648,269 | 7/1997 | Lakowicz et al. . | | 5,905,571 | 5/1999 | Butler et al. . |
| 5,650,125 | 7/1997 | Bosanquet . | | 5,910,287 | 6/1999 | Cassin et al. . |
| 5,660,991 | 8/1997 | Lakowicz et al. . | | 5,910,574 | 6/1999 | Presta et al. . |
| 5,663,545 | 9/1997 | Marquiss . | | 5,912,137 | 6/1999 | Tsien et al. . |
| 5,668,110 | 9/1997 | Barrett et al. . | | 5,914,230 | 6/1999 | Liu et al. . |
| 5,670,113 | 9/1997 | Akong et al. . | | 5,933,232 | 8/1999 | Atzler et al. . |
| 5,671,880 | 9/1997 | Kain . | | 5,945,283 | 8/1999 | Kwok et al. . |
| 5,676,943 | 10/1997 | Baetge et al. . | | 5,948,620 | 9/1999 | Hurd et al. . |
| 5,677,196 | 10/1997 | Herron et al. . | | 5,958,694 | 9/1999 | Nikiforov . |
| 5,677,280 | 10/1997 | Barrett et al. . | | 5,959,738 | 9/1999 | Hafeman et al. . |
| 5,679,310 | 10/1997 | Manns . | | 5,961,926 | 10/1999 | Kolb et al. . |
| 5,683,983 | 11/1997 | Barrett et al. . | | 5,962,243 | 10/1999 | Brown et al. . |
| 5,705,045 | 1/1998 | Park et al. . | | 5,981,180 | 11/1999 | Chandler et al. . |
| 5,707,813 | 1/1998 | Dandliker et al. . | | 5,981,185 | 11/1999 | Matson et al. . |
| 5,723,304 | 3/1998 | Abuknesha . | | 5,989,835 * | 11/1999 | Dunlay et al. .......................... 435/7.2 |
| 5,736,410 | 4/1998 | Zarling et al. . | | 5,993,746 | 11/1999 | Priha et al. . |
| 5,738,825 | 4/1998 | Rudigier et al. . | | 6,004,744 | 12/1999 | Goelet et al. . |
| 5,741,554 | 4/1998 | Tisone . | | 6,013,431 | 1/2000 | Söderlund et al. . |
| 5,741,714 | 4/1998 | Liberti . | | 6,013,457 | 1/2000 | Neuenhofer et al. . |
| 5,744,320 | 4/1998 | Sherf et al. . | | 6,018,388 | 1/2000 | Nawracala et al. . |
| 5,746,974 | 5/1998 | Massey et al. . | | 6,020,591 | 2/2000 | Harter et al. . |
| 5,750,410 | 5/1998 | Dou et al. . | | 6,025,129 | 2/2000 | Nova et al. . |
| 5,756,050 | 5/1998 | Ershow et al. . | | 6,025,985 | 2/2000 | Leytes et al. . |
| 5,756,292 * | 5/1998 | Royer ........................................ 435/6 | | 6,027,695 | 2/2000 | Oldenburg et al. . |
| 5,756,304 | 5/1998 | Jovanovich . | | 6,033,100 | 3/2000 | Marquiss et al. . |
| 5,759,494 | 6/1998 | Szlosek . | | 6,033,605 | 3/2000 | Szlosek . |
| 5,760,188 | 6/1998 | Beaudet et al. . | | 6,037,136 | 3/2000 | Beach et al. . |
| 5,763,158 | 6/1998 | Bohannon . | | 6,045,755 | 4/2000 | Lebl et al. . |
| 5,766,875 | 6/1998 | Hafeman et al. . | | 6,045,996 | 4/2000 | Cronin et al. . |
| 5,770,151 | 6/1998 | Roach et al. . | | 6,054,557 | 4/2000 | Faure et al. . |
| 5,770,455 | 6/1998 | Cargill et al. . | | 6,071,748 * | 6/2000 | Modlin et al. .......................... 436/174 |

FOREIGN PATENT DOCUMENTS

| | | |
|---|---|---|
| 0 222 341 A1 | 5/1987 | (EP) . |
| 0 266 881 A2 | 5/1988 | (EP) . |
| 0 259 386 B1 | 4/1991 | (EP) . |
| 0 542 422 A1 | 5/1993 | (EP) . |
| 0 578 067 A1 | 1/1994 | (EP) . |
| 0 317 074 B1 | 12/1996 | (EP) . |
| 0 382 433 B1 | 11/1997 | (EP) . |
| 0 648 280 B1 | 5/1999 | (EP) . |
| 0 977 037 A1 | 2/2000 | (EP) . |
| 0 993 916 A2 | 4/2000 | (EP) . |
| 0 995 555 A1 | 4/2000 | (EP) . |
| 1 003 020 A1 | 5/2000 | (EP) . |
| 1 003 039 A1 | 5/2000 | (EP) . |
| 2 215 838 A | 9/1989 | (GB) . |
| 2 228 081 A | 8/1990 | (GB) . |
| WO97/45739 | 12/1947 | (WO) . |
| WO91/13075 | 9/1991 | (WO) . |
| WO92/11039 | 7/1992 | (WO) . |
| WO92/15712 | 9/1992 | (WO) . |
| WO93/19206 | 9/1993 | (WO) . |
| WO94/29024 | 12/1994 | (WO) . |
| WO95/12607 | 5/1995 | (WO) . |
| WO95/21271 | 8/1995 | (WO) . |
| WO97/22719 | 6/1997 | (WO) . |
| WO97/35033 | 9/1997 | (WO) . |
| WO98/05962 | 2/1998 | (WO) . |
| WO98/18956 | 5/1998 | (WO) . |
| WO98/46981 | 10/1998 | (WO) . |
| WO98/59066 | 12/1998 | (WO) . |
| WO99/04228 | 1/1999 | (WO) . |
| WO99/08233 | 2/1999 | (WO) . |
| WO99/11774 | 3/1999 | (WO) . |
| WO99/23466 | 5/1999 | (WO) . |
| WO99/29894 | 6/1999 | (WO) . |
| WO99/31431 | 6/1999 | (WO) . |
| WO99/37203 | 7/1999 | (WO) . |
| WO99/42817 | 8/1999 | (WO) . |
| WO99/54711 | 10/1999 | (WO) . |
| WO99/60383 | 11/1999 | (WO) . |
| WO00/00819 | 1/2000 | (WO) . |
| WO00/04364 | 1/2000 | (WO) . |
| WO00/11220 | 3/2000 | (WO) . |
| WO00/47693 | 8/2000 | (WO) . |
| WO00/48990 | 8/2000 | (WO) . |
| WO00/48991 | 8/2000 | (WO) . |
| WO00/50877 | 8/2000 | (WO) . |
| WO00/55372 | 9/2000 | (WO) . |
| WO00/66269 | 11/2000 | (WO) . |

OTHER PUBLICATIONS

A System for Rapid DNA Sequencing with Fluorescent Chain–Terminating Dideoxynucleotides, Prober et al., *Science*, pp. 336–341, Oct. 16, 1987.

Time–Resolved Fluorescence of Lanthanide Probes and Applications in Biotechnology, Soini et al, *CRC Critical Reviews in Analytical Chemistry*, vol. 18, No. 2, 1987.

Solid Phase DNA Sequencing Using the Biotin–Avidin System, Stahl et al., *Nucleic Acids Res.*, vol. 16, No. 7, pp. 3025–3038, Apr. 11, 1988 (abstract only).

Synthetic Peptide Analogues Differentially Alter the Binding Affinities of Cyclic Nucleotide Dependent Protein Kinases for Nucleotide Substrates, Bhatnagar et al., *Biochemistry*, vol. 27, No. 6, pp. 1988–1994, 1988.

Stratagene 1988 Catalog excerpt, 1988.

Direct Solid Phase Sequencing of genomic and Plasmid DNA Using Magnetic Beads as Solid Support, Hultman et al., *Nucleic Acids Res.*, vol. 17, No. 13, pp. 4937–4946, Jul. 11, 1989 (abstract only).

Basic Fluorescence Microscopy, Taylor et al., *Methods in Cell Biology*, vol. 29, pp. 207–237, 1989.

Quantitative Fluorescence Microscopy Using Photomultiplier Tubes and Imaging Detectors, Wampler et al., *Methods in Cell Biology*, vol. 29, pp. 239–267, 1989.

Three–Dimensional Confocal Fluorescence Microscopy, Brakenhoff et al., *Methods in Cell Biology*, vol. 30, pp. 379–389, 1989.

RNA Sequencing Using Fluorescent–Labeled Dideoxynucleotides and Automated Fluorescence Detection, Bauer, *Nucleic Acids Res.*, vol. 18, No. 4, pp. 879–884, Feb. 25, 1990 (abstract only).

The Unusual Origin of the Polymerase Chain Reaction, Mullis, *Scientific American*, pp. 56–65, Apr. 1990.

A Primer–Guided Nucleotide Incorporation Assay in the Genotyping of Apolipoprotein E, Syvanen et al., *Genomics*, vol. 8, No. 4, pp. 684–692, Dec. 1990 (abstract only).

A Brief Survey of Methods for Preparing Protein Conjugates with Dyes, Haptens, and Cross–Linking Reagents, Brinkley, *Bioconjugate Chemistry*, vol. 3, No. 1, pp. 59–70, Jan./Feb. 1992.

Trapped–Oligonucleotide Nucleotide Incorporation (TONI) Assay, A Simple Method for Screening Point Mutations, Prezant et al., *Hum. Mutat.*, vol. 1, No. 2, pp. 159–164, 1992 (abstract only).

Laser Scanning Confocal Microscopy of Living Cells, Lemasters et al., *Optical Microscopy: Emerging Methods and Applications*, pp. 339–345, 1993.

Time–Resolved Fluorescence Lifetime Imaging, vande Ven et al., *Optical Microscopy: Emerging Methods and Applications*, pp. 373–389, 1993.

Time–Resolved Fluorescence of a New Europium Chelate Complex: Demonstration of Highly Sensitive Detection of Protein and DNA Samples, Saha et al., *J. Am. Chem. Soc.*, vol. 115, No. 23, pp. 11032–11033, 1993.

Luminescent Lanthanide Complexes as Photochemical Supramolecular Devices, Sabbatini et al., *Coordination Chemistry Reviews*, vol. 123, pp. 201–228, 1993.

Electrochemiluminescence: A New Diagnostic and Research Tool, Yang et al., *Bio/Technology*, vol. 12, pp. 193–194, Feb. 1994.

Processing of cDNA and Genomic Kilobase–Size Clones for Massive Screening, Mapping and Sequencing by Hybridization, Drmanac et al., *BioTechniques*, vol. 17, No. 2, pp. 328–336, 1994.

High Throughput Screening Using Dynamic Fluorescence, Swift et al., *SPIE*, vol. 2388, pp. 182–189, Feb. 6–8, 1995.

Fluorescence–Based DNA Minisequence Analysis for Detection of Known Single–Base Changes in Genomic DNA, Kobayashi et al., *Mol. Cell. Probes*, vol. 9, No. 3, pp. 175–182, Jun. 1995 (abstract only).

Hybridization of Fluorescein–Labeled DNA Oligomers Detected by Fluorescence Anisotropy with Protein Binding Enhancement, Kumke et al., *Anal. Chem.* vol. 67, No. 21, pp. 3945–3951, Nov. 1, 1995.

A Lifetime–Based Optical $CO_2$ Gas Sensor with Blue or Red Excitation and Stokes or Anti–Stokes Detection, Sipior et al., *Anal. Chem.*, 227, pp. 309–318, 1995.

Time Resolved Detection of Lanthanide Luminescence for Ultrasensitive Bioanalytical Assays, Dickson et al., *J. Photochem. Photobiol. B. Biol.,* vol. 27, pp. 3–19, 1995.

Fluorescence Energy Transfer Immunoassay Based on a Long–Lifetime Luminescent Metal–Ligand Complex, Young et al., *Analytical Biochemistry,* vol. 232, pp. 24–30, 1995.

PCR Reaction Vessels brochure, Corning Costar Corporation, Sep. 1996.

Gene Genie, Burke, *The Red Herring,* internet pp 1–7, Dec. 1996.

Comparative Study of Fluorescent Ternary Terbium Complexes. Application in Enzyme Amplified Fluorimetric Immunoassay for a–fetoprotein, Veiopoulou et al., *Analytica Chimica Acta,* vol. 335, pp. 177–184, 1996.

Chemical Abstracts No. 124:160,011; abstract for Lindstroem et al., Electron transport properties in dye–sensitized nanocrystallin/nanostructured titanium dioxide films: J. Phys. Chem. vol. 100 (8), pp. 3084–3088, 1996.

Gene Chip Breakthrough, Stipp, *Fortune,* internet pp. 1–12, Mar. 31, 1997.

Miniprep 50 Mini Sample Processor brochure, Tecan AG, Jun. 1997.

Advanced Microplate Washers brochure, Tecan AG, Jul. 1997.

Genesis Series Robotic Sample Processors brochure, Tecan AG, Oct. 1997.

Genesis Robotic Microplate Procesor brochure, Tecan AG, Nov. 1997.

Miniprep 75 Robotic Sample Processor brochure, Tecan AG, Nov. 1997.

Electrochemiluminescence: A Technology Review internet pages, IGEN, printed Dec. 16, 1997.

The Society for Biomolecular Screening, $3^{rd}$ Annual Conference and Exhibition, p. 59, Sep. 9, 22–25, 1997.

A Homogeneous Method for Genotyping with Fluorescence Polarization, Gibson et al., *Clinical Chemistry,* vol. 43, No. 8, pp. 1336–1341, 1997.

Template–Directed Dye–Terminator Incorporation (TDI) Assay: A Homogeneous DNA Diagnostic Method Based on Fluorescence Resonance Energy Transfer, Chen et al., *Nucleic Acids Research,* vol. 25, No. 2, pp. 347–353, 1997.

Minisequencing: A Specific Tool for DNA Analysis and Diagnostics on Oligonucleotide Arrays, Pastinen et al., *genome Research,* vol. 7, pp. 606–614, 1997.

Towards Materials with Planned Properties: Dinuclear f–f Helicates and d–f Non–Covalent Podates Based on Benzimidazole–Pyridine Binding Units, Bunzli et al., *Journal of Alloys and Compounds,* vol., 249, pp. 14–24, 1997.

Development of Luminescent Lanthanide Chelate Labels for Diagnostic Assays, Hemmila et al., *Journal of Alloys and Compounds,* vol. 249, pp. 158–162, 1997.

Water–Soluble Neutral calyx[4]arene–Lanthanide Complexes: Synthesis and Luminescence Properties, Steemers et al., *J. Org. Chem.,* vol. 62, pp. 4229–4235, 1997.

A Measure of brilliance, TR717 Microplate Luminometer brochure, Tropix, Inc., 1997.

Chemical Abstracts No. 126:72,240; abstract for Hermann et al., "Structure of Nanocrystalline $TiO_2$ Powders and Precursor to Their Highly Efficient Photosensitizer," Chem. Mater., vol. 9 (2), pp. 430–439, 1997.

Fluorescence Polarization Applications Guide, Pan Vera Corporation, pp. 6–1 through 6–4, Jan. 1998 Edition.

Advanced Microplate Detection systems brochure, Tecan AG, Feb. 1998.

The SPECTRA Family brochure, Tecan AG, Feb. 1998.

GeneChip Probe Array Synthesis, Affymetrix, internet pp. 1–2, Mar. 17, 1998.

Assist Plate Handling Device brochure, Labsystems, May 1998.

Wallac Time–Resolved Fluorometry–The Key to Improved Assay Sensitivity, internet description pp., Jul. 7, 1998.

Wallac Labeling Reagents for time–Resolved Fluorometry, internet description page, Jul. 7, 1998.

Wallac 1234 DELFIA Fluorometer, internet description page, Jul. 7, 1998.

Wallac 1420 VICTOR Multilabel Counter, internet description pages, Jul. 7, 1998.

Wallac 1420 VICTOR$^2$ Multilabel Counter, internet description pages, Jul. 7, 1998.

Wallac 1442 ARTHUR Multi–Wavelength Fluoroimager, internet description page, Jul. 7, 1998.

Genesis Assay Workstation brochure, Tecan AG, Jul. 1998.

Genesis Logistics Workstation brochure, Tecan AG, Jul. 1998.

Mutation Detection and Single–Molecule Counting Using Isothermal Rolling–Circle Amplification, Lizardi et al., *Nature Genetics,* vol. 19, No. 3, pp. 225–232, Jul. 1998.

Homogeneous Time–Resolved IL–2–IL–2Ra Assay Using Fluorescence Resonance Energy Transfer, Stenroos et al., *Cytokine,* vol. 10, No. 7, pp. 495–499, Jul. 1998.

Polarion brochure, Tecan AG, Aug. 1998.

Illuminating the SNP Genomic Code, Czarnik, *Modern Drug Discovery,* pp. 49–55, Nov./Dec. 1998.

A Catalog of Reagents, Microplates and Accessories of Life Science Research, Book 2, Packard BioScience Company, Dec. 1998.

Fixed Polarizer Ellipsometry for Simple and Sensitive Detection of Thin Films Generated by Specific Molecular Interactions: Applications in Immunoassays and DNA Sequence Detection, Ostroff et al., *Clinical Chemistry,* vol. 44, No. 9, pp. 2031–2035, 1998.

CytoFluor Fluorescence Multi–Well Plate Reader brochure, PerSeptive Biosystems, 1998.

Setting the Standard, the HTS Compatibility Program brochure, Corning Incorporated, 1998.

Microplate Instrumentation Catalogue 1998, Labsystems, 1998.

Luc–Screen brochure, Tropix, Inc., 1998.

Xpress–Screen brochure, Tropix, Inc., 1998.

Nunc Products 1998–1999 Catalog, Nalge Nunc International, 1998.

The Human Genome Project: Challenges and Opportunities, Washington University in St. Louis, Mar. 5, 1999.

Advanced Microplate Washers, Tecan AG, Apr. 1999.

Everything's Great When it Sits on a Chip, Sinclair, *The Scientist,* vol. 13, No. 11, May 24, 1999.

Assay Miniaturization for High–Throughput Screening, Panfili, Sep. 1999.

Pan Vera Postings, Issue 5, Pan Vera Corporation, Oct. 1999.

CyBi™–Disk brochure, CyBio AG, Oct. 1999.

SnaPshot ddNTP Primer Extension Kit product bulletin, PE Biosystems, Oct. 1999.

Handout Information, Tips and Tricks . . . Automated Liquid–Handling in the Microplate Format, CyBio AG, Nov. 1999.

TWISTER™, Tecan's Automated Microplate Handler brochure, Tecan AG, Nov. 1999.

Magellan, Instrument Control and Data Analysis Software brochure, Tecan AG, Nov. 1999.

Absorbance Readers brochure, Tecan AG, Dec. 1999.

ULTRA—The Solution for HTS and Assay Development brochure, Tecan Austria GmbH, Dec. 1999.

Kinase Assay Based on Thiophosphorylation and Biotinylation, Jeong et al., *BioTechniques,* vol. 27, pp. 1232–1238, Dec. 1999.

Terbium and Rhodamine as Labels in a Homogeneous Time–Resolved Fluorometric Energy Transfer Assay of the β Subunit of Human Chorionic Gonadotropin in Serum, Blomberg et al., *Clinical Chemistry,* vol. 45, No. 6, pp. 855–861, 1999.

Mono(di)nuclear Europium(III) Complexes of Macrobi (tri)cyclic Cryptands Derived from Diazatetralactams as Luminophores in Aqueous Solution, Galaup et al., *Helvetica Chimica Acta,* vol. 82, pp. 543–560, 1999.

Synthesis, Time–Resolved Luminescence, NMR Spectroscopy, Circular Dichroism and Circularly Polarised Luminescence Studies of Enantiopure Macrocyclic Lanthanide Tetraamide Complexes, Dickins et al., *Chem. Eur. J.,* vol. 5, No. 3, 1999.

Fluorescence Polarization in Homogeneous Nucleic Acid Analysis, Chen et al., *Genome Research,* vol. 9, pp. 492–498, 1999.

Principles of Fluorescence Spectroscopy, Lakowicz, Second Edition, 1999.

New Fluorescent Labels for Polarization Assays and Lifetime Imaging, Analytix, Feb. 2000.

CyBi™–PlateSafe brochure, CyBio AG, May 2000.

CyBi™–Lumax 1,536 brochure, CyBio AG, May 2000.

CyBi™–Well 2000 brochure, CyBio AG, May 2000.

Packard BioScience Company Introduces the Fusion™ Universal Microplate Analyzer press release, Packard BioScience Company, Jun. 29, 2000.

SPECTRAmax® GEMINI XS brochure, Molecular Devices Corp., Jun. 2000.

SPECTRAmax® PLUS[384] brochure, Molecular Devices Corp., Jun. 2000.

Tris(2,2'bipyridyl)ruthenium(II) internet pages, OMLC, printed Jul. 3, 2000.

Protein Tyrosine Kinase Assay Kits flyer, Pan Vera Corporation, Jul. 2000.

Protein Kinase C Assay Kits flyer, Pan Vera Corporation, Jul. 2000.

CoreHTS, Estrogen Receptor –α& –β Competitor Assays brochure, Pan Vera Corporation, Jul. 2000.

Fusion™, Universal Microplate Analyzer, Parkard BioScience Company, Aug. 2000.

Labcyte: Research and Clinical Instruments for Life Sciences brochure, Arlena Research LLC, Aug. 1, 2000.

ProxiPlate internet description page, Packard BioScience Company, printed Sep. 17, 2000.

Approaching the 2 μL to 10 μL Range: 384 Well Small Volume vs. 1536 Well Plates poster, Greiner Labortechnik, Sep. 2000.

CyBi™–Screen–Machine: One System–Many Solutions brochure, CyBio AG, 2000.

Development of High Throughput Screening Assays Using Fluorescence Polarization: Nuclear Receptor–Ligand–Binding and Kinase/Phosphatase Assays, Parker et al., *Journal of Biomolecular Screening,* vol. 5, No. 2, 2000.

Reacti–Bind™ Metal Chelate High Binding Capacity Plates flyer, Pierce Chemical Company, 2000.

Reacti–Bind™ Metal Chelate Plates flyer, Pierce Chemical Company, 2000.

Reacti–Bind™ NeutrAvidin™ High Binding Capacity (HBC) Coated Plates flyer, Pierce Chemical Company, 2000.

Reacti–Bind™ NeutrAvidin™ and Streptavidin Coated Plates flyer, Pierce Chemical Company, 2000.

Nunc Life Science Discovery Products catalog, Nalge Nunc International Corporation, 2000.

Reacti–Bind™ Streptavidin High Binding Capacity (HBC) Coated Plates flyer, Pierce Chemical Company, 2000.

Lifetime– and Color–Tailored Fluorophores in the Micro– to Millisecond Time Regime, Chen et al., *J. Am. Chem. Soc.,* vol. 122, pp. 657–660, 2000.

Spectroscopic Properties and Design of Highly Luminescent Lanthanide Coordination Complexes, de Sa et al., *Coordination Chemistry Reviews,* vol. 196, pp. 165–195, 2000.

Luminescence and Structure of Europium Compounds, Vicentini et al., *Coordination Chemistry Reviews,* vol. 196, pp. 353–382, 2000.

FLIPR 384: Essential Technology for Drug Discovery brochure, Molecular Devices Corp., undated.

Acumen Explorer brochure, Acumen, undated.

FLUOstar Galaxy brochure, BMG Labtechnologies GmbH, undated.

LUMIstar Galaxy brochure, BMG Labtechnologies GmbH, undated.

NEPHELOstar brochure, BMG Labtechnologies GmbH, undated.

POLARstar Galaxy brochure, BMG Labtechnologies GmbH, undated.

POLARstar Galaxy flyer, BMG Labtechnologies GmbH, undated.

REMP 384 Tube Technology flyer, REMP (USA) Inc., undated.

REMP 96–Technology flyer, REMP (USA) Inc., undated.

High Throughput Screening brochure, Greiner America, Inc., undated.

PW 384 brochure, Pan Vera Corporation, undated.

Protein Kinase C (PKC) tech specs, Pan Vera Corporation, undated.

\* cited by examiner

Fig. 19
Fig. 18
Fig. 16
Fig. 17

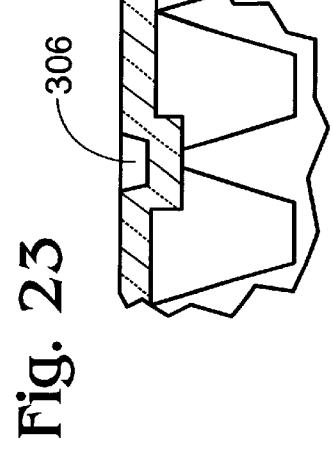
Fig. 23
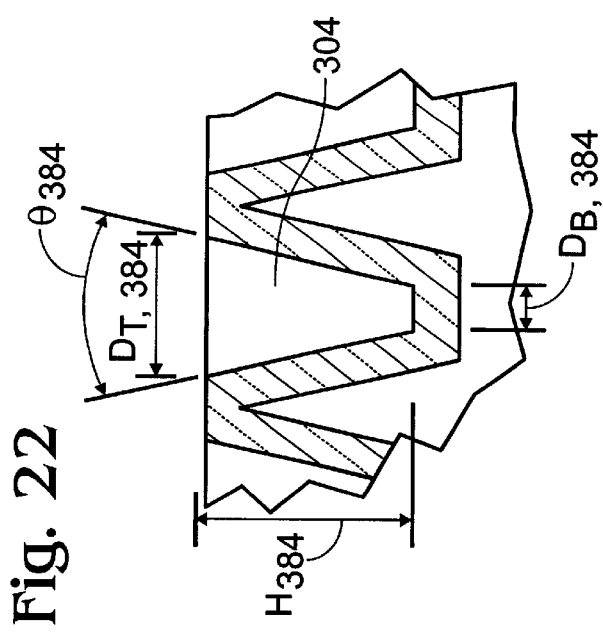
Fig. 22
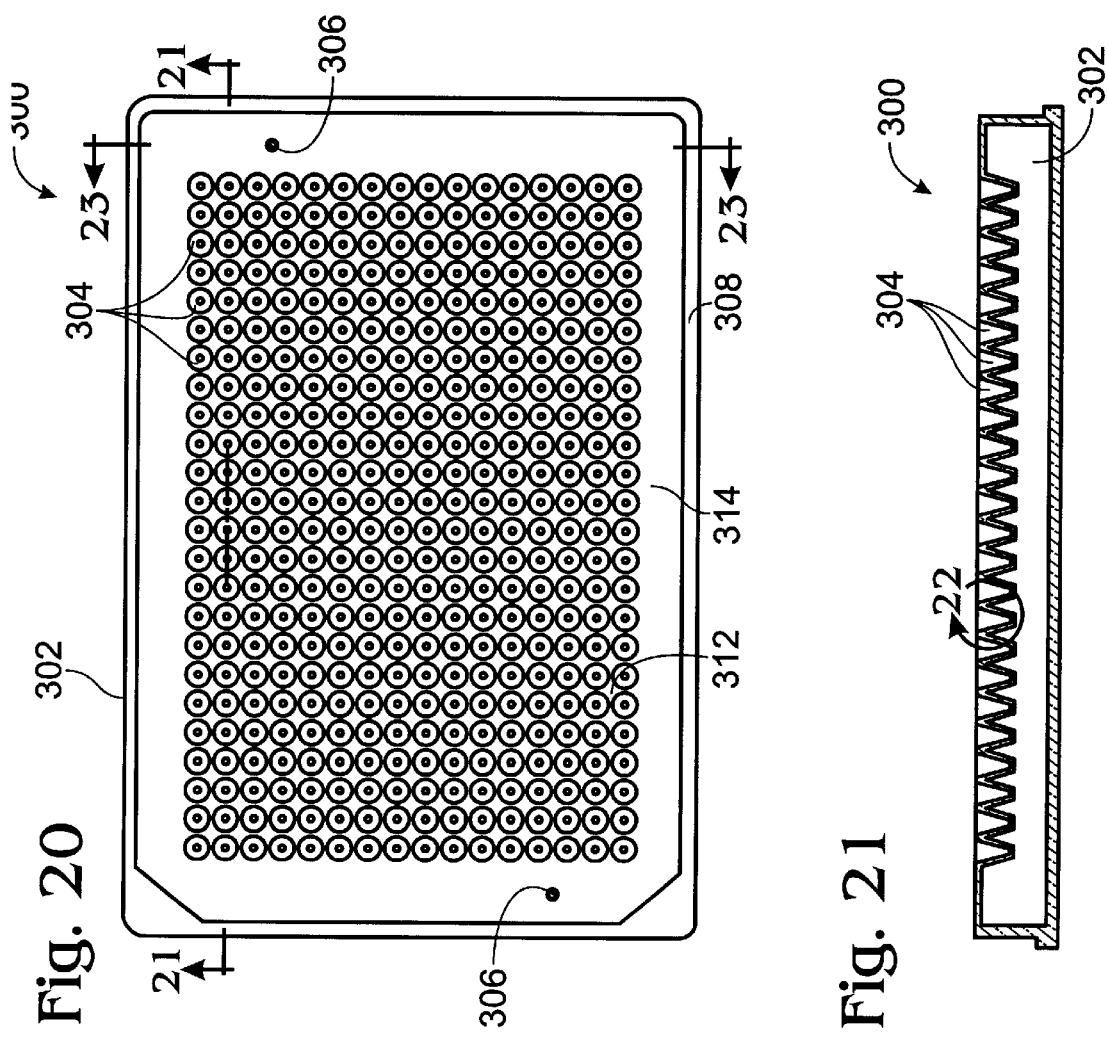
Fig. 20
Fig. 21

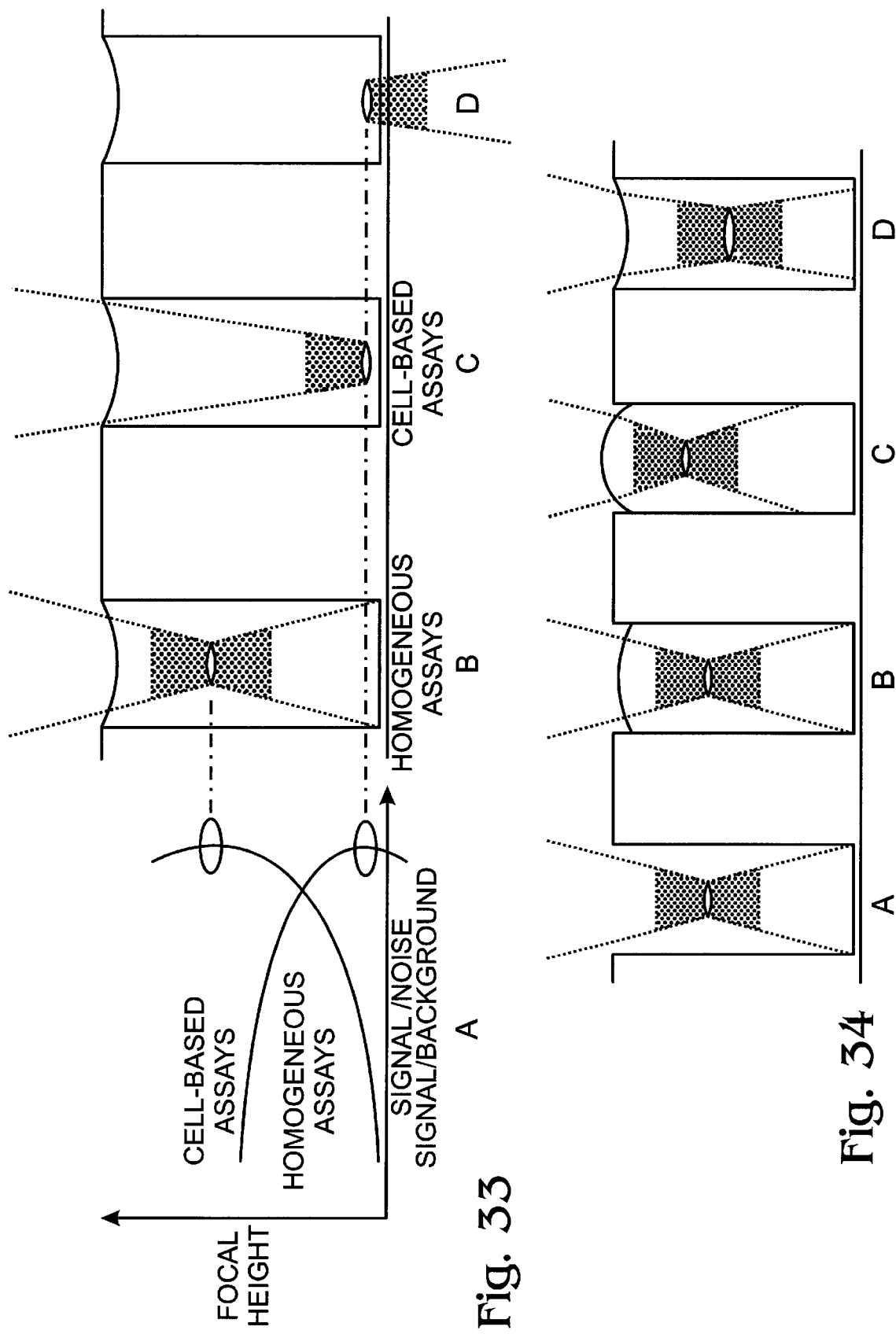

METHODS AND APPARATUS FOR DETECTING NUCLEIC ACID POLYMORPHISMS

CROSS-REFERENCES

This application is based upon and claims priority under 35 U.S.C. § 119 from the following U.S. Provisional Patent Applications, each of which is incorporated herein by reference: Serial No. 60/124,686, filed Mar. 16, 1999; Serial No. 60/125,346, filed Mar. 19, 1999; Serial No. 60/135,284, filed May 21, 1999; and Serial No. 60/167,463, filed Nov. 24, 1999.

This application is a continuation-in-part of and claims priority from the following PCT patent applications, all of which are incorporated herein by reference: Ser. No. PCT/US99/01656, filed Jan. 25, 1999; Ser. No. PCT/US99/08410, filed Apr. 16, 1999; and Ser. No. PCT/US00/00895 filed Jan. 14, 2000, entitled Methods and Apparatus for Detecting Polynucleotide Hybridization, of Inventors Douglas N. Modlin, Todd E. French, Jon F. Petersen, and John C. Owicki.

This application is a continuation-in-part of and claims priority from the following U.S. patent applications, all of which are incorporated herein by reference: Ser. No. 09/062,472, filed Apr. 17, 1998 now U.S. Pat. No. 6,071,748; Ser. No. 09/160,533, filed Sep. 24, 1998; Ser. No. 09/349,733, filed Jul. 8, 1999; and Ser. No. 09/468,440, filed Dec. 21, 1999.

This application hereby incorporates by reference the following PCT patent applications: Ser. No. PCT/US98/23095, filed Oct. 30, 1998; Ser. No. PCT/US99/03678, filed Feb. 19, 1999; Ser. No. PCT/US99/16057, filed Jul. 15, 1999; Ser. No. PCT/US99/16453, filed Jul. 21, 1999; Ser. No. PCT/US99/16621, filed Jul. 23, 1999; Ser. No. PCT/US99/16286, filed Jul. 26, 1999; Ser. No. PCT/US99116287, filed Jul. 26; 1999; and Ser. No. PCT/US99/24707, filed Oct. 19, 1999.

This application also hereby incorporates by reference the following U.S. provisional patent applications: Serial No. 60/117,278, filed Jan. 26, 1999; Serial No. 60/119,884, filed Feb. 12, 1999; Serial No. 60/121,229, filed Feb. 23, 1999; Serial No. 60/124,686, filed Mar. 16, 1999; Serial No. 60/125,346, filed Mar. 19, 1999; Serial No. 60/130,149, filed Apr. 20, 1999; Serial No. 60/132,262, filed May 3, 1999; Serial No. 60/132,263, filed May 3, 1999; Serial No. 60/138,311, filed Jun. 9, 1999; Serial No. 60/138,438, filed Jun. 10, 1999; Serial No. 60/138,737, filed Jun. 11, 1999; Serial No. 60/138,893, filed Jun. 11, 1999; Serial No. 60/142,721, filed Jul. 7, 1999; Serial No. 60/153,25 1, filed Sep. 10, 1999; Serial No. 60/164,633, filed Nov. 10, 1999; Serial No. 60/165,813, filed Nov. 16, 1999; Serial No. 60/167,301, filed Nov. 24, 1999; filed Jan. 26, 2000, entitled CYTOSKELETAL BINDING ASSAYS, of inventors Michael K. Helms and Todd E. French.

This application also incorporates by reference the following publications: William Bains, *Biotechnology from A to Z* (1993); Richard P. Haugland, *Handbook of Fluorescent Probes and Research Chemicals* ($6^{th}$ ed. 1996); Joseph R. Lakowicz, *Principles of Fluorescence Spectroscopy* ($2^{nd}$ Edition 1999); and Bob Sinclair, *Everything's Great When It Sits on a Chip: A Bright Future for DNA Arrays*, 13 THE SCIENTIST, May 24, 1999, at 18.

FIELD OF THE INVENTION

The invention relates to nucleic acids. More particularly, the invention relates to methods and apparatus for detecting nucleic acid polymorphisms in luminescence-based assays.

BACKGROUND OF THE INVENTION

Nucleic acids (or polynucleotides) are linear polymers composed of covalently linked nucleotides. In tun, nucleotides are small organic compounds composed of phosphoric acid, a carbohydrate, and a purine such as adenine (A) or guanine (G) or a pyrimidine such as cytosine (C), thymidine (T), or uracil (U).

Nucleic acids may be single-stranded or double-stranded, where double-stranded nucleic acids are composed of two single-stranded nucleic acids bound to one another through noncovalent base-pairing interactions to form a hybrid. Such binding or hybridization will occur if the sequences of the single-stranded nucleic acids are "complementary" (or nearly complementary), so that for example wherever there is an A in one strand there is a T or a U in the other, and wherever there is a G in one strand there is a C in the other.

Nucleic acids in the form of deoxyribonucleic acid (DNA) and ribonucleic acid (RNA) encode genetic information that controls cellular function and heredity in biological systems. DNA encodes information at least in part in the form of genes, where genes are sequences of nucleotides that encode information for constructing a polypeptide. The sequence of nucleotides in a gene may vary due to insertions, deletions, repeats, inversions, translocations, and/or single and multiple nucleotide substitutions, among others. These variations may be termed polymorphisms, and genes that differ by polymorphisms may be termed alleles.

Polymorphisms and other genetic factors appear to contribute to virtually every human disease, conferring susceptibility or resistance and affecting both progression and severity. For example, variations in the apoE gene are associated with Alzheimer's disease, variations in the CCR5 chemokine receptor gene are associated with resistance to HIV infection, variations in the hemoglobin gene are associated with sickle cell anemia, and variations in glycosyltransferase genes are associated with the ABO blood groups. Thus, an understanding of the genetic contribution to disease may greatly impact the diagnosis, treatment, and prevention of disease. Moreover, an understanding of this genetic contribution also may help in identifying and understanding nongenetic (e.g., environmental) influences on disease.

Analysis of DNA sequence variations is becoming increasingly important in identifying the genes involved in both disease and normal biological processes, including development aging, and reproduction. For example, to understand disease, it is important to understand how genetic variation affects gene function. Response to therapies also can be affected by genetic differences. Thus, information about variations in DNA sequence may assist in the analysis of disease and in the development of diagnostic, therapeutic, and preventative strategies.

Efforts are now underway to sequence the human genome through a combination of public and private effort. However, these efforts will not yield significant information regarding variations in DNA sequence within he human population, because the DNA sequence that is being produced will for most sequence sites come only from a single individual. (An exception is regions where overlapping clones from different chromosomes will be sequenced; however, this overlap will include input only from two individuals and will amount to less than 10% of the complete sequence.) Thus, additional work is needed to discover the number and distribution of variations in human DNA.

As described above, there are several types of variations in DNA sequence, including insertions and deletions, differences in the copy number of repeated sequences, and single base pair differences. The latter most variations are the most frequent These variations are termed single nucleotide polymorphisms (SNPs) when the variant sequence type has a frequency of at least 1% in the population. SNPs have many properties that make them attractive as the primary analytical reagent for the study of human sequence variation. In addition to their frequency, SNPs are stable, having much lower mutation rates than repeat sequences. More importantly, SNPs will be often be the nucleotide sequence variations that are responsible for functional changes of interest.

SNPs are very common in human DNA. Any two random chromosomes differ at about 1 in 1000 bases. However, only about half or fewer of random pairs of chromosomes will differ for any particular polymorphic base (i.e., for any base for which the least common variant has a frequency of at least 1% in the population). Thus, there actually are more polymorphic sites in the human population, viewed in its entirety, than there are sites that differ in any particular pair of chromosomes. Altogether, there may be anywhere from 6 million to 30 million nucleotide positions in the genome at which variation can occur in the human population. Thus, overall, approximately one in every 100 to 500 bases in human DNA may be polymorphic.

Information about SNPs may be used in various ways in genetic analysis. First, SNPs can be used as genetic makers in mapping studies. For example, SNPs can be used for whole-genome scans in pedigree-based linkage analysis of families; for this purpose, a map of about 2000 SNPs has the same analytical power as a map of about 800 microsatellite markers, currently the most frequently used type of marker. Second, when disease genetics is studied in individuals in a population, rather than in families, the haplotype distributions and linkage disequilibria can be used to map genes by association methods. For this purpose, it has been estimated that 30,000 to as many as 300,000 mapped SNPs will be needed. Third, genetic analysis can be used in case-control studies to identify functional SNPs contributing to a particular phenotype. Most SNPs are located outside of coding sequences, because only three to five percent of the human DNA sequence encodes proteins. However, SNPs located within protein-coding sequences ("cSNPs") are of particular interest because they are more likely than a random SNP to have functional significance. It also is likely that some of the SNPs in noncoding DNA will have functional consequences, such as those in sequences that regulate gene expression. Discovery of SNPs that affect biological function should become increasingly important over the next several years, and should be greatly facilitated by the availability of a large collection of SNPs, from which candidates for polymorphisms with functional significance can be identified. Accordingly, SNPs discovery is an important objective of SNPs research.

SNPs will be particularly important for mapping and discovering the genes associated with common diseases. Many processes and diseases are caused or influenced by complex interactions among multiple genes and environmental factors. These include processes such as development and aging, and diseases such as diabetes, cancer, cardiovascular and pulmonary disease, neurological diseases, autoimmune diseases, psychiatric illnesses, alcoholism, common birth defects, and susceptibility to infectious diseases, teratogens, and environmental agents. Many of the alleles associated with health problems are likely to have a low penetrance, meaning that only a small percentage of individuals carrying the alleles will develop disease. However, because such polymorphisms are likely to be very common in the population, they may make a significant contribution to the health burden of the population. Examples of common polymorphisms associated with an increased risk of disease include the ApoE4 allele and Alzheimer's disease, and the APC I1307K allele and colon cancer.

Most of the successes to date in identifying (a) the genes associated with diseases inherited in a Mendelian fashion, and (b) the genetic contribution to common diseases, e.g., BRCA1 and 2 for breast cancer, MODY 1, 2, and 3 for type 2 diabetes, and HNPCC for colon cancer, have been of genes with relatively rare, highly penetrant variant alleles. These genes are well-suited to discovery by linkage analysis and positional cloning techniques. However, the experimental techniques and strategies usefull for finding low penetrance, high frequency alleles involved in disease are usually not the same, and not as well developed, as those that have been applied successfully in positional cloning. For example, pedigree analysis of families often does not have sufficient power to identify common, weakly contributing loci. The types of association studies that do have the power to identify such loci efficiently require new approaches, techniques, and scientific resources to make them as robust and powerful as positional cloning. Among the resources needed is a genetic map of much higher density than the existing, microsatellite-based map. Association studies using a dense map should allow the identification of disease alleles even for complex diseases. SNPs are well suited to be the basis of such a map.

Available technologies can be used in SNPs analysis. For example, U.S. Pat. No. 5,888,819 to Goelet et al. describes a technique involving first binding a primer to a single-stranded polynucleotide immediately adjacent a polymorphic site of interest, and extending the primer by a terminating nucleotide such as a labeled ddNTP. Incorporation of the labeled base is then detected indicating what allele is present in the sample at the polymorphic site. A similar technique is described in U.S. Pat. No. 5,302,509 to Cheeseman. A significant drawback with the single-base extension methods described in Goelet et al. and Cheeseman is that they require labor-intensive affinity or physical separation steps to remove all nonterminating labeled nucleotides prior to detection, so that signal from bound nucleotide can be detected without interference with signal from unbound labeled nucleotides. The complexity of these single-base extension methods renders them impractical for some applications, such as SNPs testing procedures that require rapid testing of large numbers of samples. Thus, there is a significant need for simpler methods of detecting single-base variability in polynucleotides, in particular methods that are capable of detecting incorporated labeled nucleotides in the presence of unbound nucleotides, homogeneously, without labor-intensive physical separation steps. Such novel methods and the associated apparatus would be useful among other places in the high-throughput, large-scale discovery of SNPs, where "discovery" refers to finding new SNPs. Moreover, such methods and apparatus would be useful for scoring known SNPs in genotyping assays, where "scoring" refers to methods of determining the genotypes of individuals for particular SNPs that already have been discovered.

SUMMARY OF THE INVENTION

The invention provides methods and apparatus for detecting nucleic acid polymorphisms in luminescence-based assays.

BRIEF DESCRIPTION OF THE DRAWINGS

FIG. 16 is a top view of a 96-well microplate constructed in accordance with the invention.

FIG. 17 is a cross-sectional view of the microplate in FIG. 16, taken generally along line 17—17 in FIG. 16.

FIG. 18 is a first enlarged portion of the cross-sectional view in FIG. 17, showing details of a sample well.

FIG. 19 is a second enlarged portion of the cross-sectional view in FIG. 17, showing details of a reference fiducial.

FIG. 20 is a top view of a 384-well microplate constructed in accordance with the invention.

FIG. 21 is a cross-sectional view of the microplate in FIG. 20, taken generally along line 21—21 in FIG. 20.

FIG. 22 is an enlarged portion of the cross-sectional view in FIG. 20, showing details of a sample well.

FIG. 23 is an enlarged cross-sectional view of the microplate in FIG. 20, taken generally along line 23—23 in FIG. 20, showing details of a reference fiducial.

FIG. 33 is a partially schematic cross-sectional view of three sample wells, showing alternative positions of a sensed volume.

FIG. 34 is a partially schematic cross-sectional view of four sample wells, showing how the meniscus affects the shape and position of the sensed volume within a sample well.

DETAILED DESCRIPTION OF THE INVENTION

The invention provides methods and apparatus for detecting nucleic acid targets in luminescence assays. These targets may include nucleic acid polymorphisms, such as single nucleotide polymorphisms (SNPs). Generally, the methods may include (1) allele-specific hybridization, using luminescence detection, (2) allele-specific oligonucleotide ligation, using dye-labeled oligonucleotide ligation with luminescence resonance energy transfer (FRET) detection, and (3) allele-specific nucleotide incorporation, using primer extension with luminescence polarization (FP) detection. More specifically, the methods may include (1) locating a sample containing a nucleic acid material at an examination site, (2) illuminating the sample, (3) detecting light transmitted from the sample, and (4) determining the presence, absence, and/or identity of a nucleic acid target in the sample using the light transmitted from the sample. The steps of illuminating and detecting may be performed on a single sample or (serially and/or simultaneously) on a plurality of samples.

Figure 1:
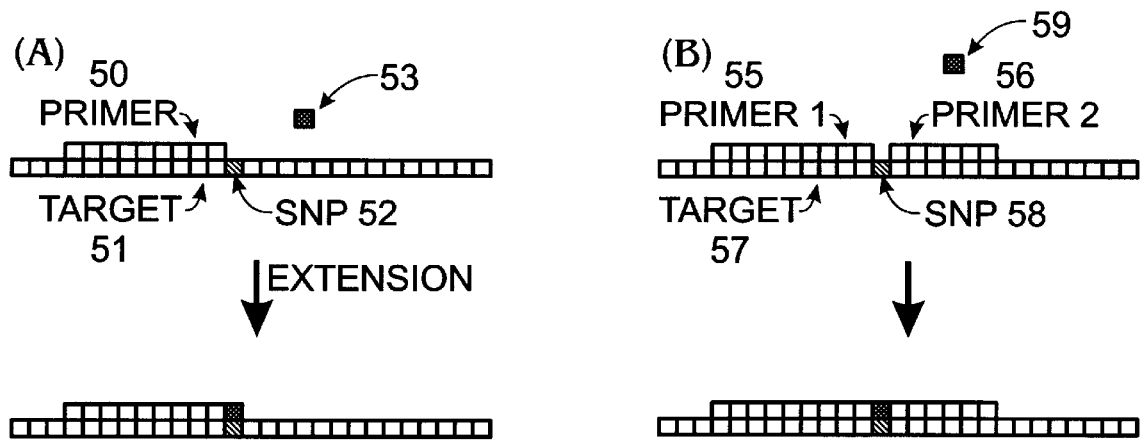
FIG. 1 is a schematic view of (A) an incorporation assay and (B) a ligation assay provided by the invention.

Overview of assays. FIG. 1 is a schematic view of (A) an incorporation assay and (B) a ligation assay provided by the invention. These assays may be used to identify a SNP in a target sequence. In Panel A, a single-stranded nucleic-acid primer 50 is hybridized to a target sequence 51, one base pair upstream of a SNP position 52. A dye-labeled dideoxy nucleoside triphosphate (ddNTP) 53, or dye terminator, corresponding to the SNP is included in the sample, so that it will be enzymatically incorporated onto the primer by a polymerase if the SNP allele in question is on the target sequence. In Panel B, first 55 and second 56 single-stranded nucleic-acid primers are hybridized to a target sequence 57, first primer 55 one base pair upstream of a SNP position 58 and second primer 56 one base pair downstream of the SNP position. A deoxy nucleoside triphosphate (dNTP) 59 corresponding to the SNP is included in the sample, so that it will be ligated between the two primers by a ligase if the SNP allele in question is on the target sequence.

The incorporation of free nucleotide into the primer(s) in Panels A and B may be determined using luminescence. In the assay of Panel A, the ddNTP may be luminescently labeled, and the incorporation of the ddNTP into the primer may be determined by observing an increase in polarization, or an increase in energy transfer to or from an energy transfer partner associated with the primer. In the assay of Panel B, the dNTP may be luminescently labeled, and the incorporation of the dNTP into (either or both of) the two primers may be determined by observing an increase in polarization or energy transfer, as described above. Alternatively, the dNTP may be unlabeled, and the incorporation of the dNTP may be determined by observing an increase in energy transfer between energy transfer partners associated with each of the two primers brought together by the ligation.

Energy transfer may be observed using any suitable mechanism; preferred methods ad apparatus for energy transfer are described in subsequent sections. In some embodiments, energy transfer may be observed using intensity-based methods, by observing decreases in donor intensity, increases in acceptor intensity (if the acceptor is luminescent), or changes in the ratio of the two intensities. In other embodiments, energy transfer may be observed using lifetime-based methods, by observing decreases in donor lifetime, increases in acceptor lifetime (for luminescent acceptors), or changes in the ratio of the two lifetimes. Lifetime-based detection can be carried out using frequency-domain methods (e.g., phase/modulation detection), time-domain methods (e.g., pulse excitation with gated integration), or hybrid methods combining features of both.

Polarization also may be observed using any suitable mechanism; preferred methods and apparatus for polarization are described in subsequent section. Polarization assays exploit the decrease in rotational mobility that accompanies incorporation of a free nucleotide into a primer. Specifically, free luminescent ligands undergo relatively rapid rotation and produce relatively depolarized emission following excitation with polarized light, whereas incorporated luminescent ligands undergo relatively slow rotation and produce relatively polarized emission following excitation. These differences may be observed by measuring intensities of luminescence emissions parallel and perpendicular to an excitation polarization, and then using these quantities to evaluate a suitable mathematical function, such as polarization or anisotropy.

Aspects of the invention include mechanisms that augment the increase in polarization upon incorporation, so that it can be measured more easily. For example, the change in polarization upon incorporation into the primer can be increased by making any linker between the luminophore and terminator as short and/or rigid as possible, while maintaining relevant substrate properties for the enzymes involved in the assay. Short and/or rigid linkers will restrict luminophore motion relative to the terminator, reducing the "propeller effect" so that the luminophore more accurately reports the motion of both the incorporated and free terminator. The rigidity of the linker may be increased by avoiding using hexanoic acid linkers, which typically are long and flexible, and by using amide groups in place of methylene groups, among other mechanisms.

The change in polarization upon incorporation into the primer also can be increased by including an appropriately positioned energy transfer acceptor on the primer, so that energy transfer occurs from the luminophore to the acceptor upon incorporation. Such energy transfer will shorten the lifetime of the luminophore, thereby increasing its polarization (because polarization varies inversely with lifetime, all else being equal).

The change in polarization upon incorporation into the primer also can be increased by decreasing the mobility of the hybrid. Mobility can be decreased by increasing the size of the hybrid, either directly or by forming a complex with a mass label. Suitable mass labels include other molecules and beads, among others. The use of mass labels is described in detail in PCT patent application Ser. No. PCT/US99/24707, which is incorporated herein by reference. Mobility also can be decreased by attaching the unlabeled polynucleotide to a surface, such as the surface of the sample holder. Attachment to other molecules, beads, and/or surfaces may be accomplished using any of a number of well-known reactive soups.

Figure 2:
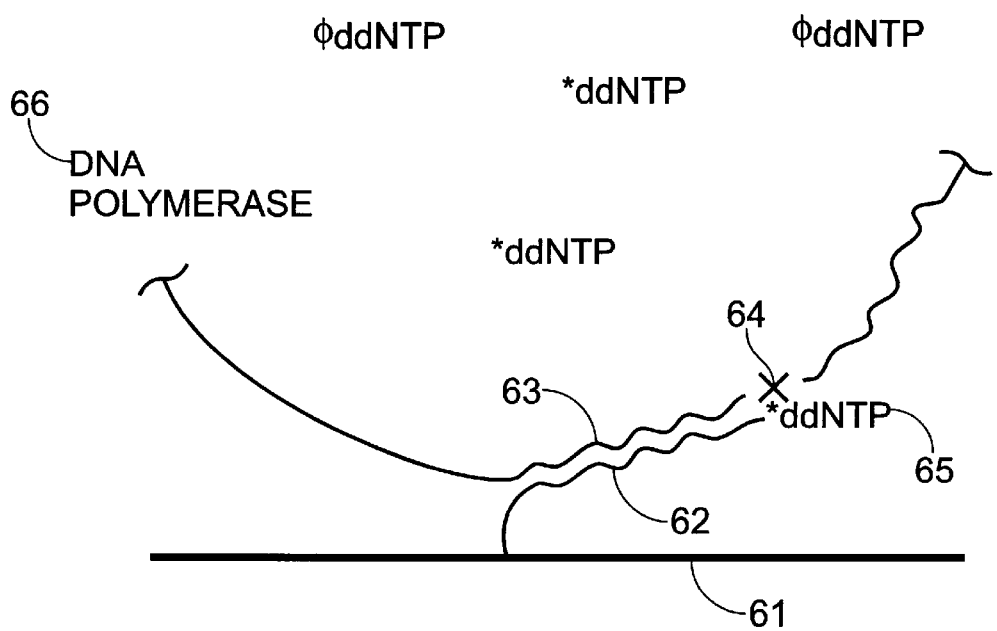
FIG. 2 is a schematic view of a surface-based incorporation assay showing how primer mobility can be reduced by attachment to a surface.

FIG. 2 shows how primer mobility can be reduced by attachment of the primer to a surface. Here, a substrate (e.g., microplate) surface 61 is activated with any of an assortment of chemistries by which one can immobilize, via a single point of attachment, an unlabeled oligonucleotide 62 of a sequence designed specifically to recognize a complementary sequence 63 on a PCR or other target nucleic acid of the same or, more likely, much larger size. For SNPs detection, the primer would be designed, as for the solution-based case, to come within one base of the SNP 64. Incorporation of the ddNTP 65 by a polymerase 66 would result in a dramatic polarization change, taking the free nucleotide label to a surface-immobilized state. The spectral properties of the label would identify which of up to four nucleotides were actually incorporated.

Quantities such as energy transfer and polarization may be monitored using lifetime-based and intensity-based methods. Lifetime-based methods have several advantages over intensity-based methods. For example, lifetime-based detection increases precision by monitoring an intensive quantity, luminescence lifetime, rather than an extensive quantity, luminescence intensity. In addition, lifetime-based detection is able to reject background interference from light scattering and luminescent contaminants that have a lifetime different from that of the label being analyzed. This becomes increasingly important as sample volume and hence signal-to-background ratios are decreased. Decreasing sample volume is advantageous for various reasons, including economy of reagent consumption and the ability to utilize smaller biological samples.

Because lifetime methods may be used to distinguish luminescence signals even if the associated excitation and emission spectra are similar, two- to four-lifetime detection methods may be constructed that require only one excitation and one emission wavelength. For example, call a series of four luminescent labels with similar excitation and emission spectra but distinguishable luminescence lifetimes F1, F2, F3, and F4. Using the four dideoxy terminators, create the dye terminators ddATP-F1, ddTTP-F2, ddCTP-F3, and ddGTP-F4. The one-base-pair-extension/termination procedure with a labeled primer is carried out as described above, but with all four dye terminators present. After reaction, the amount of energy transfer corresponding to the interactions of each of the four luminophores with the label on the primer can be assessed to determine the SNP (or SNPs, if heterozygous) that were present in the sample. A similar approach may be used in the ligation assay, using multiple labeled dNTPs.

The number of required labeled-nucleotides depends on the number of alleles corresponding to the polymorphism of interest. For example, if there are four alleles, each differing by a single nucleotide substitution (A, T, G, C), then a four-lifetime method is appropriate. Alternatively, if there are only three or two alleles, then a three-lifetime or two-lifetime method is appropriate, respectively.

The choice of a compatible set of luminescent labels for spectroscopic analysis is a different and more complicated problem than the choice of such labels for sequencing. This is especially true for polarization analysis, because polarization labels preferably are chosen to minimize energy transfer, which decreases polarization, and because polarization labels must be selected to obtain spectral separation while maintaining good polarization properties. Suitable sets of labels may be constructed using novel luminescent labels and/or novel combinations of pre-existing luminescent labels. Suitable sets of dyes can be constructed by selecting one label from each of up to the following four groups of labels, among others (1) Cascade blue or aminomethyl coumarin, (2) fluorescein or rhodamine green, (3) rhodamine 6G or tetramethyl rhodamine, and (4) sulforhodamine 101 or lissamine rhodamine B. Such a selection could result in 16 different quartets, 32 different triplets, and 48 different pairs, based on combinatorics.

It also is possible to use combinations of wavelength and lifetime discrimination to determine the incorporation of the four labeled nucleotides, if F1 through F4 differ from one another in combinations of excitation/emission wavelengths and lifetimes that can be reliably distinguished from one another. Dyes can be distinguished by using wavelength and lifetime sequentially. For example, F1 through F3 could be distinguished from F4 by wavelength, and F1 through F3 could be distinguished among themselves by lifetime. Dyes also can be distinguished by using wavelength and lifetime simultaneously. For example, F1 through F4 could be distinguished among themselves in a two-dimensional space based on wavelength and lifetime. It may be more reliable to use both wavelength and lifetime than either alone, depending on the refinements in spectral and lifetime properties of dyes that are possible.

Figure 3:
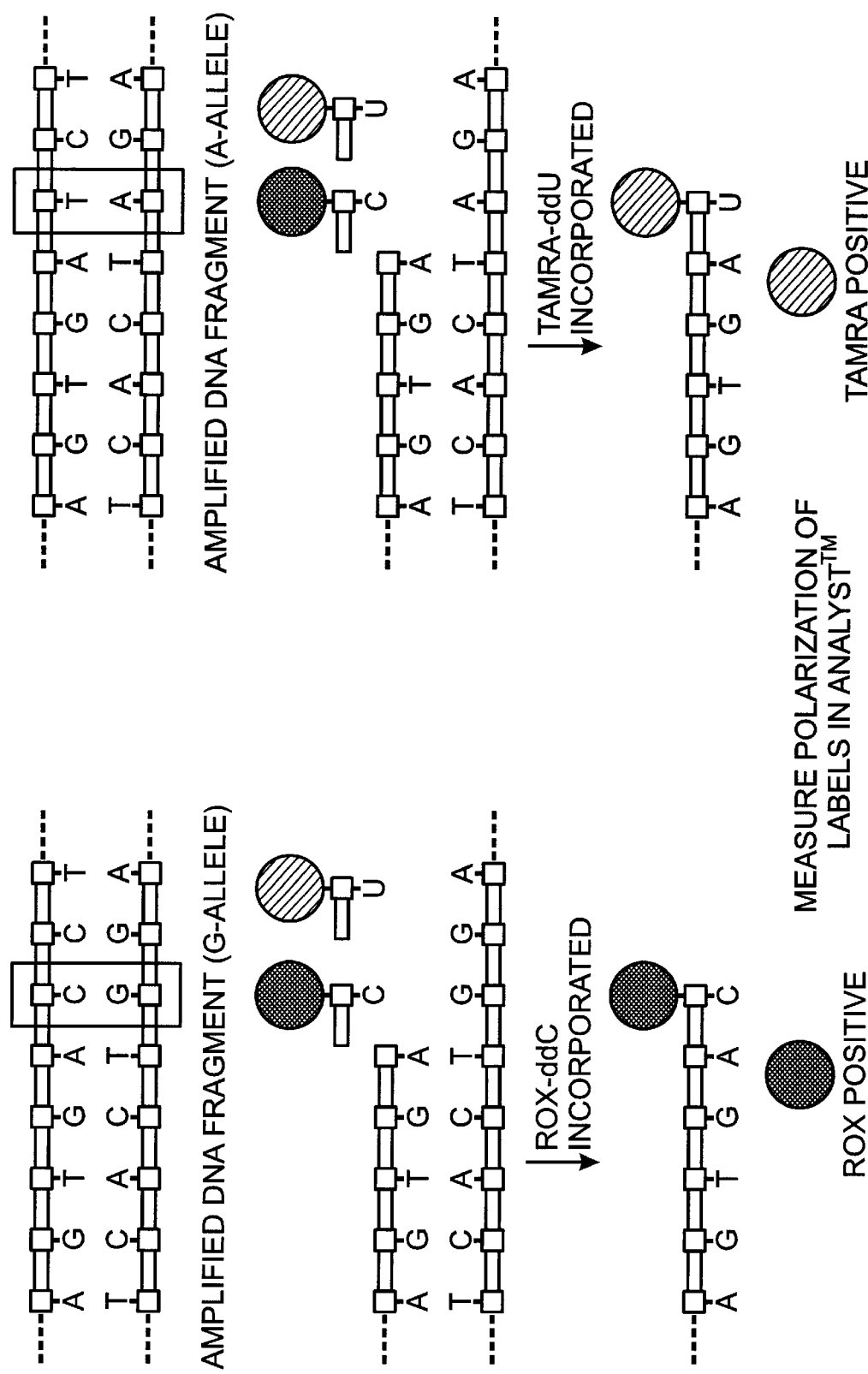
FIG. 3 is a schematic view of an incorporation assay showing how luminescence polarization can be used in a two-dye assay for SNPs detection.

FIG. 3 shows how luminescence polarization can be used in a two-dye assay for SNP detection. Specifically, luminescently labeled dideoxy-mononucleotides are used to detect and identify a particular SNP. This SNP involves a DNA fragment in which a particular base may be G (the G-allele) or A (the A-allele). A primer may be added to an amplified DNA fragment including the polymorphism, so that it binds with the DNA fragment. The primer is complementary to a sequence of DNA up to but not including the polymorphism. An appropriate polymerase, such as DNA polymerase, and appropriate mononucleotides, such as ROX-labeled dideoxy-cytosine (ddC) mononucleotides and TAMRA-labeled dideoxy-uracil (ddU) mononucleotides, also are added to the amplified DNA fragment. Here, ROX denotes 6-carboxy-X-rhodamine, and TAMRA denotes N,N,N',N'-tetramethyl-6-carboxyrhodamine. If the polymorphism includes G, the ROX-labeled ddC mononucleotide will be added to the primer by the polymerase, increasing its luminescence polarization by reducing its rotation rate. If the polymorphism includes A, the TAMRA-labeled ddU mononucleotide will be added to the primer, increasing its luminescence polarization by reducing its rotation rate. The polymorphism may be identified by determining which luminescence experiences an increase in luminescence polarization.

Figure 4:
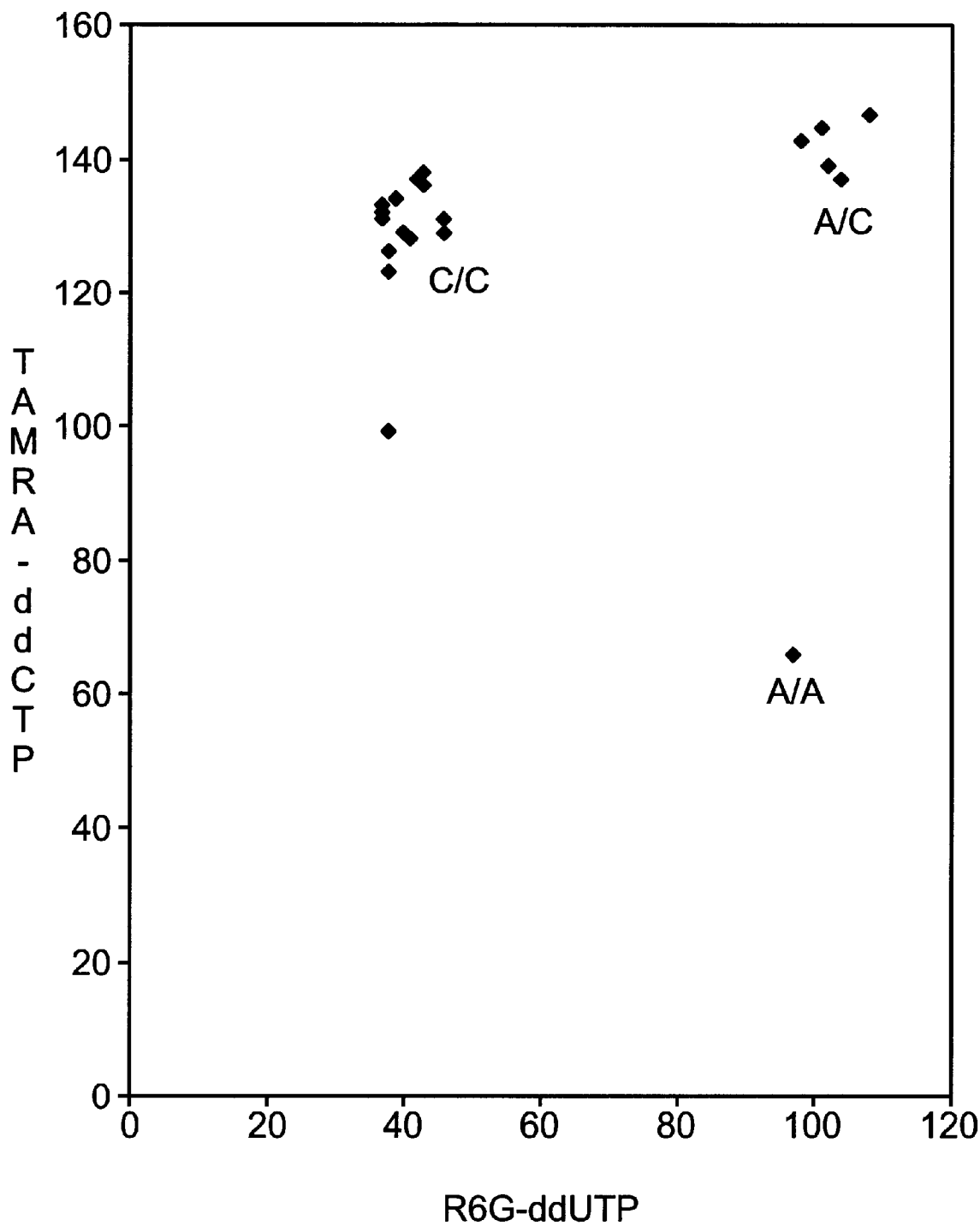
FIG. 4 is a graph showing results obtained in detecting a two-allele SNP using a template-directed dye-terminator incorporation assay and high-efficiency luminescence polarization detection.

FIG. 4 and the following table show results obtained at LJL BioSystems, Inc. by applying the assay of FIG. 3 to score the A/C SNP of FIG. 3. Specifically, DNA samples were obtained from 24 different individuals and interrogated for genotype. The results show that the homozygous A/A genotype was present in one individual (~5% of the population), the heterozygous A/C genotype was present in five individuals (~24% of the population), and the homozygous C/C genotype was present in fifteen individuals (~71% of the population), with three individuals uninterrogated due to PCR failure.

| | mP Values | | | | |
|---|---|---|---|---|---|
| | R6G- | TAMRA- | Genotype | | |
| Individuals | ddUTP | ddCTP | AA | AC | CC |
| 1 | 46 | 131 | | | X |
| 2 | 43 | 138 | | | X |
| 3 | 39 | 134 | | | X |

-continued

| | mP Values | | Genotype | | |
|---|---|---|---|---|---|
| Individuals | R6G-ddUTP | TAMRA-ddCTP | AA | AC | CC |
| 4 | 108 | 147 | | X | |
| 5 | 40 | 129 | | | X |
| 6 | 45 | 45 | PCR Failure | | |
| 7 | 34 | 31 | PCR Failure | | |
| 8 | 50 | 44 | PCR Failure | | |
| 9 | 102 | 139 | | X | |
| 10 | 42 | 137 | | | X |
| 11 | 97 | 66 | X | | |
| 12 | 101 | 145 | | X | |
| 13 | 43 | 136 | | | X |
| 14 | 37 | 133 | | | X |
| 15 | 98 | 143 | | X | |
| 16 | 41 | 128 | | | X |
| 17 | 37 | 131 | | | X |
| 18 | 46 | 129 | | | X |
| 19 | 38 | 123 | | | X |
| 20 | 104 | 137 | | X | |
| 21 | 37 | 132 | | | X |
| 22 | 38 | 99 | | | X |
| 23 | 38 | 126 | | | X |
| 24 | 42 | 137 | | | X |

The energy transfer and polarization assays presented above are homogeneous, i.e., there are no separation steps in these assays. It is possible to perform these assays in an inhomogeneous fashion with the same labeled nucleotides described above by using unlabeled primers, separating incorporated from unincorporated labeled nucleotides, and measuring the luminescence intensity at each lifetime for the incorporated labeled nucleotides. The separation might be accomplished, for example, by washing following capture of the sample or primers on a solid phase, such as a bead or microplate surface, using hybridization or other biospecific interaction.

It sometimes may be advantageous to attach or immobilize other reagents to a solid surface. For example, polymerase (which is used to add the labeled ddNTP onto an end of the primer) and/or ligase (which is used to ligate the labeled dNTP between two primers) may be immobilized on the solid surface. The polymerase or ligase may be chemically linked to the solid support and/or stabilized in dry form, for example, in a film or by lyophilization, so that it will solubilize and recover enzymatic activity in an aqueous sample. In some embodiments, all required reagents may be stabilized in a microplate well so that the assay can be run simply by adding an appropriate buffer and sample nucleic acid to the well and performing the luminescence assay.

Overview of nucleic acids. The assays provided by the invention include target and primer nucleic acids. Generally, these nucleic acids may include deoxyribonucleic acids (DNAs), ribonucleic acids (RNAs), and peptide nucleic acids (PNAs), among others, as well as fragments, derivatives, and analogs thereof, so long as each is enzymatically recognizable. The nucleic acids may be single stranded, double stranded, or multiply stranded. If the nucleic acids are double or multiply stranded, the method may include treating (e.g., heating or otherwise denaturing) the nucleic acids to permit access and/or binding to the nucleic acid (e.g., target) by a complementary nucleic acid (e.g., primer). The nucleic acids may be of any length, from oligonucleotides having fewer than about 100 bases to long chromosomes having millions of bases.

The nucleic acids can be characterized by their sequences. These sequences may be created de novo or copied or patterned after a natural sequence, such as that found in all or part of an exon, intron, gene, gene family, plasmid, cosmid, virus, virion, or chromosome, among others.

The nucleic acids can be isolated, synthesized, and/or manipulated using standard techniques from molecular biology. Suitable techniques are described in William Bains, Biotechnology from A to Z (1993), which is incorporated herein by reference. For example, target and primer nucleic acids can be labeled and/or amplified using the polymerase chain reaction (PCR), among others The target and primer nucleic acids may be brought into contact using any method for effectuating such contact. A preferred method is by mixing the materials in solution, although other methods also may be used, such as attaching one or more components to a solid support such as a bead or surface, so long as the nucleic acids retain at least some specificity and binding affinity following such coupling.

The target and primer nucleic acids may be brought into contact under conditions conducive to hybridization. These conditions will vary with the nucleic acids due to the unique melting temperatures and hybridization properties of different polynucleotides. Melting temperature is determined largely by guanine/cytosine concentration in the hybrid. Generally, lower temperature and higher ionic strengths favor hybridization. However, higher temperatures and lower ionic strengths can be used to increase specificity at the expense of decreased sensitivity, because these conditions destabilize nonspecific hybrids. In most applications, it is preferable for the concentration of primer nucleic acid to be at least about as great as the concentration of target nucleic acid. In PCR assays, it is preferable for the concentration of primer to exceed the concentration of target, so that multiple primers can be labeled during multiple PCR cycles, enhancing signal.

Additional agents can be used to facilitate hybridization by destabilizing single-stranded nucleic acids, lowering melting temperatures, concentrating nucleic acids, and/or blocking and reducing nonspecific binding to substrate. For example, formamide lowers melting temperatures, so hybridizations can be performed at lower temperatures. Blocking agents (such as bovine serum albumin, sheared/denatured DNA, casein, and nonfat dry milk) reduce nonspecific binding, although they may spuriously increase polarization if they act by binding labeled polynucleotides. Excluding agents (such as dextran) effectively concentrate polynucleotide by excluding them from solution, thereby enhancing hybridization.

Overview of luminescence detection system. The detection of nucleic acid polymorphisms can be enhanced using high-sensitivity luminescence methods, including luminescence resonance energy transfer, luminescence polarization, and luminescence lifetime, among others. The detection also can be enhanced by improving (1) the assay system, including the assay chemistry, (2) the microplate or other sample holder, and (3) the instrument including background reduction techniques, such as FLARe™ luminescence-lifetime methodologies. These and other improvements described in subsequent sections may (1) enhance signals, (2) enhance signal-to-noise and signal-to-background ratios, (3) reduce sample volumes, (4) reduce false negatives and false positives, and (5) enhance measurement throughputs.

Signal may be enhanced in several ways, including (1) using a high color temperature light source, such as a xenon arc lamp, in a continuous illumination mode, and (2) using a sample holder whose shape is "matched" to the shape of the optical beam of the instrument, especially if the sample holder is elevated to bring the sample closer to a detector. The high color temperature light source increases the number of usable photons, which is important because the lower limit of the signal-to-noise ratio is set by the square root of the total number of photons collected in the measurement.

Signal-to-background ratios can be enhanced in several ways, including (1) using confocal optical systems having a sensed volume to avoid luminescence from the microplate walls, (2) selecting a microplate or other substrate that increases the signal and reduces the luminescent background from materials in the microplate, (3) selecting the light sources, luminescence filters, optics, signal collection electronics, and mechanical system used in the luminescence detection optical system for maximum signal-to-background ratio, and (4) utilizing signal processing, background subtraction, and luminescence lifetime techniques, particularly FLAMe™ methodology for background reduction, as described below.

Sample volumes can be reduced by matching the shape of the sample holder to the shape of the optical beam of the instrument. Simple calculations show that the number of luminescent molecules obtained from a typical PCR reaction is sufficiently high that the resulting luminesence signal will be considerably above the lower detection limit for polarization measurements in the light detection device described below, even after the sample is aliquoted in 1–10 $\mu$L amounts between 96, 384, 1516, or more sample wells. Specifically, samples taken from humans typically contain about $10^6$ cells, and PCR amplification factors typically are in the range $10^6$–$10^{12}$. If the PCT gain is about $10^6$, the concentration of luminescent label will be about 0.2 $\mu$M in a 10 $\mu$L sample, high enough readily to detect expected polarization changes. If the PCR gain is higher, the concentration of luminescent label also will be higher, so that sample volumes can be scaled down even further, for example, to about 1 $\mu$L or lower.

The methods and apparatus presented for detecting SNPs may reduce the required amounts of sample and reagents, and allow the use of conventional microplate technology, while avoiding the higher error rates associated with SNPs detection using DNA chips. DNA chips generally attempt to detect SNPs by measuring the extent of hybridization of DNA targets to DNA probes immobilized on the chip surface. Single-base mismatches are difficult to detect when the immobilized DNA probes are relatively long compared to the mismatch, e.g., DNA chips often use 10-mers or 20-mers to achieve sequence uniqueness. In addition to reducing cost, microplate technology also can be expected to increase turnaround time for custom DNA arrays.

The methods and apparatus provided by the invention may be used for the discovery and/or scoring of SNPs, mong other applications. These methods and apparatus also may be combined with other approaches, including "wet bench", computational, and/or multiplexing approaches, to generate additional information regarding a genome of interest (e.g. a map location or haplotype). Moreover, the invention may be used for drug research and accelerated drug discovery, combinatorial chemistry, life science research, DNA sequencing, genome studies, and genetic screening, among others.

Aspects of the invention may include SNPs discovery. These aspects may focus on finding SNPs throughout the genome, or in or adjacent regulatory and coding regions, or in particular types or sets of genes within the coding regions. These aspects also may focus on finding SNPs related to particular processes, organs, or diseases, or functional variants of genes.

Aspects of the invention also may include SNPs scoring. SNPs "scoring" is used to determine the genotypes of individuals for particular SNPs that already have been discovered. SNPs may be "scored" to stratify a population based on genotype. SNPs may be scored using various mechanisms. For example, as described above, SNPs may be scored by taking a DNA template, annealing a complementary primer, and then performing an extension reaction using dye-labeled ddNTPs. The dye-labeled ddNTP tumbles freely in solution if unincorporated, but is restricted in its tumbling if incorporated into a polynucleotide chain. The difference in tumbling may be measured using luminescence polarization, together with combinations of sample holders and/or detection optics and methods as described herein.

Additional aspects of the invention are described below and in patent applications cross-referenced above and incorporated herein by reference. For example, the invention may include combining the sample and reference polynucleotides with a luminescent reference compound, and determining the intensity of light emitted from the labeled nucleotide as a function of the intensity of light emitted from the reference compound. The remainder of the detailed description is divided into nine sections: (1) experimental procedures, (2) description of selected luminescence assays, (3) description of luminescence apparatus, (4) methods of measuring luminescence, (5) signal enhancement, (6) description of preferred light sources, (7) description of microplates, (8) application of sensed volumes, and (9) background subtraction.

1. Experimental Procedures

Introduction

This section presents applications of the invention to the detection of SNPs, including preferred materials, apparatus, and procedures. In summary, amplicons were amplified from purified genomic DNA containing the SNP of interest. Luminescent ddNTPs were then added in the primer extension reaction. Identicaton of the specific luminescent ddNTP incorporated at the polymorphic site was determined in a homogenous luminescent polarization assay. Covalent linkage of the luminophore onto the primer increases the molecular weight of ddNTP labels at least tenfold, resulting in increased polarization. Polarization is calculated in a ratiometric formula with the units of mP.

Experimental Outline

1. PCR Amplification of Template DNA
    Mix contains PCR primers, regular dNTPs, and source DNA (usually genomic DNA) and polymerase
    Goal: obtaining sufficient PCR product with the minimal amount of PCR primers and dNTPs
2. Degradation of PCR Primers and dNTPs
    Uses alkaline phosphatase and exonuclease I
    Goal: complete removal of excess primers and dNTPs
3. Dye-labeled Terminator Incorporation Assay
    Mix contains internal extension primer immediately upstream from the polymorphic site, luminescent dye-labeled ddNTPs, and sequenase
    Goal: efficient incorporation of free ddNTP-label
4. Polarization Detection Specialty Materials 1. Dye-ddNTP R6ddUTP, 100 $\mu$M (NEN, Cat.# NEL-488)
    ROX-ddGTP, 100 $\mu$M (NEN, Cat.# NEL-479)
    TAMRA-ddCTP, 100 $\mu$M (NEN, Cat.# NEL-473)
    BFL-14-ddATP, 100 $\mu$M (NEN, Cat.# NLP-999E001)
Here, R6G denotes rhodamine 6G, ROX denotes 6-carboxy-X-rhodamine, TAMRA denotes N,N,N',N'-tetramethyl-6-carboxyrhodamine, and BFL denotes bodipy-fluorescein.

2. AmpliTaq AmpliTaq Gold (PE BioSystems, 1000 U, 5 U/μL, Cat.# N808-0247)

GeneAmp 10× PCR Gold Buffer (PE BioSystems, Cat.# 4306894)

3. EXO & SAP Phosphaitta, alkaline, shrimp (Boehringer Mannheim, 1000 units, Cat.# 1 758 250)

*E. Coli* Exonuclease I (Amersham Pharmacia, 2500 units, Cat.# E70073Z)

4. Sequenase Thermo Sequenase DNA Polymerase, 32 U/μL (Amersham Pharmacia Biotech, Cat.# E79000Y), or AmpliTaq FS, 8 U/μL (PE BioSystem, available in Dye Terminator Core Kit, Cat.# 402118)

5. Excitation/Emission Filters and Dichroic Mirror

|  | Ex. (nm) | Ex. Filter | Em. (nm) | Em. Filter | Beamsplitter |
|---|---|---|---|---|---|
| BDF | 490 | 490-10 | 520 | 520-10 | 50/50 |
| R6G | 525 | 510-10 | 550 | 550-10 | 50/50 |
| TAMRA | 552 | 550-10 | 575 | 580-10 | 50/50 |
| ROX | 580 | 580-10 | 605 | 610-10 | 50/50 |

6. Plates Microseal skirted 96-well plates, Black (MJ Research, Inc., Cat.# MSP-9661) or Clear (MSP-9601), and/or LJL HE plates, and/or Costar microplates

EXAMPLE 1

Primer Extension from Synthetic Templates

A. Experimental Procedure

1. We have used the ApoE polymorphism as a model system. Synthetic templates were designed to correspond to the common sequence variations occurring at codon 112. The sequences are as follows, with the [ ] indicating the polymorphic site; four templates were made for all four possible base variations at this position:

ApoE-112 templates:

5' gctgg gcgcg gacat ggagg acgtg [C/T/A/G] gcggc cgcct ggtgc agtac cgcgg 3'

Specific extension primers bind just upstream from the polymorphic site. Because we used a two-step cycling primer-extension reaction with annealing and extension occurring at 60° C., the extension primers were designed to have annealing temperatures of 70° C. or higher. The sequence is as follows:

ApoE-112 extension primer:

5' ccgcg gtact gcacc aggcg gccgc 3'

2. Assemble reactions in MJ™ 96-well PCR plates, which can be read directly on an Analyst™ detection platform (LJL BioSystems, Inc.) at the end of the extension reaction. Alternatively, reactions can take place in tubes and then be transferred to LJL™ or Costar™ plates for FP measurements.

| 3. 5× reaction buffer: | Tris-HCl, pH 9.0 | 250 mM |
|---|---|---|
|  | KCl | 250 mM |
|  | NaCl | 25 mM |
|  | MgCl$_2$ | 10 mM |
|  | Glycerol | 40% |

4. Labeled-ddNTP Mix: To use all four labels, mix equal volumes of four ddNTPs for a final concentration of 25 μM for each dye; adjust concentrations if only one or two colors will be detected simultaneously. To use only tree or two dye-ddNTPs, supplement unlabeled ddNTPs for the other one or two nucleotides to reduce misincorporation. Labeled ddNTPs may be stored in a refrigerator or freezer and should not be repeatedly frozen and thawed. We store aliquoted 100 μM stock solutions and mixed working solutions at −20° C.

5. Reaction Mix (final volume is 20 μL):

|  | Mix | Final Concentration |
|---|---|---|
| 1 μM Template DNA | 1.0 μL | 50 nM |
| 10 μM Extension Primer | 1.0 μL | 500 nM |
| 5× Reaction Buffer | 4.0 μL | 1× |
| 25 μM Dye-ddNTPs | 0.05 μL | 62.5 nM |
| Thermo Sequenase/AmpliTaq FS | 0.025 μL/0.1 μL | 0.8 U/20 μL |
| Water | 13.925μL/13.85 μL |  |

6. Primer Extension Reaction:

One cycle of 95° C. for 2 min, followed by 35 cycles of 94° C. 15 sec and 55° C./60° C. for 30 sec. (The annealing temperature depends on the melting temperature $T_M$ of the extension primer; the polymerase is active at both temperatures for extension.) We have also had good success for annealing at as low as 45° C.

7. Detection:

Following reaction, samples can be read on the Analyst™ (or other suitable light detection device). Samples may be read directly in the PCR plate or in a microplate or other sample holder following transfer. For two or more dyes, it may be preferable to use a 50-50 beamsplitter or a multichroic beamsplitter, or to switch manually or automatically between two or more dichroic beamsplitters, rather than using a single dichroic beamsplitter.

Recommended Analyst™ Settings:

| Lamp | Continuous |
|---|---|
| Excitation side | Top |
| Excitation Polarizer | s |
| Dynamic Polarizer | Emission |
| Units | counts/second |
| Attenuator | out |
| Integration time | 100,000 microseconds |
| Reads per well | 1 |
| Z Height | 3 mm |
| PMT | Comparator, Sensitivity = 2 |

8. Replicate samples are recommended initially for evaluation of the technology and instrument.
9. Replicate buffer-only wells (without dye-ddNTPs) are useful for background readings.

B. Comments
1. Ideally, the average polarization of luminophores incorporated into extension primers should be 70 mP or larger than the average polarization of free luminophores for reliable interpretation. In addition, ideally, the standard deviation of replicate samples should be less than 10 microplate, indicating reproducibility of the procedure/technique and stability of the instrument. The most accurate measurement will be obtained following high incorporation of the free ddNTPs; with an efficiency $\geq 50\%$. Therefore, it is preferable to use conditions that ensure the near depletion of free ddNTPs in the primer-extension reaction. For initial evaluation and assay optimization, it is helpful to quantify the incorporation efficiency by running the reaction mixture on a sequencer in parallel.
2. Background subtraction is helpful, especially when the signal-to-background is low (<5). Background subtraction was especially helpful for BDF-ddATP; in one experiment, the 8mP for BODIPY Fl-14-ddATP was increased from 50 mP to 130 mP by subtracting buffer background from the raw signals prior to calculating mP. However, background subtraction was less helpful for R6G-ddUTP, where quenching of intensity occurs Upon incorporation. In addition, it is helpful to include buffer wells without any labels in the assay development stage to monitor the background signals.
3. The length of the extension primer may not contribute significantly to the magnitude of the polarization as long as the extension primer is equal to or longer than about 20 nucleotides. In particle, 20-, 22-, and 25-mers were used for primer extension without significant differences in mP changes. Instead, appropriate cycling conditions should be chosen to ensure efficient annealing of the extension primer onto the template.
4. There may be reproducible signal spillover Among different labels, for example, BDF into R6G; R6G into TAMRA; and TAMRA into ROX. However, this effect will be systematic, so that it should not interfere with data interpretation. In particular, data for a given genotype will be affected in the same way in each experiment, so that data still can be binned according to the combination of bases (e.g., A/A, A/C, or C/C), as shown in FIG. 4.
5. Theoretically, the same polarization should be obtained using a "No DNA Control" as using the "wrong" template. However, polarization differences between the two measurements have been observed, sometimes as large as 20 mP. Regardless, this difference is not significant enough to mistake for a "true" positive, because changes in polarization for the positive controls are routinely >50 mP. This potentially can be attributed to nonspecific incorporation, especially if the extension primer forms a hairpin structure on itself. This generally does not appear to be a significant problem; however, if it is a problem, an extension primer can be designed from the reverse direction.

6. We have not observed a performance difference between the two polymerases listed above for the extension reaction in our model system. There may be additional sequenases available for testing in the future that will better incorporate the unnatural dye-labeled ddNTPs.
7. Black and clear 96- or 384-well plates can be used without significant compromise in signal intensity. Clear plates can be stacked in the stacker and registered by the stacker's plate sensor. Black PCR plates are stackable in the magazines. However, to be detected by the plate sensor on the Analyst™ detection platform, a 1 cm×0.5 cm opaque is required near the center of the plate's short edge facing the instrument. A suitable opaque area may be produced using paint or a barcode sticker, among others. Unfortunately, current MJ™ 96-well PCR plates expand after thermocycling and may be caught in the instrument's stacker.

C. Sample Data Using ApoE112 Synthetic Templates

Four replicas were run for each template and measured for incorporation of each dye with the respective filter combinations. Consistent mP increases are observed when complementary templates are present.

| Template | No DNA | C | A | T | G |
|---|---|---|---|---|---|
| | | BDF-ddATP | | | |
| | 67 | 80 | 71 | 124 | 88 |
| | 73 | 82 | 68 | 151 | 84 |
| | 85 | 79 | 78 | 129 | 90 |
| | 79 | 78 | 75 | 133 | 95 |
| Average | 76 | 80 | 73 | 134 | 89 |
| | | Tamra-ddCTP | | | |
| | 40 | 60 | 75 | 51 | 121 |
| | 47 | 55 | 76 | 56 | 111 |
| | 50 | 57 | 71 | 54 | 129 |
| | 48 | 53 | 71 | 51 | 124 |
| Average | 46 | 56 | 73 | 53 | 121 |
| | | R6G-ddUTP | | | |
| | 39 | 50 | 96 | 48 | 44 |
| | 43 | 37 | 92 | 50 | 44 |
| | 45 | 46 | 101 | 47 | 43 |
| | 46 | 38 | 94 | 43 | 49 |
| Average | 43 | 43 | 96 | 47 | 45 |
| | | ROX-ddGTP | | | |
| | 73 | 179 | 82 | 92 | 93 |
| | 68 | 182 | 86 | 104 | 94 |
| | 73 | 172 | 87 | 93 | 101 |
| | 71 | 175 | 83 | 77 | 102 |
| Average | 71 | 177 | 85 | 92 | 98 |

EXAMPLE 2

SNPs Genotyping Assay Employing PCR-Amplified Genomic DNA

A. Experimental Procedure
I. PCR Amplification
  1. Reaction Mixture (Volume=10 μL)

| | Make-up Solution | Final Concentration |
|---|---|---|
| 10× PCR Gold Buffer | 1 μL | 1x |
| 25 mM MgCl₂ | 1 μL | 2.5 mM |
| 2.5 mM dNTPS | 0.1 μL | 25 μM |
| 2.5 μM Primer 1 | 0.2 μL | 100 nM |

-continued

|  | Make-up Solution | Final Concentration |
|---|---|---|
| 2.5 µM Primer 2 | 0.2 µL | 100 nM |
| AmpliTaq Gold (5 U/µL) | 0.2 µL | 1 U/10 µL |
| Genomic DNA (4 ng/µL) | 5 µL | 20 ng |
| Water | to a final volume = 10 µL | |

The above recipe worked well with our amplicons, which had 150–350 base pairs. The quantities of dNTPs and primers used may be reduced without compromising PCR yield; the minimal amount of PCR necessary for an accurate base-calling has not been quantified. Estimates from EtBr-stained agarose gels suggest routine yields of 100 ng/10 µL reaction or more. If bands are invisible on a gel, it will probably be difficult to obtain satisfactory genotyping results.

2. PCR Cycling Conditions:

| a) | Hot Start | 95° C. | 12 min |
|---|---|---|---|
| b) | 15 Cycles | 95° C. | 30 sec |
|  |  | 66° C. | 30 sec |
|  |  |  | −1° C./cycle |
|  |  | 72° C. | 30 sec |
| c) | 30 Cycles | 95° C. | 30 sec |
|  |  | 50° C. | 30 sec |
|  |  | 72° C. | 30 sec |
| d) |  | 72° C. | 6 min |
| e) |  | 4° C. | forever |

We also have used other PCR protocols to amplify some amplicons; the preferred conditions are those that provide the best PCR yield for the gene of interest.

II Primer and dNTP Degradation

1. Add to the PCR mix the following (total addition=10 µL)

|  | Make-up Solution | Final Concentration (in added solution) |
|---|---|---|
| 10× Phosphatase Buffer | 1 µL | 1× |
| Shrimp Alkaline Phosphatase | 2 µL | 2 Units/reaction |
| *E. Coli* Exonuclease I | 0.1 µL | 1 Unit/reaction |
| Water | 6.9 µL | |

2. Incubate at 37° C. for 45 min.
3. Inactivate the enzymes by heating at 95° C. for 15 min.

III. Polarization-based Genotyping Assay

1. Add to the enzymatically treated PCR product the following (total addition=10 µL).

|  | Make-up Solution | Final Concentration (in added solution) |
|---|---|---|
| 5× Reaction Buffer | 2 µL | 1× |
| 10 µM Extension Prirner | 1 µL | 1 µM |
| 25 µM Dye-Labeled ddNTPs | 0.05 µL | 125 nM |
| AmpliTaq, FS/Thermosequenase |  | 0.8 Unit (reaction |
| Water |  | Final volume → 10 µL |

2. Alternative protocols have also been tested with good results, such as the one listed below.

|  | Above Protocol | Alternative Protocol |
|---|---|---|
| 5× Reaction Buffer | 1× | 1× |
| 10 µM Extension Primer | 1 µM | 2.5 µM |
| 25 µM Dye-Labeled ddNTPs | 125 nM | 62.5 nM |
| AmpliTaq, FS/Thermosequenase | 0.8 Unit/reaction | 0.8 Unit/reaction |

Note: Using less label reduces the cost and increases the efficiency of incorporation; however, it also compromises the luminescence intensity. Out of the four luminophores we are currently using, BDF is routinely the weakest. Using the reduced label may require background subtraction for BDF, especially if the signal-to-noise ratio will be below 5:1. Alternatively, BDF can be mixed with half of the concentration of all other luminophores.

2. Primer Extension, or use conditions that best suit the extension primer.

| a) | Hot Start | 94° C. | 1 min |
|---|---|---|---|
| b) | 35 Cycles | 94° C. | 10 sec |
|  |  | 55° C. | 30 sec |

IV. Polarization Measurement

Please see above in the Synthetic Template section.

B. Comments

1. Different extension primers will have different mP values. This complication can be easily resolved by a clustering algorithm and setting positive and negative controls.
2. Successful PCR from Genomic DNA is important. Although our experiments with various synthetic template concentrations indicate that the polarization-based genotyping method can tolerate some variability in PCR yield, the quality of PCR in a high-throughput environment will affect the genotyping results.
3. To evaluate the efficiency of dye-ddNTP incorporation, parallel samples may be run on a sequencer as assay conditions are optimized.
4. Complete removal of dNTPs and PCR primers from the PCR reaction also is important. To monitor the degree of enzymatic digestion, a control may be used in which extension primer is omitted in the last primer-extension step. Without the extension primer, any increase in polarization should reflect residual PCR primers from incomplete enzymatic digestion.

2. Description of Selected Luminescence Assay

Luminescence is the emission of light from excited electronic states of luminescent atoms or molecules, as described above. Luminescence generally refers to all kinds of light emission, except incandescence, and may include photoluminescence, chemiluminescence, and electrochemiluminescence, among others. In photoluminescence, including fluorescence and phosphorescence, the excited electronic state is created by the absorption of electromagnetic radiation. In chemiluminescence, which includes bioluminescence, the excited electronic state is created by a transfer of chemical energy. In electrochemiluminescence, the excited electronic state is created by an electrochemical process. In this application, without limitation, photoluminescence may be used interchangeably with luminescence and fluorescence, and luminophore may be used interchangeably with fluorophore.

Here, luminescence is emitted by luminophores associated with the terminator or other base incorporated during the assay. Luminophores may have short (01–10 nanosecond) or long (10 nanosecond-1+second) luminescence lifetimes and be intrinsic or extrinsic to the terminator. Typically, such luminophores will be extrinsic, such as cyanine dyes, phenanthridines (such as ethidium bromide), acridines (such as acridine orange), indoles (such as DAPI), imidazoles, psoralens, and luminescent metal-ligand and lanthanide complexes and clyptates, among others. Additional luminophores are listed in Richard P. Haugland, *Handbook of Fluorescent Probes and Research Chemicals* ($6^{th}$ ed. 1996), which is incorporated herein by reference. Extrinsic luminophores may be associated with the polynucleotides covalently or noncovalently. Luminophores may be associated covalently using various reactive groups, especially if amines or thiols are incorporated into the nucleotides during their synthesis. Luminophores may be associated noncovalently via specific binding pairs, such as avidin and biotin, protein A and immunoglobulins, and lectins and sugars (e.g., concanavalin A and glucose). Luminophores also may be associated noncovalently by intercalating into the polynucleotide or by binding to grooves in the polynucleotide, if they so associate only after incorporation of the terminator.

Luminophores may be used in a variety of luminescence assays, including fluorescence polarization (FP), fluorescence resonance energy transfer (FRET), fluorescence lifetime (FLT), total internal reflection (TIR) fluorescence, fluorescence correlation spectroscopy (FCS), and fluorescence recovery after photobleaching (FRAP), as well as their phosphorescence and higher-transition analogs, among others.

The remainder of this section is divided into four sections: (A) intensity assays, (B) polarization assays, (C) energy transfer assays, and (D) time-resolved assays.

A. Intensity Assays

Luminescence intensity assays involve monitoring the intensity (or amount) of light emitted from a composition. The intensity of emitted light will depend on the extinction coefficient, quantum yield, and number of luminophores in the composition, among others. These quantities, in turn, will depend on the environment of the luminophore, including the proximity and efficacy of quenchers and energy transfer partners. Thus, luminescence intensity assays may be used to study binding reactions, among other applications.

B. Polarization Assays

Luminescence polarization assays involve monitoring the intensity of polarized light emitted from a composition. (Polarization describes tie direction of light's electric field, which generally is perpendicular to the direction of light's propagation.) Luminescence polarization assays may be homogeneous and ratiometric, making them relatively insensitive to sample-to-sample variations in concentration, volume, and meniscus shape.

Figure 5:
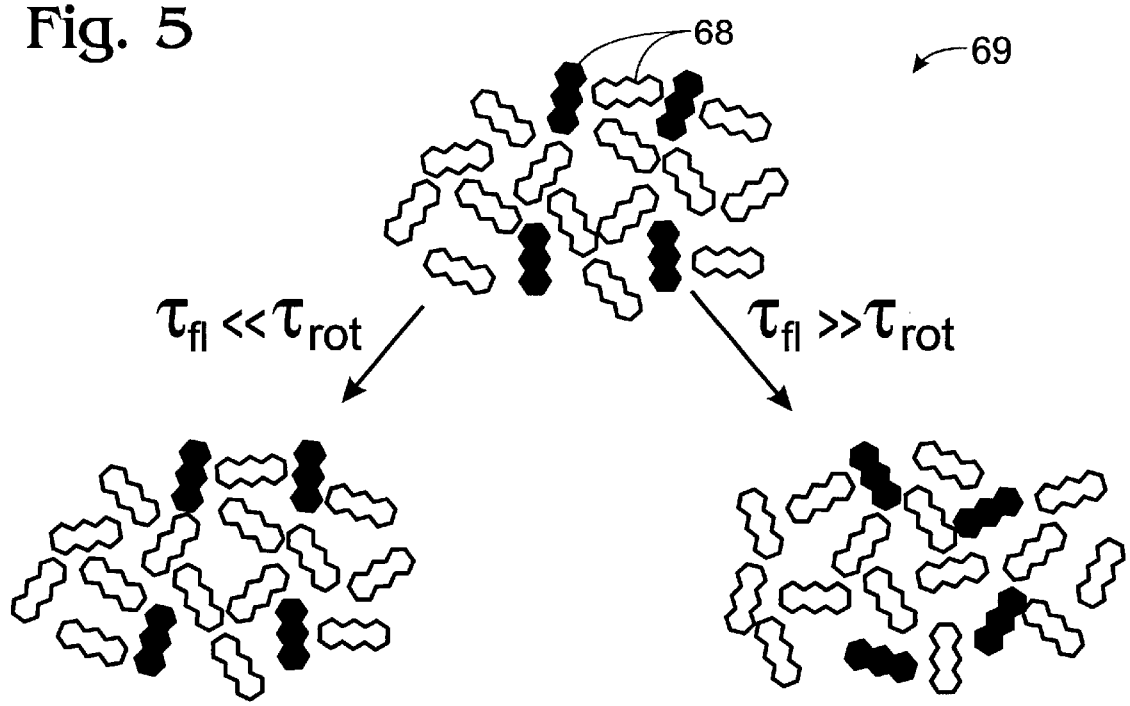
FIG. 5 is a schematic view of luminescently labeled molecules, showing how molecular reorientation affects luminescence polarization.

Luminescence polarization assays typically are used to study molecular rotation. FIG. 5 shows how luminescence pollution is affected by molecular rotation. In a luminescence polarization assay, specific molecules 65 within a composition 66 are labeled with one or more luminophores. The composition then is illuminated with polarized excitation light, which preferentially excites luminophores having absorption dipoles aligned parallel to the polarization of the excitation light. These molecules subsequently decay by preferentially emitting light polarized parallel to their emission dipoles. The extent of polarization of the total emitted light depends on the extent of molecular reorientation during the time interval between luminescence excitation and emission, which is termed the luminescence lifetime, $\tau$. In turn, the extent of molecular reorientation depends on the luminescence lifetime and the size, shape, and environment of the reorienting molecule. Thus, luminescence polarization assays can be used to quantify hybridization/biding reactions and enzymatic activity, among other applications. In particular, molecules commonly rotate via diffusion with a rotational correlation time $\tau_{rot}$ that is proportional to their size. Thus, during their luminescence lifetime, relatively large molecules will not reorient significantly, so that their total luminescence will be relatively polarized. In contrast, during the same time interval, relatively small molecules will reorient significantly, so that their total luminescence will be relatively unpolarized.

The relationship between polarization and intensity is expressed by the following equation:

$$P = \frac{I_{\parallel} - I_{\perp}}{I_{\parallel} + I_{\perp}} \quad (1)$$

Here, P is the polarization, $I_{\parallel}$ is the intensity of luminescence polarized parallel to the polarization of the excitation light, and $I_{195}$ is the intensity of luminescence polarized perpendicular to the polarization of the excitation light. P generally varies from zero to one-half for randomly oriented molecules (and zero to one for aligned molecules). If there is little rotation between excitation and emission, $I_{\parallel}$ will be relatively large, $I_{\perp}$ will be relatively small, and P will be close to one-half. (P may be less than one-half even if there is no rotation; for example, P will be less than one if the absorption and emission dipoles are not parallel.) In contrast, if there is significant rotation between absorption and emission, $I_{\parallel}$ will be comparable to $I_{\perp}$, and P will be close to zero. Polarization often is reported in milli-P (mP) units (1000×P), which for randomly oriented molecules will range between 0 and 500, because P will range between zero and one-half.

Polarization also may be described using other equivalent quantities, such as anisotropy. The relationship between anisotropy and intensity is expressed by the following equation;

$$r = \frac{I_{\parallel} - I_{\perp}}{I_{\parallel} + 2I_{\perp}} \quad (2)$$

Here, r is the anisotropy. Polarization and anisotropy include the same information, although anisotropy may be more simply expressed for systems containing more than one luminophore. In the description and claims that follow, these terms may be used interchangeably, and a generic reference to one should be understood to imply a generic reference to the other.

The relationship between polarization, luminescence lifetime, and rotational correlation time is expressed by the Perrin equation:

$$\left(\frac{1}{P} - \frac{1}{3}\right) = \left(\frac{1}{P_0} - \frac{1}{3}\right) \cdot \left(1 + \frac{\tau}{\tau_{rot}}\right) \quad (3)$$

Here, $P_0$ is the polarization in the absence of molecular motion (intrinsic polarization), $\tau$ is the luminescence lifetime (inverse decay rate) as described above, and $\tau_{rot}$ is the rotational correlation time (inverse rotational rate) as described above.

The Perrin equation shows that luminescence polarization assays are most sensitive when the luminescence lifetime and the rotational correlation time are similar. Rotational correlation time is proportional to molecular weight, increasing by about 1 nanosecond for each 2,400 Dalton increase in molecular weight (for a spherical molecule). For shorter lifetime luminophores, such as fluorescein, which has a luminescence lifetime of roughly 4 nanoseconds, luminescence polarization assays are most sensitive for molecular weights less than about 40,000 Daltons. For longer lifetime probes, such as Ru(bpy)$_2$dcbpy (ruthenium 2,2'-dibipyridyl 4,4'-dicarboxyl-2,2'-bipyridine), which has a lifetime of roughly 400 nanoseconds, luminescence polarization assays are most sensitive for molecular weights between about 70,000 Daltons and 4,000,000 Daltons.

C. Energy Transfer Assays

Energy transfer is the transfer of luminescence energy from a donor luminophore to an acceptor without emission by the donor. In energy transfer assays, a donor luminophore is excited from a ground state into an excited state by absorption of a photon. If the donor luminophore is sufficiently close to an acceptor, excited-state energy may be transferred from the donor to the acceptor, causing donor luminescence to decrease and acceptor luminescence to increase (if the acceptor is luminescent). The efficiency of this transfer is very sensitive to the separation R between donor and acceptor, decaying as $1/R^{-6}$. Energy transfer assays use energy transfer to monitor the proximity of donor and acceptor, which in turn may be used to monitor the presence or activity of an analyte, among others.

Energy transfer assays may focus on an increase in energy transfer as donor and acceptor are brought into proximity. These assays may be used to monitor binding, as between two molecules X and Y to form a complex X:Y. Here, colon (:) represents a noncovalent interaction In these assays, one molecule is labeled with a donor D, and the other molecule is labeled with an acceptor A, such that the interaction between X and Y is not altered appreciably. Independently, D and A may be covalently attached to X and Y, or covalently attached to binding partners of X and Y.

Energy transfer assays also may focus on a decrease in energy transfer as donor and acceptor are separated. These assays may be used to monitor cleavage, as by hydrolytic digestion of doubly labeled substrates (peptides, nucleic acids). In one application, two portions of a polypeptide are labeled with D and A, so that cleavage of the polypeptide by a protease such as an endopeptidase will separate D and A and thereby reduce energy transfer. In another application, two portions of a nucleic acid are labeled with D and A, so that cleave by a nuclease such as a restriction enzyme will separate D and A and thereby reduce energy transfer.

Energy transfer between D and A may be monitored in various ways. For example, energy transfer may be monitored by observing an energy-transfer induced decrease in the emission intensity of D and increase in the emission intensity of A (if A is a luminophore). Energy transfer also may be monitored by observing an energy-transfer induced decrease in the lifetime of D and increase in the apparent lifetime of A.

In a preferred mode, a long-lifetime luminophore is used as a donor, and a short-lifetime luminophore is used as an acceptor. Suitable long-lifetime luminophores include metal-ligand complexes containing ruthenium, osmium, etc., and lanthanide chelates containing europium, terbium, etc. In time-gated assays, the donor is excited using a flash of light having a wavelength near the excitation maximum of D. Next, there is a brief wait, so that electronic transients and/or short-lifetime background luminescence can decay. Finally, donor and/or acceptor luminescence intensity is detected and integrated. In frequency-domain assays, the donor is excited using time-modulated light, and the phase and/or modulation of the donor and/or acceptor emission is monitored relative to the phase and/or modulation of the excitation light. In both assays, donor luminescence is reduced if there is energy transfer, and acceptor luminescence is observed only if there is energy transfer.

D. Steady-State Versus Time-Resolved Assays

Apparatus 70, 90, and 160 may be used to conduct a variety of steady-state and time-resolved luminescence assays. Steady-state assays measure luminescence under constant illumination, using the continuous light source. Time-resolved assays measure luminescence as a function of time, using either the continuous light source, with its intensity appropriately modulated, or the time-varying light source. Time-resolved assays may be conducted in the time domain or in the frequency domain, both of which are functionally equivalent.

In a time-domain measurement, the time course of luminescence is monitored directly. Typically, a composition containing a luminescent analyte is illuminated using a narrow pulse of light, and the time dependence of the intensity of the resulting luminescence emission is observed, although other protocols also may be used. For a simple molecule, the luminescence commonly follows a single-exponential decay.

In a frequency-domain measurement, the time course of luminescence is monitored indirectly, in frequency space. Typically, the composition is illuminated using light whose intensity is modulated sinusoidally at a single modulation frequency $f$, although other protocols (such as transforming time-domain data into the frequency domain) also may be used. The intensity of the resulting luminescence emission is modulated at the same frequency as the excitation light. However, the emission will lag the excitation by a phase angle (phase) $\phi$, and the intensity of the emission will be demodulated relative to the intensity of the excitation by a demodulation factor (modulation) M.

Figure 6:
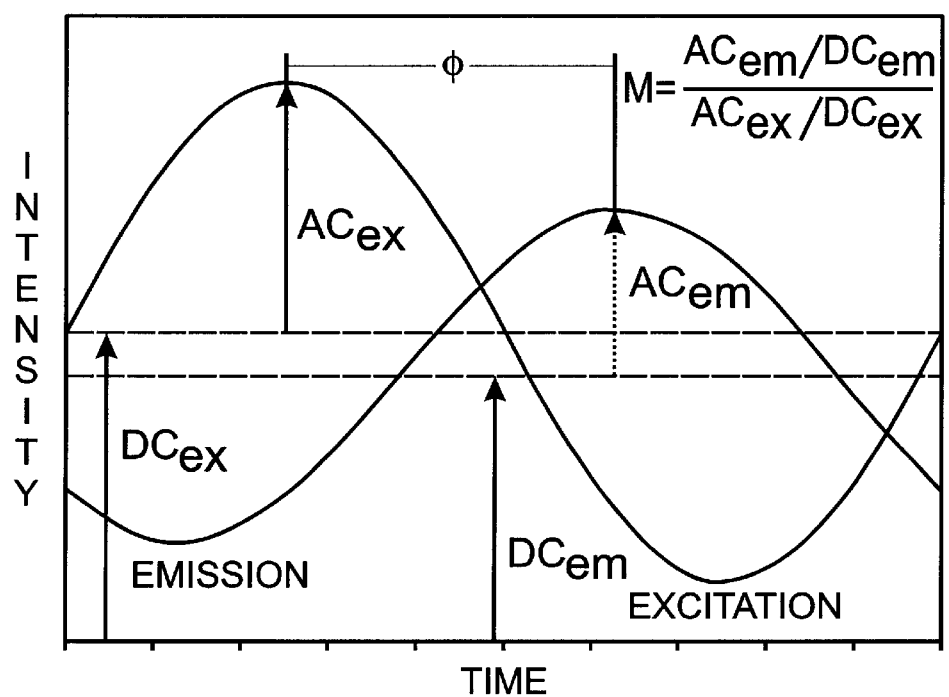
FIG. 6 is a schematic view of a frequency-domain time-resolved measurement, showing the definitions of phase angle chase) φ and demodulation factor (modulation) M.

FIG. 6 shows the relationship between emission and excitation in a single-frequency-domain experiment. The phase $\phi$ is the phase difference between the excitation and emission. The modulation M is the ratio of the AC amplitude to the DC offset for the emission, relative to the ratio of the AC amplitude to the DC offset for the excitation. The phase and modulation are related to the luminescence lifetime τ by the following equations:

$$\omega\tau = \tan(\phi)$$

$$\omega\tau = \sqrt{\frac{1}{M^2} - 1} \tag{5}$$

Here ω is the angular modulation frequency, which equals $2\pi$ times the modulation frequency. For maximum sensitivity, the angular modulation frequency should be roughly the inverse of the luminescence lifetime. Lifetimes of interest in high-throughput screening vary from less than 1 nanosecond to greater than 1 millisecond. Therefore, instruments for high-throughput screening should be able to cover modulation frequencies from less than about 200 Hz to greater than about 200 MHz.

3. Description of Luminescence Apparatus

FIGS. 7–13 show apparatus 70, 90, 260 for detecting light transmitted from a composition. These apparatus may include a variety of components, some or all of which may be used in any given assay. These components include (1) a stage for supporting the composition, (2) one or more light sources for delivering light to a composition, (3) one or more detectors for receiving light transmitted from the composition and converting it to a signal, (4) first and second optical relay structures for relaying light between the light source, composition, and detector, and (5) a processor for analyzing the signal from the detector. These apparatus can be used for a variety of assays, including but not limited to the assays described above. Components of the optical system can be chosen to optimize sensitivity and dynamic range for each assay supported by the apparatus. Toward this end, optical components with low intrinsic luminescence are preferred. In addition, some components may be shared by different modes, whereas other components may be unique to a particular mode. For example, in apparatus 90 and 260, absorbance, scattering, photoluminescence intensity and steady-state photoluminescence polarization modes share a light source; time-resolved absorbance and luminescence modes use their own light source; and chemiluminescence modes do not use a light source. Similarly, photoluminescence and chemiluminescence modes use different detectors.

A. Apparatus 70

Figure 7:
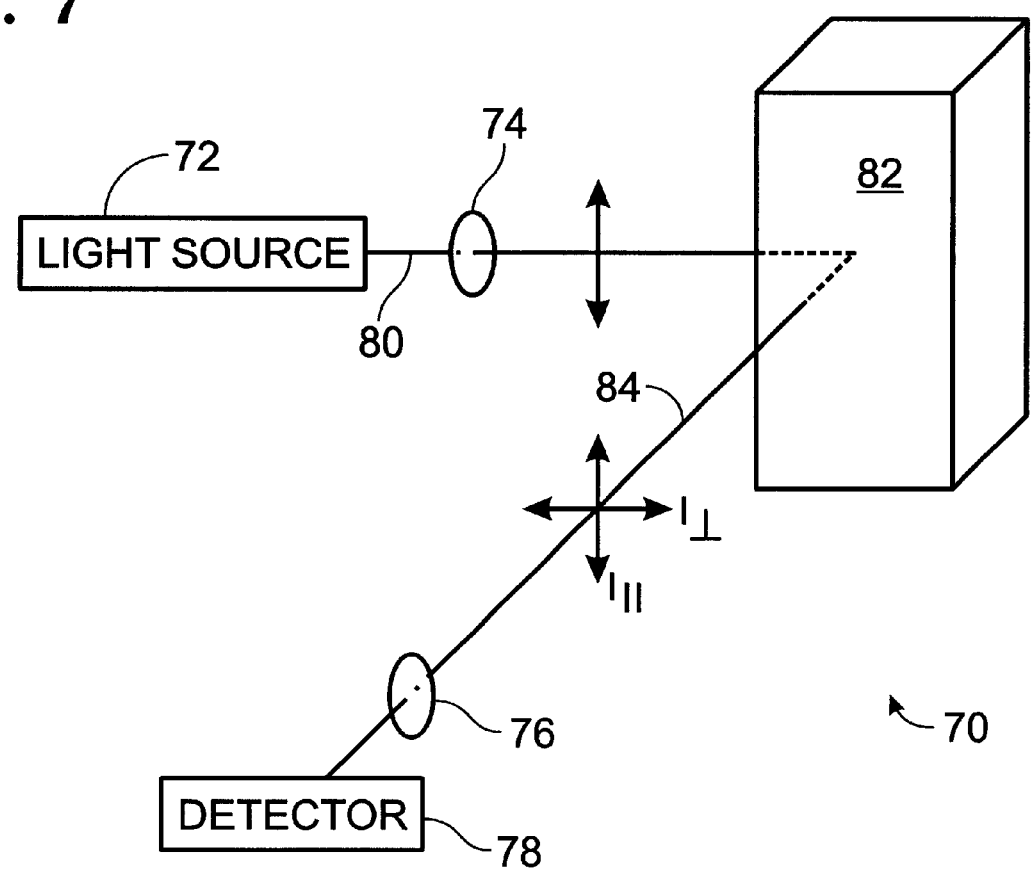
FIG. 7 is a schematic view of an apparatus for detecting light in accordance with the invention.

FIG. 7 shows an apparatus 70 for detecting light (especially polarized light) transmitted from a composition. Apparatus 70 includes a light source 72, an excitation polarizer 74, an emission polarizer 76, and a detector 78. Light 80 produced by light source 72 is directed through excitation polarizer 74, which passes polarized excitation light (indicated by vertical arrow). Polarized excitation light is directed onto a sample 82, which emits light 84 in response. The emitted light may be either some fraction of the incident light or luminescence. Emitted light 84 is directed through emission polarizer 76, S which may have components oriented parallel (∥; indicated by vertical arrow) or perpendicular (⊥; indicated by horizontal arrow) to the polarization of excitation light 80. Depending on its orientation, emission polarizer 76 passes parallel ($I_{\parallel}$) or perpendicular ($I_{\perp}$) components of emission light 84 for detection by detector 78.

B. Apparatus 90

FIGS. 8–12 show an alternative apparatus 90 for detecting light transmitted from a composition. This apparatus includes (i) a photoluminescence optical system, (ii) a chemiluminescence optical system, and (iii) a housing.

Figure 8:
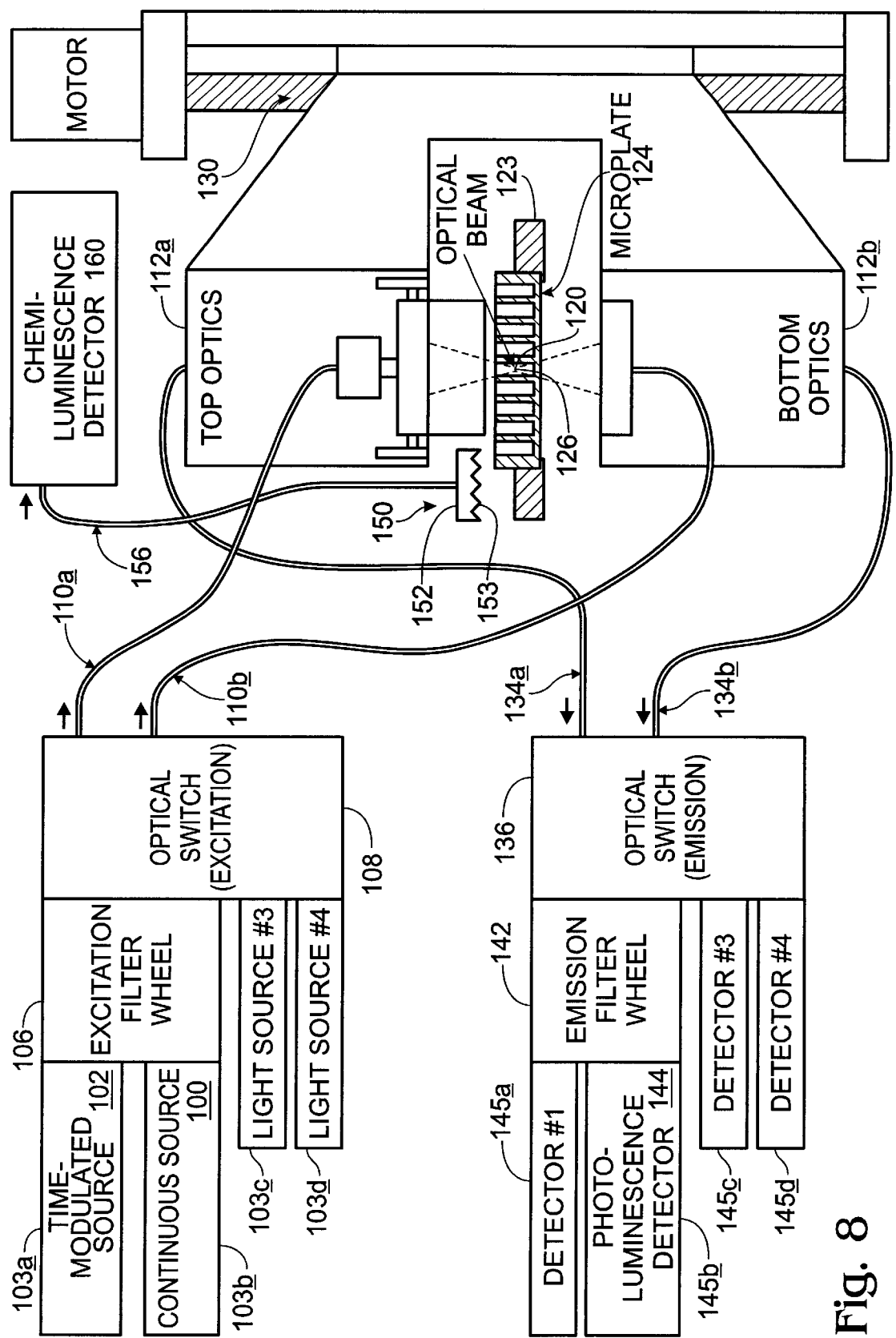
FIG. 8 is a schematic view of an alternative apparatus for detecting light in accordance with the invention.
Figure 9:
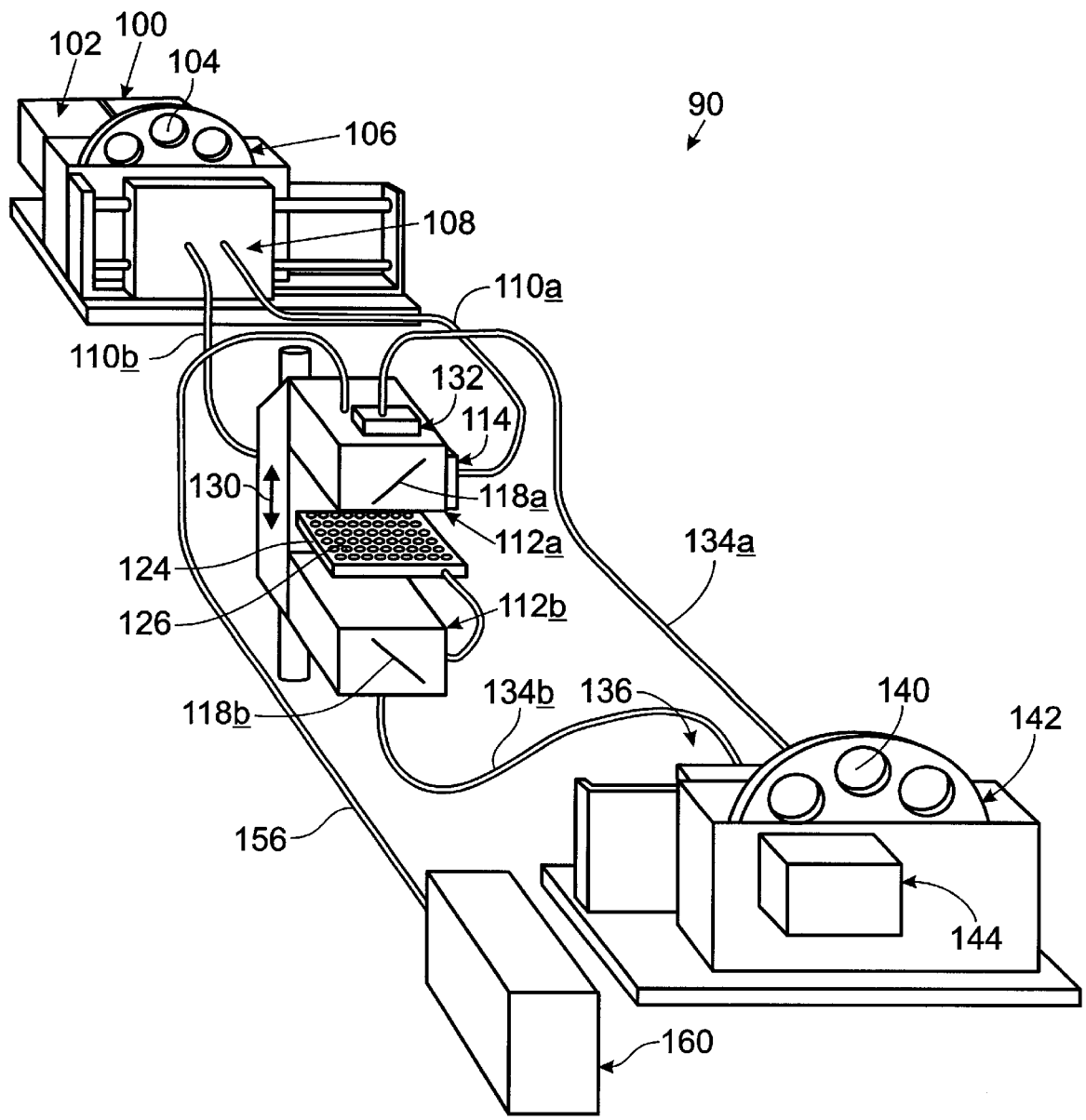
FIG. 9 is a partially schematic perspective view of the apparatus of FIG. 8.
Figure 10:
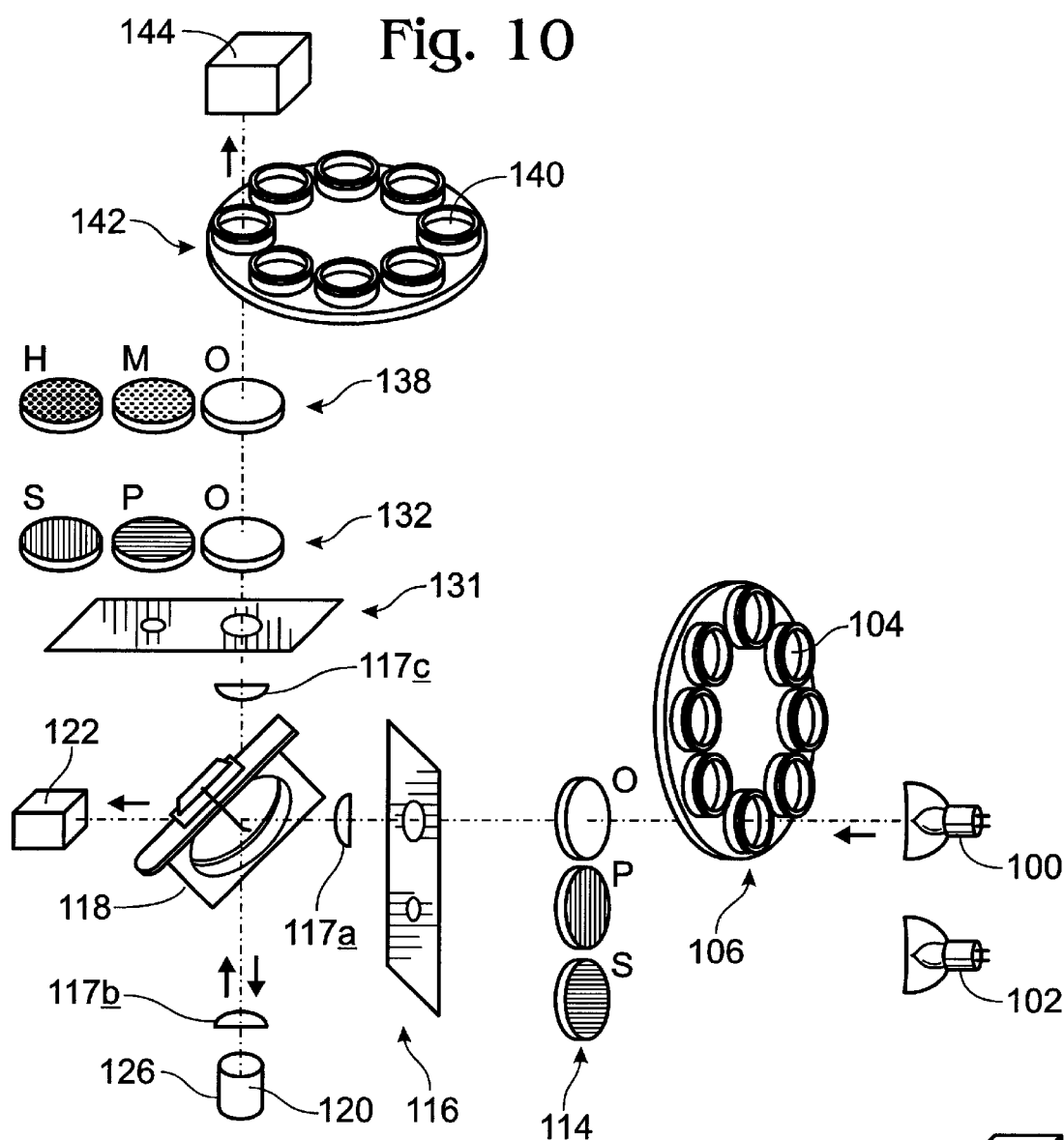
FIG. 10 is a schematic view of photoluminescence optical components from the apparatus of FIG. 8.

Photoluminescence Optical System. FIGS. 8–10 show the photoluminescence (or incident light-based) optical system of apparatus 90. As configured here, apparatus 90 includes a continuous light source 100 and a time-modulated light source 102. Apparatus 90 includes light source slots 103a–d for four light sources, although other numbers of light source slots and light sources also could be provided. Light source slots 103a–d function as housings that may surround at least a portion of each light source, providing some protection from radiation and explosion. The direction of light transmission through the incident light-based optical system is indicated by arrows.

Continuous source 100 provides light for absorbance, scattering, photoluminescence intensity, and steady-state photoluminescence polarization assays. Continuous light source 100 may include arc lamps, incandescent lamps, fluorescent lamps, electroluminescent devices, lasers, laser diodes, and light-emitting diodes (LEDs), among others. A preferred continuous source is a high-intensity, high color temperature xenon arc lamp, such as a Model LX175F CERMAX xenon lamp from ILC Technology, Inc. Color temperature is the absolute temperature in Kelvin at which a blackbody radiator must be operated to have a chromaticity equal to that of the light source. A high color temperature lamp produces more light than a low color temperature lamp, and it may have a maximum output shifted toward or into visible wavelengths and ultraviolet wavelengths where many luminophores absorb. The preferred continuous source has a color temperature of 5600 Kelvin, greatly exceeding the color temperature of about 3000 Kelvin for a tungsten filament source. The preferred source provides more light per unit time than flash sources, averaged over the flash source duty cycle, increasing sensitivity and reducing read times. Apparatus 90 may include a modulator mechanism configured to vary the intensity of light incident on the composition without varying the intensity of light produced by the light source.

Time-modulated source 102 provides light for time-resolved absorbance and/or photoluminescence assays, such as photoluminescence lifetime and time-resolved photoluminescence polarization assays. A preferred time-modulated source is a xenon flash lamp, such as a Model FX-1160 xenon flash lamp from EG&G Electro-Optics. The preferred source produces a "flash" of light for a brief interval before signal detection and is especially well suited for time-domain measurements. Other time-modulated sources include pulsed lasers, electronically modulated lasers and LEDs, and continuous lamps and other sources whose intensity can be modulated extrinsically using a Pockets cell, Kerr cell, or other mechanism. Such other mechanisms may include an amplitude modulator such as a chopper as described in U.S. Provisional Patent Application No. 60/094,276, which is incorporated herein by reference. Extrinsically modulated continuous light sources are especially well suited for frequency-domain measurements.

In apparatus 90, continuous source 100 and time-modulated source 102 produce multichromatic, unpolarized, and incoherent light. Continuous source 100 produces substantially continuous illumination, whereas time-modulated source 102 produces time-modulated illumination. Light from these light sources may be delivered to the sample without modification, or it may be filtered to alter its intensity, spectrum, polarization, or other properties.

Light produced by the light sources follows an excitation optical path to an examination site or measurement region. Such light may pass through one or more "spectral filters," which generally comprise any mechanism for altering the spectrum of light that is delivered to the sample. Spectrum refers to the wavelength composition of light. A spectral filter may be used to convert white or multichromatic light, which includes light of many colors, into red, blue, green, or other substantially monochromatic light, which includes light of one or only a few colors. In apparatus 90, spectrum is altered by an excitation interference filter 104, which preferentially transmits light of preselected wavelengths and preferentially absorbs light of other wavelengths. For convenience, excitation interference filters 104 may be housed in an excitation filter wheel 106, which allows the spectrum of excitation light to be changed by rotating a preselected filter into the optical path. Spectral filters also may separate light spatially by wavelength. Examples include gratings, monochromators, and prisms.

Spectral filters are not required for monochromatic ("single color") light sources, such as certain lasers, which output light of only a single wavelength. Therefore, excitation filter wheel 106 may be mounted in the optical path of some light source slots 103a,b, but not other light source slots 103c,d. Alternatively, the filter wheel may include a blank station that does not affect light passage.

Light next passes through an excitation optical shuttle (or switch) 108, which positions an excitation fiber optic cable 110a,b in front of the appropriate light source to deliver light to top or bottom optics heads 112a,b, respectively. Light is transmitted through a fiber optic cable much like water is transmitted through a garden hose. Fiber optic cables can be used easily to turn light around corners and to route light around opaque components of the apparatus. Moreover, fiber optic cables give the light a more uniform intensity profile. A preferred fiber optic cable is a fused silicon bundle, which has low autoluminescence. Despite these advantages, light also can be delivered to the optics heads using other mechanisms, such as mirrors.

Light arriving at the optics head may pass through one or more excitation "polarization filter," which generally comprise any mechanism for altering the polarization of light. Excitation polarization filters may be included with the top and/or bottom optics head. In apparatus 90, polarization is altered by excitation polarizers 114, which are included only with top optics head 112a for top reading; however, such polarizers also can be included with bottom optics head 112b for bottom reading. Excitation polarization filters 114 may include an s-polarizer S that passes only s-polarized light, a p-polarizer P that passes only p-polarized light, and a blank O that passes substantially all light, where polarizations are measured relative to the beamsplitter. Excitation polarizers 114 also may include a standard or ferro-electric liquid crystal display (LCD) polarization switching system. Such a system may be faster than a mechanical switcher. Excitation polarizers 114 also may include a continuous mode LCD polarization rotator with synchronous detection to increase the signal-to-noise ratio in polarization assays. Excitation polarizers 114 may be incorporated as an inherent component in some light sources, such as certain lasers, that intrinsically produce polarized light.

Light at one or both optics heads also may pass through an excitation "confocal optics element," which generally comprises any mechanism for focusing light into a "sensed volume." In apparatus 90, the confocal optics element includes a set of lenses 117a–c and an excitation aperture 116 placed in an image plane conjugate to the sensed volume, as shown in FIG. 10. Aperture 116 may be implemented directly, as an aperture, or indirectly, as the end of a fiber optic cable. Preferred apertures have diameters of 1 mm and 1.5 mm. Lenses 117a,b project an image of aperture 116 onto the sample, so that only a preselected or sensed volume of the sample is illuminated. The area of illumination will have a diameter corresponding to the diameter of the excitation aperture.

Light traveling through the optics heads is reflected and transmitted through a beamsplitter 118, which delivers reflected light to a composition 120 and transmitted light to a light monitor 122. Reflected and transmitted light both pass through lens 117b, which is operatively positioned between beamsplitter 118 and composition 120.

Beamsplitter 118 is used to direct excitation or incident light toward the sample and light monitor, and to direct light leaving the sample toward the detector. The beamsplitter is changeable, so that it may be optimized for different assay modes or compositions. In some embodiments, switching between beamsplitters may be performed manually, whereas in other embodiments, such switching may be performed automatically. Automatic switching may be performed based on direct operator command, or based on an analysis of the sample by the instrument. If a large number or variety of photoactive molecules are to be studied, the beamsplitter must be able to accommodate light of many wavelengths; in this case, a "50:50" beamsplitter that reflects half and transmits half of the incident light independent of wavelength is optimal. Such a beamsplitter can be used with many types of molecules, while still delivering considerable excitation light onto the composition, and while still transmitting considerable light leaving the sample to the detector. If one or a few related photoactive molecules are to be studied, the beamsplitter needs only to be able to accommodate light at a limited number of wavelengths; in this case, a "dichroic" or "multichroic" beamsplitter is optimal. Such a beamsplitter can be designed with cutoff wavelengths for the appropriate sets of molecules and will reflect most or substantially all of the excitation and background light, while transmitting most or substantially all of the emission light in the case of luminescence. This is possible because the beamsplitter may have a reflectivity and transmissivity that varies with wavelength.

Light monitor 122 is used to correct for fluctuations in the intensity of light provided by the light sources. Such corrections may be performed by reporting detected intensities as a ratio over corresponding times of the luminescence intensity measured by the detector to tie excitation light intensity measured by the light monitor. The light monitor also can be programmed to alert the user if the light source fails. A preferred light monitor is a silicon photodiode with a quartz window for low autoluminescence.

The composition (or sample) may be held in a sample holder supported by a stage 123. The composition can include compounds, mixtures, surfaces, solutions, emulsions, suspensions, cell cultures, fermentation cultures, cells, tissues, secretions, and/or derivatives and/or extracts thereof. Analysis of the composition may involve measuring the presence, concentration, or physical properties (including interactions) of a photoactive analyte in such a composition. Composition may refer to the contents of a single microplate well, or several microplate wells, depending on the assay. In some embodiments, such as a portable apparatus, the stage may be intrinsic to the instrument.

The sample holder can include microplates, biochips, or any array of samples in a known format, In apparatus 90, the preferred sample holder is a microplate 124, which includes a plurality of microplate wells 126 for holding compositions. Microplates are typically substantially rectangular holders that include a plurality of sample wells for holding a corresponding plurality of samples. These sample wells are normally cylindrical in shape although rectangular or other shaped wells are sometimes used. The sample wells are typically disposed in regular arrays. The "standard" microplate includes 96 cylindrical sample wells disposed in a 8×12 rectangular array on 9 millimeter centers.

The sensed volume typically has an hourglass shape, with a cone angle of about 25° and a minimum diameter ranging between 0.1 mm and 2.0 mm. For 96-well and 384-well microplates, a preferred minimum diameter is about 1.5 mm. For 1536-well microplates, a preferred minimum diameter is about 1.0 mm. The size and shape of the sample holder may be matched to the size and shape of the sensed volume, as described in PCT Patent application Ser. No. PCT/US99/08410, which is incorporated herein by reference.

The position of the sensed volume can be moved precisely within the composition to optimize the signal-to-noise and signal-to-background ratios. For example, the sensed volume may be moved away from walls in the sample holder to optimize signal-to-noise and signal-to-background ratios, reducing spurious signals that might arise from luminophores bound to the walls and thereby immobilized. In apparatus 90, position in the X,Y-plane perpendicular to the optical path is controlled by moving the stage supporting the composition, whereas position along the Z-axis parallel to the optical path is controlled by moving the optics heads using a Z-axis adjustment mechanism 130, as shown in FIGS. 8 and 9. However, any mechanism for bringing the sensed volume into register or alignment with the appropriate portion of the composition also may be employed.

The combination of top and bottom optics permits assays to combine: (1) top illumination and top detection, or (2) top illumination and bottom detection, or (3) bottom illumination and top detection, or (4) bottom illumination and bottom detection. Same-side illumination and detection, (1) and (4), is referred to as "epi" and is preferred for photoluminescence and scattering assays. Opposite-side illumination and detection, (2) and (3), is referred to as "trans" and has been used in the past for absorbance assays. In apparatus 90, epi modes are supported, so the excitation and emission light travel the same path in the optics head, albeit in opposite or anti-parallel directions. However, trans modes also can be used with additional sensors, as described below. In apparatus 90, top and bottom optics heads move together and shape a common focal plane, However, in other embodiments, top and bottom optics heads may move independently, so that each can focus independently on the same or different sample planes.

Generally, top optics can be used with any sample holder having an open top, whereas bottom optics can be used only wit sample holders having optically transparent bottoms, such as glass or thin plastic bottoms. Clear bottom sample holders are particularly suited for measurements involving analytes that accumulate on the bottom of the holder.

Light is transmitted by the composition in multiple directions. A portion of the transmitted light will follow an emission pathway to a detector. Transmitted light passes through lens 117c and may pass through an emission aperture 131 and/or an emission polarizer 132. In apparatus 90, the emission aperture is placed in an image plane conjugate to the sensed volume and transmits light substantially exclusively from this sensed volume. In apparatus 90, the emission apertures in the top and bottom optical systems are the same size as the associated excitation apertures, although other sizes also may be used. The emission polarizers are included only with top optics head 112a. The emission aperture and emission polarizer are substantially similar to their excitation counterparts. Emission polarizer 132 may be included in detectors that intrinsically detect the polarization of light.

Excitation polarizers 114 and emission polarizers 132 may be used together in nonpolarization assays to reject certain background signals. Luminescence from the sample holder and from luminescent molecules adhered to the sample holder is expected to be polarized, because the rotational mobility of these molecules should be hindered. Such polarized background signals can be eliminated by "crossing" the excitation and emission polarizers, that is, setting the angle between their transmission axes at 90°. As described above, such polarized background signals also can be reduced by moving the sensed volume away from walls of the sample holder. To increase signal level, beamsplitter 118 should be optimized for reflection of one polarization and transmission of the other polarization. This method will work best where the luminescent molecules of interest emit relatively unpolarized light, as will be true for small luminescent molecules in solution.

Transmitted light next passes through an emission fiber optic cable 134a,b to an emission optical shuttle (or switch) 136. This shuttle positions the appropriate emission fiber optic cable in front of the appropriate detector. In apparatus 90, these components are substantially similar to their excitation counterparts, although other mechanisms also could be employed.

Light exiting the fiber optic cable next may pass through one or more emission "intensity filters," which generally comprise any mechanism for reducing the intensity of light. Intensity refers to the amount of light per unit area per unit time. In apparatus 90, intensity is altered by emission neutral density filters 138, which absorb light substantially independent of its wavelength, dissipating the absorbed energy as heat. Emission neutral density filters 138 may include a high-density filter H that absorbs most incident light, a medium-density filter M that absorbs somewhat less incident light, and a blank O that absorbs substantially no incident light. These filters may be changed manually, or they may be changed automatically, for example, by using a filter wheel. Intensity filters also may divert a portion of the light away from the sample without absorption. Examples include beam splitters, which transmit some light along one path and reflect other light along another path, and diffractive beam splitters (e.g., acousto-optic modulators), which deflect light along different paths through diffraction. Examples also include hot mirrors or windows that transmit light of some wavelengths and absorb light of other wavelengths.

Light next may pass through an emission interference filter 140, which may be housed in an emission filter wheel 142. In apparatus 90, these components are substantially similar to their excitation counterparts, although other mechanisms also could be employed. Emission interference filters block stray excitation light, which may enter the emission path through various mechanisms, including reflection and scattering. If unblocked, such stray excitation light could be detected and misidentified as photoluminescence, decreasing the signal-to-background ratio. Emission interference filters can separate photoluminescence from excitation light because photoluminescence has longer wavelengths than the associated excitation light. Luminescence typically has wavelengths between 200 and 2000 nanometers.

The relative positions of the spectral, intensity, polarization, and other filters presented in this description may be varied without departing from the spirit of the invention. For example, filters used here in only one optical path, such as intensity filters, also may be used in other optical paths. In addition, filters used here in only top or bottom optics, such as polarization filters, may also be used in the other of top or bottom optics or in both top and bottom optics. The optimal positions and combinations of filters for a particular experiment will depend on the assay mode and the composition, among other factors.

Light last passes to a detector, which is used in absorbance, scattering and photoluminescence assays. In apparatus 90, there is one detector 144, which detects light from all modes. A preferred detector is a photomultiplier tube (PMT). Apparatus 90 includes detector slots 145a–d for four detectors, although other numbers of detector slots and detectors also could be provided.

More generally, detectors comprise any mechanism capable of converting energy from detected light into signals that may be processed by the apparatus, and by the processor in particular. Suitable detectors include photomultiplier tubes, photodiodes, avalanche photodiodes, charge-coupled devices (CCDs), and intensified CCDs, among others. Depending on the detector, light source, and assay mode, such detectors may be used in a variety of detection modes. These detection modes include (1) discrete (e.g., photon-counting) modes, (2) analog (e.g., current-integration) modes, and/or (3) imaging modes, among others, as described in PCT patent application Ser. No. PCT/US99/03678.

Figure 11:
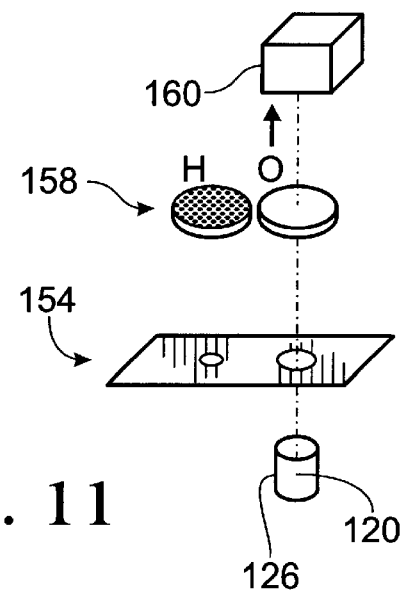
FIG. 11 is a schematic view of chemiluminescence optical components from the apparatus of FIG. 8.

Chemiluminescence optical system. FIGS. 8, 9, and 11 show the chemiluminescence optical system of apparatus 90. Because chemiluminescence follows a chemical event rather than the absorption of light, the chemiluminescence optical system does not require a light source or other excitation optical components. Instead, the chemiluminescence optical system requires only selected emission optical components. In apparatus 70, a separate lensless chemiluminescence optical system is employed, which is optimized for maximum sensitivity in the detection of chemiluminescence.

Generally, components of the chemiluminescence optical system perform the same functions and are subject to the same caveats and alternatives as their counterparts in the incident light-based optical system. The chemiluminescence optical system also can be used for other assay modes that do not require illumination, such as electrochemiluminescence.

The chemiluminescence optical path begins with a chemiluminescent composition 120 held in a sample holder 126. The composition and sample holder are analogous to those used in photoluminescence assays; however, analysis of the composition involves measuring the intensity of light generated by a chemiluminescence reaction within the composition rather than by light-induced photoluminescence. A familiar example of chemiluminescence is the glow of the firefly.

Chemiluminescence light typically is transmitted from the composition in all directions, although most will be absorbed or reflected by the walls of the sample holder. A portion of the light transmitted through the top of the well is collected using a chemiluminescence head 150, as shown in FIG. 8, and will follow a chemiluminescence optical pathway to a detector. The direction of light transmission through tho chemilumimescence optical system is indicated by a rows.

The chemiluminescence head includes a nonconfocal mechanism for transmitting light from a sensed volume within the composition. Detecting from a sensed volume reduces contributions to the chemiluminescence signal resulting from "cross talk," which is pickup from neighboring Wells. The nonconfocal mechanism includes a chemiluminescence baffle 152, which includes rugosities 153 that absorb or reflect light from other wells. The nonconfocal mechanism also includes a chemiluminescence aperture 154 that further confines detection to a sensed volume.

Light next passes through a chemiluminescence fiber optic cable 156, which may be replaced by any suitable mechanism for directing light from the composition toward the detector. Fiber optic cable 156 is analogous to excitation and emission fiber optic cables 110*a,b* and 134*a,b* in the photoluminescence optical system. Fiber optic cable 156 may include a transparent open-ended lumen that may be filled with fluid. This lumen would allow the fiber optic to be used both to transmit luminescence from a microplate well and to dispense fluids into the microplate well. The effect of such a lumen on the optical properties of the fiber optic could be minimized by employing transparent fluids having optical indices matched to the optical index of the fiber optic.

Light next passes through one or more chemiluminescence intensity filters, which generally comprise any mechanism for reducing the intensity of light. In apparatus 90, intensity is altered by chemiluminescence neutral density filters 158. Light also may pass through other filters, if desired.

Light last passes to a detector, which converts light into signals that may be processed by the apparatus. In apparatus 90, there is one chemiluminescence detector 160. This detector may be selected to optimize detection of blue/green light, which is the type most often produced in chemiluminescence. A preferred detection is a photomultiplier tube, selected for high quantum efficiency and low dark count at chemiluminescence wavelengths (400–500 nanometers).

Figure 12:
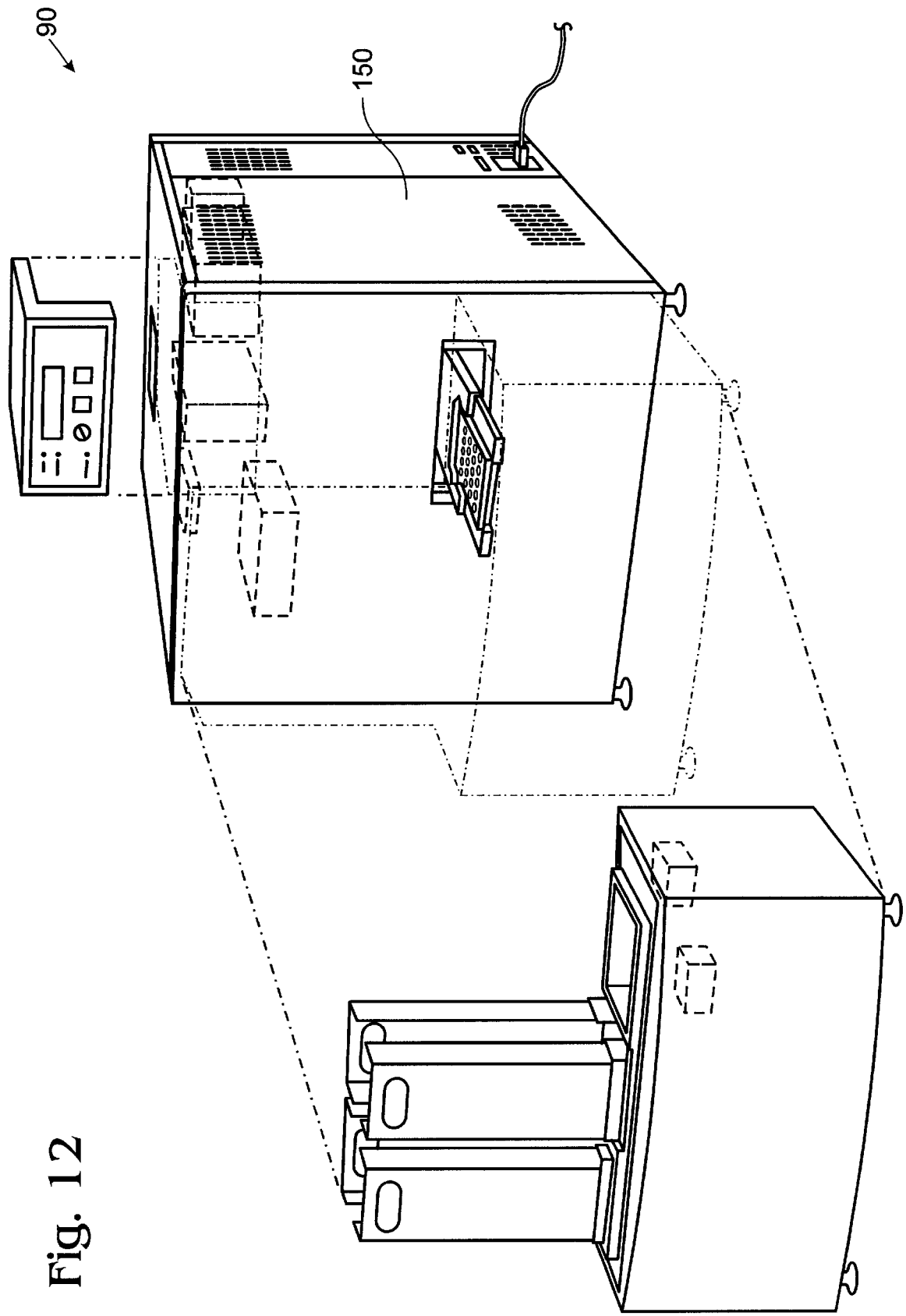
FIG. 12 is a partially exploded perspective view of a housing for the apparatus of FIG. 8.

Housing. FIG. 12 shows a housing 200 and other accessories for the apparatus of FIGS. 8–11. Housing 200 substantially encloses the apparatus, forming (together with light source slots 103*a–d*) two protective layers around the continuous high color temperature xenon arc lamp. Housing 200 permits automated sample loading and switching among light sources and detectors, further protecting the operator from the xenon arc lamp and other components of the system.

Additional details of an apparatus suitable for implementing features of the invention age shown in U.S. patent application Ser. No. 09/160,533, which is incorporated herein by reference.

C. Apparatus 260

Figure 13:
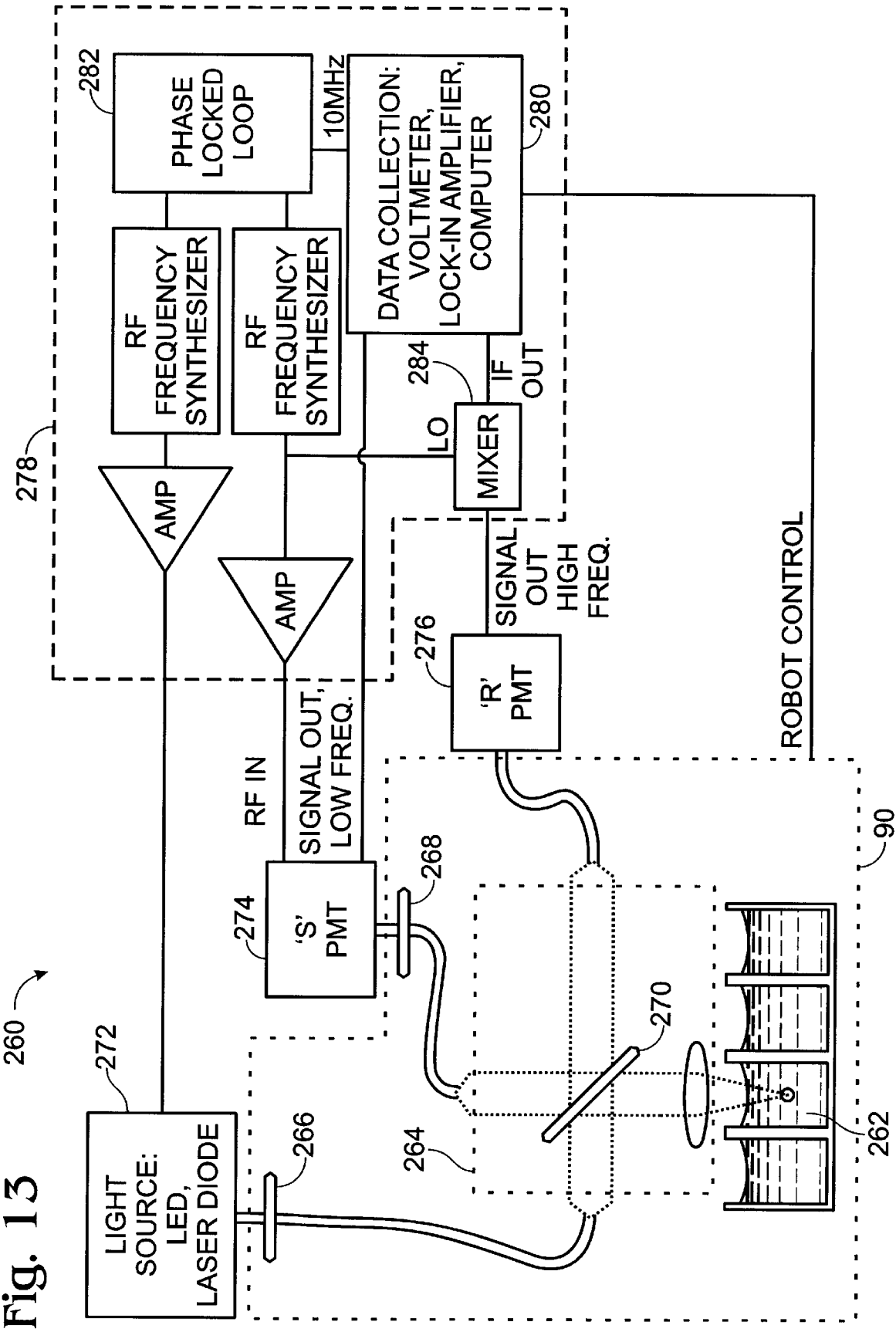
FIG. 13 is a schematic view of another alternative apparatus for detecting light in accordance with the invention.

FIG. 13 shows another alternative apparatus 260 for detecting light transmitted from a composition 262, where the detection and/or processing may be performed in the frequency-domain. Apparatus 260 includes substantial portions of apparatus 90, including its fiber-optic-coupled optics head 264, excitation 266 and emission 268 filters, dichroic beam splitter 270, and mechanisms for sample positioning and focus control. However, apparatus 260 also may include alternative light sources 272, sample ('S') detectors 274, reference ('R') detectors 276, and detection electronics 278. In FIG. 13, alternative components 272–278 are shown outside apparatus 90, but they readily may be included inside housing 250 of apparatus 90, if desired.

Apparatus 260 may provide incident light in various ways, as described above. For example, analytes absorbing blue light may be excited using a NICHIA-brand bright-blue LED (Model Number NSPB500; Mountville, Pa.). This LED produces broad-spectrum excitation light, so excitation filter 266 may be selected to block the red edge of the spectrum. If analytes are excited using a laser diode, an excitation filter is not necessary.

Apparatus 260 may detect emitted light and convert it to a signal in various ways. This demodulation/deconvolution may be internal to the photodetector, or it may be performed with external electronics or software. For example, emitted light can be detected using sample detector 274, which may be an ISS-brand gain-modulated PMT (Champaign, Ill.). High-frequency emitted light can be frequency down-converted to a low-frequency signal using a technique called heterodyning. The phase and modulation of the low-frequency signal can be determined using a lock-in amplifier 280, such as a STANFORD RESEARCH SYSTEMS brand lock-in amplifier (Model Number SR830; Sunnyvale, Calif.). Lock-in amplifier 280 is phase locked using a phase-locked loop 282 to the modulation frequency of light source 272. To correct for drift in the light source, the output of light source 272 may be monitored using reference detector 276, which may be a HAMAMATSU-brand PMT (Model Number H6780; Bridgewater, N.J.). If reference detector 276 can respond to high-frequency signals, the heterodyning step can be performed using an external mixer 284. The phase and modulation of reference detector 276 also may be captured by lock-in amplifier 280 and used to normalize the signal from sample detector 274.

Apparatus 260 may be controlled by a computer or processor. The computer may direct sample handling and data collection. Generally, phase and modulation data will be collected at one or more frequencies appropriate for the lifetime of the analyte. In some cases, phase and modulation may be measured at one or a few frequencies and processed by the computer or processor to help reduce detected background.

D. Additional Comments

As described above, photoluminescence assays include illuminating a sample with light from a light source, and detecting light emitted from the sample. Photoluminescence detection devices typically employ one of various light sources for illuminating the sample. For example, in academic research laboratories, light sources for luminescence polarization assays have included lasers and arc lamps (e.g., xenon arc lamps). Unfortunately, these light sources suffer from a number of shortcomings. The gas in xenon arc lamps is under high pressure (about 10 atmospheres), so that explosion is always a danger. The power supplies for lasers and xenon arc lamps operate at very high currents (about 25 amps) and voltages (about 20,000 to 40,000 volts), so that electrocution and other health hazards are always a danger. In particular, the power supplies for arc lamps can deliver a lethal shock when the lamps are started. The power supplies also may produce transients that can damage other electronic components of the system. The light emitted by lasers and xenon arc lamps is very intense, so that eye damage is always a danger. In particular, the extreme brightness may damage the retina, and ultraviolet light emitted by xenon arc lamps and some lasers may damage the cornea. The spectral output of lasers and some (e.g., mercury) arc lamps is very limited, so that desired excitation wavelengths may not be available. The lifetime of arc lamps may be very short typically around 300 hours, so that the lamp must be changed frequently, further exposing the operator to dangers posed by the lamp and power supply. The short-wavelength light produced by some (e.g., xenon) arc lamps may produce ozone.

These shortcomings assume even greater significance outside the research laboratory. For example, in high-throughput screening applications, the light source may be used nearly continuously, so that the dangers posed by lasers and arc lamps are ever present. The light source also may be used by relatively unskilled operators, who may be unfamiliar with or unreceptive to safety issues.

In high-throughput screening laboratories, light sources for luminescence polarization assays previously have included incandescent (e.g., tungsten) lamps and flash lamps. Incandescent lamps are relatively common and inexpensive, and include lamps from overhead projectors. Incandescent lamps put out broad-spectrum light, so that they may be used with a variety of luminescent compounds. Flash lamps are more exotic, but provide some advantages over incandescent lamps. In particular, flash lamps may be used for both time-resolved and steady-state measurements. This flexibility allows the same light source to be used in instruments that perform multiple assays, such as steady-state and time-resolved luminescence polarization assays. Moreover, flash lamps may have long lifetimes, as long as 10,000 hours.

Aspects of the invention may address some or all of these shortcomings by using a high color temperature light source.

4. Methods of Measuring Luminescence

The above-disclosed apparatus can be used to conduct a variety of steady-state and time-resolved luminescence assays, including polarization assays. Steady-state assays measure luminescence under constant illumination, using the continuous light source. Time-resolved polarization assays measure luminescence as a function of time under time-varying illumination, using either the continuous light source, with its intensity appropriately modulated, or the time-varying light source.

Intensity assays can be conducted by monitoring the intensity of the luminescence emitted by the composition.

Polarization assays can be conducted as follows. Excitation light from the continuous light source is directed through an excitation filter, low-luminescence fiber optic cable, and excitation polarization filter. Excitation light then is directed to a beamsplitter, which reflects most of the light onto a composition and transmits a little of the light into a light monitor. Emitted light from the composition is directed back through the beamsplitter and then is directed through another low-luminescence fiber optic cable, an emission filter, and a polarization filter (in either the S or P orientation) before detection by a photomultiplier tube or other detector. Two measurements are performed for each composition, one with excitation and emission polarizers aligned and one with excitation and emission polarizers crossed. Either polarizer may be static or dynamic, and either polarizer may be set in the S or P orientation, although typically the excitation polarizer is set in the S orientation. In some applications, polarized light may be transmitted to and detected from a fixed assay or examination site as successive samples are automatically, serially aligned in an optical path intersecting the examination site.

Additional luminescence assays can be conducted using procedures outlined in various patent applications cross-referenced above, Joseph R. Lakowicz, *Principles of Fluorescence Spectroscopy* ($2^{nd}$ Ed. 1999) and/or generally known to persons of ordinary skill in the art. Such additional assays include fluorescence resonance energy transfer (FRET), fluorescence lifetime (FLT), total internal reflection fluorescence (TIR), fluorescence correlation spectroscopy (FCS), and fluorescence recovery after photobleaching (FRAP), as well as their analogs based on phosphorescence and higher-order electronic transitions.

5. Signal Enhancement

Enhancements of signal-to-noise and signal-to-background ratios may be important in polarization and other luminescence assays, especially those involving dilute samples. For example, binding assays can be used to probe binding between molecules having subnanomolar dissociation coefficients, if acceptable signal-to-noise and signal-to-background ratios can be obtained from compositions having subnanomolar luminophore concentrations. The methods for enhancing signal-to-noise and signal-to-background ratios described below are especially useful with such dilute samples, hereby minimizing reagent cost that otherwise can be considerable.

Sensitivity and dynamic range can be enhanced by selecting optical components having low intrinsic luminescence and high intrinsic throughput; such as the fiber optic cables and beamsplitters described above. In such on approach, some components may be shared by different modes, whereas other components may be unique to a particular mode. For example, photoluminescence intensity and steady-state photoluminescence polarization modes may share a continuous light source; time-resolved luminescence modes may share a time-varying light source, and chemiluminescence modes may not use a light source. Similarly, photoluminescence and chemiluminescence modes may use different detectors, each selected for the application.

Sensitivity also can be enhanced by reducing the contribution of noise to the measurements. In luminescence polarization assays, various factors contribute to noise, Such as (1) background noise and (2) intensity noise. Background noise refers to contributions to the signal from luminescent species other than the luminescent species of interest, including luminescent species in the apparatus and sample holder. Intensity noise refers to fluctuations in light intensity, including those arising from photon noise.

Background noise can be reduced by reducing autoluminescence from the apparatus and sample holder. For example, the apparatus may use low luminescence components, such as fused silica fiber optic cables. Similarly, the sample holder or substrate may be constructed of low luminescence materials, such as black polystyrene.

Background noise also can be reduced by reducing detection of luminescence from components of the sample that are bound to the sample holder and immobilized, spuriously increasing polarization. For example, the walls of the sample holder may be constructed or treated to reduce binding. Alternatively, in apparatus capable of detecting light transmitted substantially exclusively from a sensed volume (such as apparatus 90 and 260 described above), the sensed volume may be positioned near the center of the composition, away from the walls of the sample holder.

Intensity noise can be reduced by correcting for fluctuations in light source intensity, among others. Light source fluctuations arise due to fluctuations in power from the power supply and drift in the position of the arc in arc lamps, among others. Light source fluctuations can lead to luminescence fluctuations, because the amount of luminescence is proportional to the amount of excitation light. Luminescence fluctuations are especially problematic in luminescence polarization assays, because such assays involve comparing the magnitude of successively measured luminescence signals. Light source fluctuations can be reduced by choosing a stable light source and by rescaling the luminescence signal using information obtained from a light source monitor, as described above.

Intensity noise also can be reduced by increasing the number of photons (i.e., the amount of light) detected, which reduces photon noise. Photon (or shot) noise arises due to the statistical nature of light and can be described by the same statistical law used to describe radiation decay. In particular, if an average of N photons are detected during a given time interval, the standard deviation in that number due to photon noise will be $\sqrt{N}$. The relative significance of photon noise decreases as the number of detected photons increases, because the ratio of the standard deviation in the signal to the signal goes as $\sqrt{N}/N = 1\sqrt{N}$. Although there may be many sources of intensity noise, the limit set by photon noise can never be overcome; however, the significance of photon noise can be reduced by increasing the number of photons collected by the detector. The umber of photons collected can be increased by increasing the intensity of the light source, the efficiency of the detector, and/or the throughput of components of the optical relay structure, such as the beamsplitter, among others.

Photon noise creates noise in luminescence polarization assays. To a very good approximation, the noise in the polarization is proportional to the noise in the luminescence intensities from which the polarization is calculated and corresponds to seven mP standard deviation in polarization for every one percent standard deviation in intensity. This relationship essentially is independent of the degree of polarization. Photon noise puts a premium on simply collecting enough light, especially in rapid high-throughput screening measurements using the optically restrictive microplate format. For additional information, see the calculation in U.S. Provisional Patent Application Serial No. 60/063,811, which is incorporated herein by reference.

Most well-developed polarization assays have maximum polarization changes of between 100 mP and 200 mP, so acceptable standard deviations in the polarization should be no greater than about 5 mP to 10 mP. This requires detection of at least 10,000 photons per intensity measurement to reduce intensity noise to about 1%. The inefficiency of polarization optical systems increases the problem. The number of photons collected is proportional to both the concentration and the detection time, leading to trade-offs between probe concentration and screening throughput. High concentrations of reagents not only are expensive, but also produce insensitive binding assays if they exceed the dissociation constant of the binding reaction.

Figure 14:
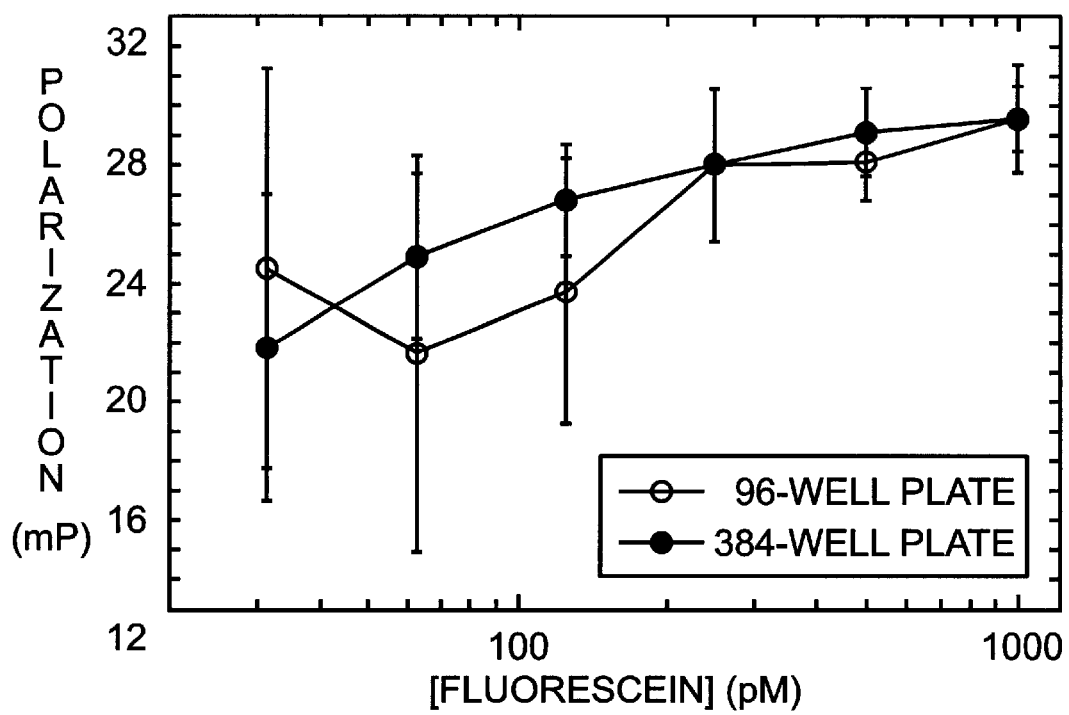
FIG. 14 is a graph of polarization versus fluorescein concentration measured in 96-well and 384-well microplates, showing the sensitivity of the apparatus.
Figure 15:
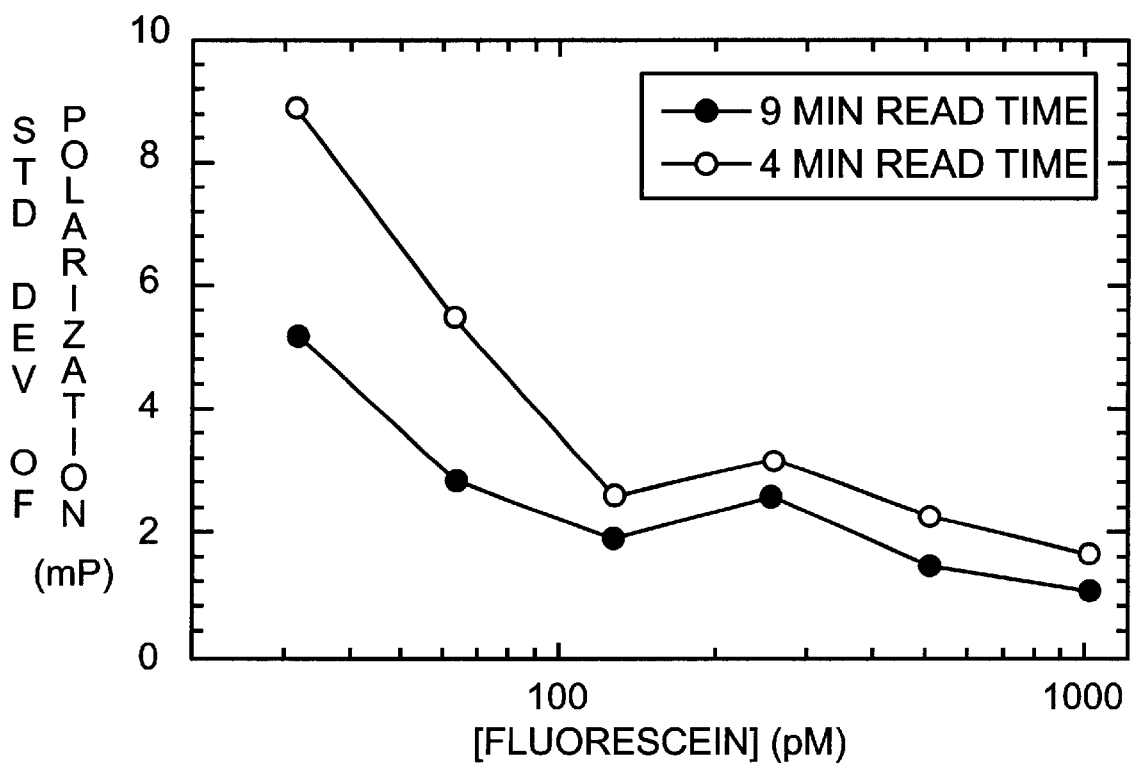
FIG. 15 is a graph of the standard deviation of polarization versus fluorescein concentration measured in 384-well microplates, determined after 4-minute and 9-minute whole microplate read times, showing the sensitivity of the apparatus.
Figure 25:
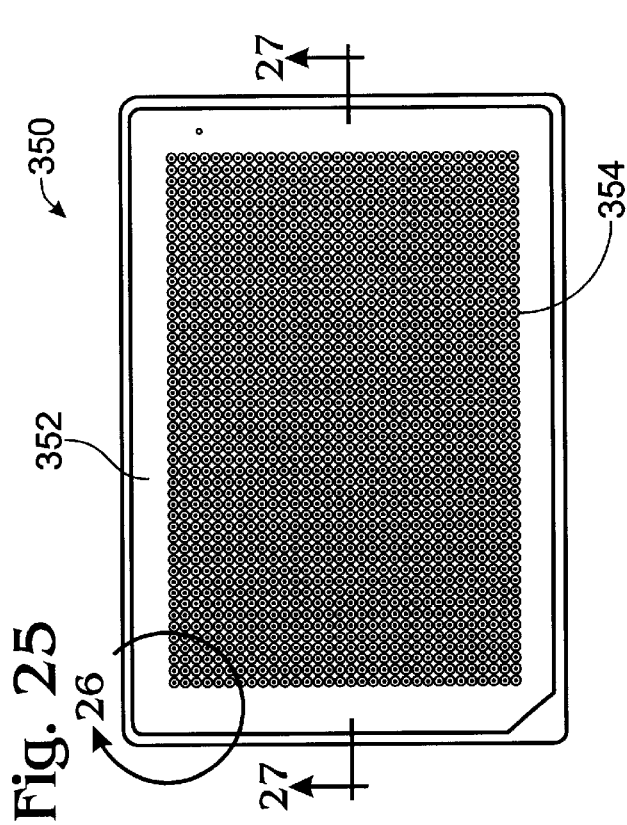
FIG. 25 is a top view of the microplate in FIG. 24.
Figure 27:
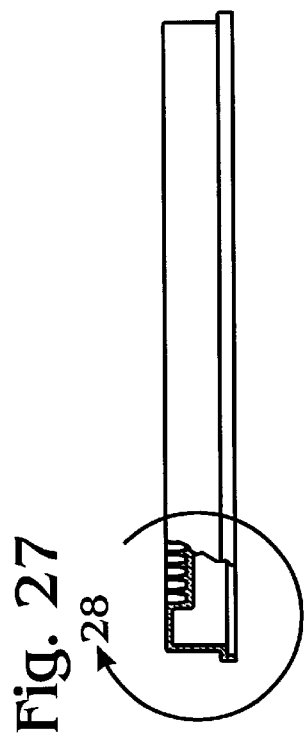
FIG. 27 is a cross-sectional view of the microplate in FIG. 24, taken generally along line 27—27 in FIG. 24.
Figure 26:
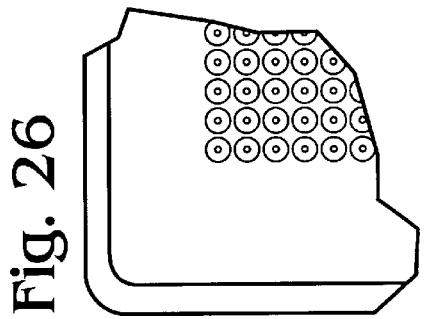
FIG. 26 is an enlarged portion of the top view in FIG. 25, showing details of the sample wells.
Figure 24:
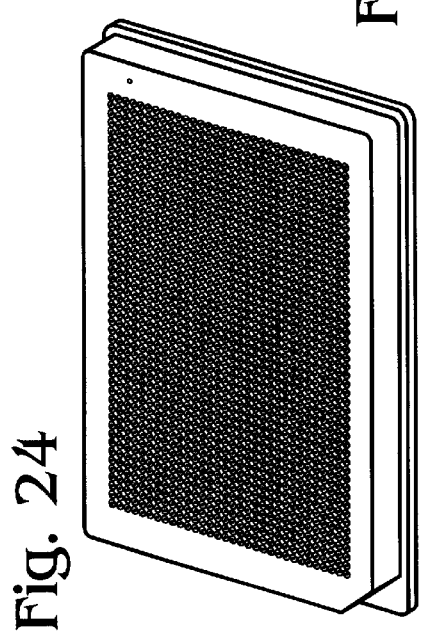
FIG. 24 is a perspective view of a 1536-well microplate constructed in accordance with the invention.
Figure 28:
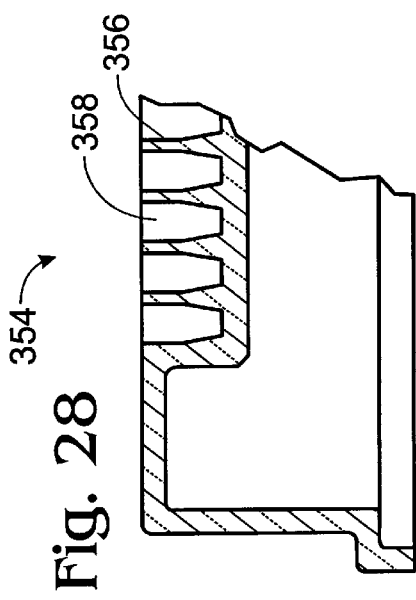
FIG. 28 is an enlarged portion of the cross-sectional view in FIG. 27, showing details of the sample wells.

FIGS. 14–15 show results that characterize a luminescence polarization apparatus constructed in accordance with the invention. Data were collected at room temperature using the preferred apparatus shown in FIGS. 8–13.

FIG. 14 is a graph showing polarization in a serial dilution of fluorescein in 96- and 384-well microplates. The graph demonstrates that the polarization of fluorescein can be measured with adequate accuracy and precision down to, or below, 100 pM, because the measured value is substantially independent of concentration down to, or below, this concentration.

FIG. 15 is a graph showing the noise (or standard deviation) in polarization in a serial dilution of fluorescein in 384-well microplates. As described above, noise below 5–10 mP is sufficiently small for most practical polarization assays. Good precision may be obtained at subnanomolar label concentrations in rapidly scanned 384-well microplates, and even better precision may be obtained in more slowly scanned microplates. The size of the error bars shows that the number of photons collected by the detector exceeds 10,000 in 100 milliseconds from a 100 picomolar fluorescein solution at pH 7.5.

6. Description of Preferred Light Sources

Photon noise can be reduced by using a sufficiently high-intensity light source, such as a continuous high color temperature xenon arc lamp or a laser, among others, as described above. The following table compares the preferred continuous and time-varying light sources used in apparatus 90 and 260.

| Summary | Continuous Light Source | Flash Lamp Light Source | Comparison (Flash/ Continuous) |
|---|---|---|---|
| Life of light source | 300 hrs | 10,000 hrs | 6% |
| Total power of light source | 13,000 mW | 830 mW | 5% |
| Visible power (390–770 nm) | 5100 mW | 230 mW | 3% |
| Infrared power (>770 nm) | 7300 mW | 190 mW | 11% |
| Ultraviolet power (300–390 nm) | 620 mW | 68 mW | 4% |
| Apparatus power (485 nm) | 7.1 mW $1.7 \times 10^{16}$ photons/sec | 0.29 mW $7.1 \times 10^{14}$ photons/sec | 4% |
| Photons/sec from a 1 Nm luminophore solution (estimated) | $1 \times 10^8$ photons/sec | $5 \times 10^6$ photons/sec | 5% |
| Photons/sec from a 10 pM luminophore solution (estimated) | $1 \times 10^6$ photons/sec | $5 \times 10^4$ photons/sec | 5% |

The lifetime of the continuous lamp is only 1/33 the lifetime of the flash lamp. The lifetime of the continuous lamp was taken directly from the manufacturer's specifications. The lifetime of the flash lamp was computed using the manufacturer's specification. Specifically, the flash lamp is run at 100 flashes per second, using 250 mJ of electrical power per flash; at this power level, tie lifetime of the flash lamp is rated at $1 \times 10^9 - 1 \times 10^{10}$ flashes, corresponding to a lifetime of about 10,000 hours ($5 \times 10^9$ flashs/[100 flashs/sec $\times$ 3600 sec/hour]).

The continuous lamp provides about 20 times more light than the flash lamp. The total optical power of the continuous lamp (collected by a F/1.0 optical system) is 13 W over the wavelength range 300–4000 nm. The total optical power of the flash lamp (collected by a F/1.0 optical system) is 830 mW over the wavelength range 100–4000 nm. The total optical power of the flash lamp was derived from the electrical energy, the electrical-to-optical conversion efficiency, the optical collection efficiency, and the repetition rate (250 mJ$\times$50%$\times$6.6%$\times$100 Hz). The optical powers of the different spectra of the flash lamp were derived by multiplying the total optical power of the flash lamp by the fraction of the power in each wavelength range, i.e., ultraviolet (300–390 nm) 8.3%, visible (390–770 nm) 28%, and infrared (770+nm) 24%.

The optical power in the preferred apparatus was determined after passage through a bandpass filter (center 485 nm, bandwidth 20 nm). The optical power in photons per second was calculated by assuming that all photons had a wavelength of 485 nm (energy=1240 eV$\times$nm/wavelength).

High-throughput screening requires that lift be collected quickly and efficiently, so that assays can be accurately and rapidly performed. A 1% error in intensity, corresponding to a 7 mP error in polarization, requires collection of at least 10,000 photons, as described above. For high-throughput screening, these photons should be collected within 100 ms, corresponding to a collection rate of 100,000 photons/sec. Bothlamps produce more than 100,000 photons/sec, but the criterion is to collect 100,000 luminesence photosensor, not to produce 100,000 excitation photons/sec. Specifically, the criterion is to count at least 10,000 photons in 100 msec ($1 \times 10^5$ photon/sec) for low concentrations of luminophore (less than 1 nM. The preferred apparatus achieves this photon limit at roughly 10–100 pM for polarization assays.

The detection efficiency is given by the product of an emission efficiency, a collection efficiency, a transmission efficiency, and a detector quantum efficiency, as calculated below.

The emission efficiency is determined by a product of the fractional absorption and quantum yield. The fractional absorption is determined by the Beer-Lambert law, $-\log[I/I_0]=\epsilon c l$, where I is transmitted intensity, $I_0$ is incident intensity, $\epsilon$ is extinction coefficient, c is concentration, and 1 is path length. The molar extinction coefficient of typical luminophores is about 50,000 per molar per centimeter, and the path length in typical microplates is about 5 mm. Thus, the fraction of photons absorbed is about $6 \times 10^{-5}$ in a 1 nM solution and about $6 \times 10^{-7}$ in a 10 pM solution. The quantum yield (ratio of photons emitted to photons absorbed) of typical luminophores is 0.9, so that about $5 \times 10^{-5}$ of the incoming photons are converted to luminescence emission photons (at 1 nM). This is effectively the emission efficiency.

The collection efficiency is determined by numerical aperture. Luminescence is emitted over all angles, whereas luminescence is collected over limited angles. Specifically, luminescence is collected over a cone angle θ given by the formula $\theta = 2 \arcsin[(NA)/n)]$, where NA is numerical aperture and n is index of refraction. The optical collection efficiency is about 3% for an NA of 0.39 and about 1% for an NA of 0.22.

The transmission efficiency is determined by the optics through which the light passes between the sample and detector. The transmission efficiency in the preferred apparatus probably is about 2%.

The detector quantum efficiency is determined by the detector. For example, the detector quantum efficiency of a photomultiplier tube (PMT) typically is about 20–25%, and the detector quantum efficiency of a photodiode or other solid-state device typically is about 80%.

The preferred detector may vary with experimental conditions. At low light levels, a PMT may be preferred, because a PMT typically will have a lower background (i.e., dark count) and so contribute less noise to the system under these conditions. At higher light levels, a photodiode may be preferred, because a photodiode typically has a higher detector quantum efficiency and because any shortcoming in background relative to a PMT should be offset by a higher quantum efficiency.

Thus, the overall detection efficiency assumes values as follows:

| Concentration | Detection Efficiency (Estimated) |
| --- | --- |
| 1 nM | $5 \times 10^{-5} \times 0.03 \times 0.02 \times 0.25 = 8 \times 10^{-9}$ |
| 10 pM | $5 \times 10^{-5} \times 0.03 \times 0.02 \times 0.25 = 8 \times 10^{-11}$ |

To determine if the continuous and/or flash lamps satisfy the collection criterion of 100,000 photons per second, the detection efficiency was multiplied by the excitation flux to yield an estimated measurable flux at 1 nM and 10 pM (measured in photons/sec). The estimated measurable flux shows that the continuous lamp fails the criterion of 100,000 photons per second somewhere below 10 pM for a typical luminophore, whereas the flash lamp fails the criterion somewhere near 200 pM (roughly 20 times higher). Thus, the continuous lamp satisfies the collection criteria, whereas the flash lamp does not. Specifically, the flash lamp has enough optical power to make statistically significant measurements at 1 nM, but not at 10 pM, where it leads to the collection of fewer than $1 \times 10^5$ photons/sec.

In summary, the continuous lamp has a power of greater than 1 watt over the visible wavelength range of 390 to 770 nm, and is sufficient to reduce photon noise to less than 1 percent of a light signal emitted from a 100 picomolar fluorescein solution at pH 7.5.

7. Description of Microplates

Samples may be supported by any substrate or material capable of supporting the sample for luminescence analysis at one or more examination or assay sites. Depending on the embodiment, suitable substrates include microplates, PCR plates, DNA arrays (such as biochips), and hybridization chambers, among others, where features such as microplate wells and DNA array sites may comprise assay sites, Preferred microplates are described below. Preferred PCR plates would include the same (or a similar) footprint, well spacing, and well shape as the preferred microplates, while possessing a stiffness adequate for automated handling and a thermal stability adequate for PCR. Preferred DNA arrays are described in Bob Sinclair, *Everything's Great When It Sits on a Chip: A Bright Future for DNA Airways*, 13 THE SCIENTIST, May 24, 1999, at 18. Preferred hybridization chambers are described in PCT Patent application Ser. No. PCT/US99/03678, which is incorporated herein by reference.

FIGS. 16–28 show preferred microplates for supporting samples for luminescence assays in a plurality of wells or assay sites. These microplates differ in their well shape, well size, and well density, among other parameters. The remainder of this section describes microplates constructed in accordance with aspects of the invention, including (A) 96-well microplates, (B) 384-well microplates, (C) 1536-well microplates, and (D) miscellaneous microplates.

A. 96-Well Microplates

Figures 16, 17, 18, 19:
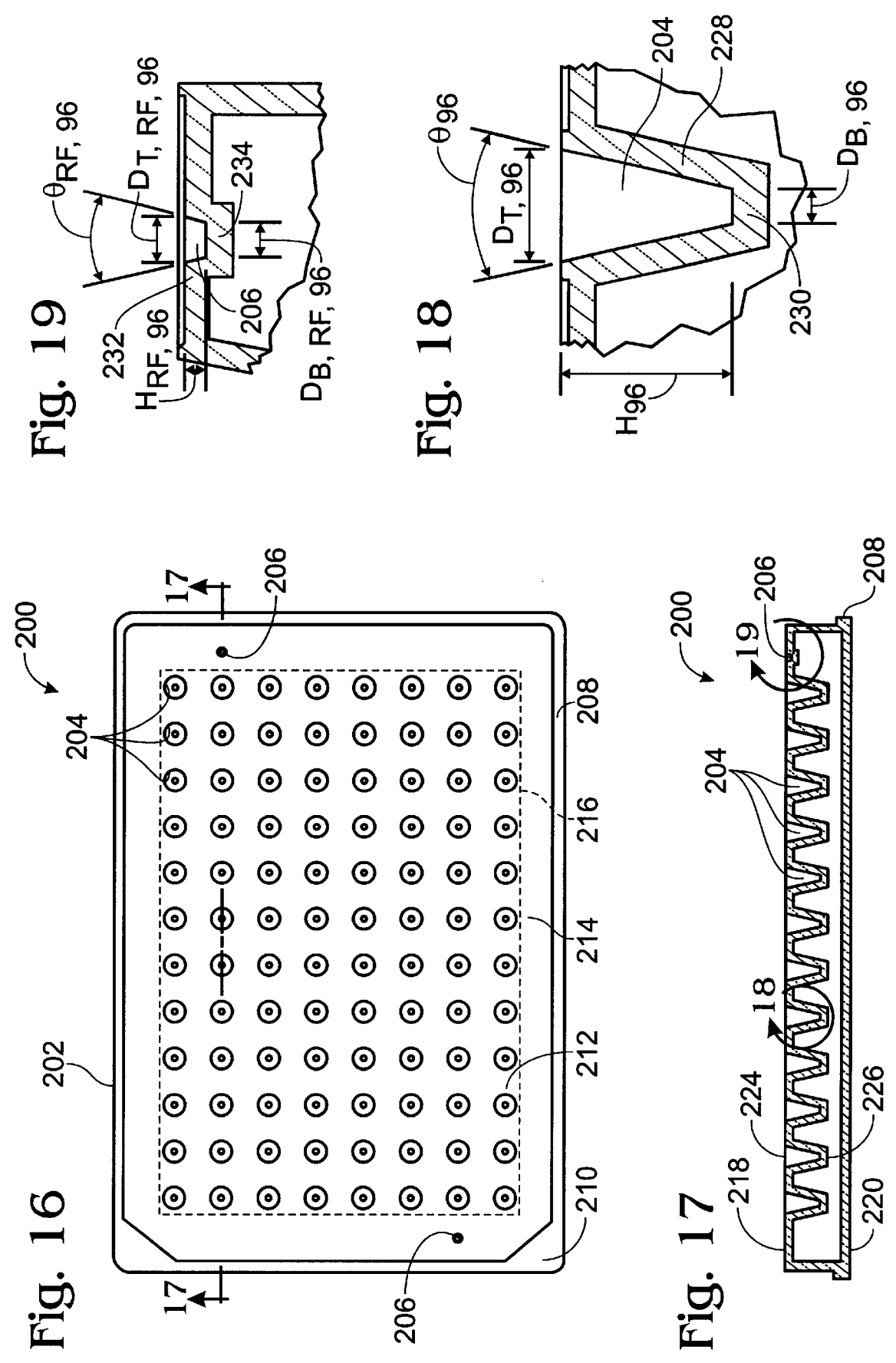

FIG. 16 is a top view of a 96-well microplate 200 constructed in accordance with aspects of the invention. Microplate 200 includes a frame 202 and a plurality of sample wells 204 disposed in the frame. In some embodiments, microplate 200 may include one or more reference fiducials 206 disposed in the frame.

Frame 202 is the main structural component of microplate 200. The frame may have various shapes and various dimensions. In microplate 200, frame 202 is substantially rectangular, with a major dimension X of about 127.8 mm and a minor dimension Y of about 85.5 mm. Frame 202 may be adapted for ease of use and manufacture. For example, fame 202 may include a base 208 to facilitate handling and/or stacking, and frame 202 may include notches 210 to facilitate receiving a protective lid. Frame 202 may be constructed of a material, such as a thermoplastic, that is sturdy enough for repeated, rugged use and yet minimally photoluminescent to reduce background upon illumination.

Frame 202 includes a sample well region 212 and an edge region 214 forming a perimeter 216 around the sample well region. Sample wells may be disposed in the sample well region in various configurations. In microplate 200, sample wells 204 are disposed in sample well region 212 in a substantially rectangular 8×12 array, with a pitch (i.e., center-to-center interwell spacing) along both X and Y of about 9 mm. This pitch correspond to a density of wells of about one well per 81 mm$^2$.

Reference fiducials 206 may be used for identification, alignment, and/or calibration of the nicroplate. Reference fiducials may be disposed in the sample well region and/or the edge region in various configurations. In microplate 200, reference fiducials 206 are disposed in edge region 214, substantially aligned with a row of sample wells along the X dimension. Reference fiducials preferentially are positioned in corners of the microplate, near where optical analysis begins, so that they may quickly be identified and analyzed. Reference fiducials may be positioned in rotationally symmetric positions, so that microplates may be loaded into an optical device and analyzed backwards without difficulty. Further aspects of reference fiducials are described in U.S. patent application Ser. No. 09/156,318 and PCT patent application Ser. No. PCT/US99/08410, which are incorporated herein by reference.

FIG. 17 is a cross-sectional view of microplate 200, showing sample wells 204, reference fiducial 206, and base 208. In microplate 200, frame 202 has a top 218, a substantially parallel bottom 220, and substantially perpendicular sides 222. Top 218 may have various shapes, although it typically is flat. (Top 218 may be surrounded by a raised edge to facilitate stacking.) Frame 202 has a height H of about 12 mm, corresponding generally to the separation between top 218 and bottom 220. This height is large enough to facilitate handling by sample handlers and/or a stage, and yet small enough to permit optical analysis of the entire well. Sample wells 204 are disposed with open, optically transparent ends 224 directed toward top 218, and closed, optically opaque ends 226 directed toward bottom 220. In some embodiments, optically opaque ends 226 may be replaced by optically transparent ends to permit bottom illumination and/or detection. Reference fiducial 206 is disposed on top 218, although reference fiducials also may be disposed on bottom 220 and/or sides 222.

FIG. 18 is a first enlarged portion of the cross-sections view in FIG. 17, showing details of sample wells 204. Sample wells may have various shapes and various dimensions, as described in detail in subsequent sections. In microplate 200, sample wells 204 are substantially frusto-conical, with substantially straight side walls 228 and a substantially flat bottom wall 230. In microplate 200, optically opaque ends 226 are positioned about 6.7 mm below top 218, and about 5.3 mm above bottom 220. Sample well 204 is characterized by a top diameter $D_{T,96}$, a bottom diameter $D_{B,96}$, a height $H_{96}$, and a cone angle $\theta_{96}$. Here, $\theta_{96}$ is the included angle between side walls 228. In microplate 200, $D_{T,96}$ is about 4.5 mm, $D_{B,96}$ is about 1.5 mm, $H_{96}$ is about 6.7 mm, and $\theta_{96}$ is about 25.4°. Sample well 204 has a total volume of about 50 µL, and a smallest practical working volume of about 1–20 µL.

FIG. 19 is a second enlarged portion of the cross-sectional view in FIG. 17, showing details of reference fiducial 206. Reference fiducials may have various shapes and various dimensions, as described in detail in subsequent sections. In microplate 200, reference fiducial 206 is substantially frusto-conical, with substantially straight side walls 232 and a substantially flat bottom wall 234. Reference fiducial 206 is characterized by a top diameter $D_{T,RF,96}$, a bottom diameter $D_{B,RF,96}$, a height $H_{RF,96}$, and a cone angle $\theta_{RF,96}$. Here, $D_{B,RF,96}$ and $\theta_{RFR,96}$ are substantially equal to $D_{B,96}$ and $\theta_{96}$, the corresponding values for sample well 204. $H_{96}$ is about 1 mm, and $D_{T,RF,96}$ is specified by the other parameters.

B. 384-Well Microplates

FIGS. 20–23 are views of a 384-well microplate 300 constructed in accordance with aspects of the invention. Microplate 300 is similar in many respects to microplate 200 and includes a frame 302 And a plurality of sample wells 304 disposed in a sample well region 312 of the frame. In some embodiments, microplate 300 may include one or more reference fiducials 306 disposed in an edge region 314 or other region of the frame.

The external dimensions of microplate 300 are similar to the external dimensions of microplate 200. However, the density of sample wells in microplate 300 is four times higher than the density of sample wells in microplate 200. Consequently, the pitch (i.e., the center-to-center interwell spacing) in microplate 300 is about 4.5 mm, or about one-half the pitch in microplate 200. This pitch corresponds to a density of wells of about four wells per 81 mm². In microplate 300, reference fiducial 306 is positioned about midway between two rows of sample wells along the X direction; in contrast, in microplate 200, reference fiducial 206 is positioned about in line with a row of sample wells along the X direction. This is because the reference fiducials are positioned in approximately the same position in each microplate, but the center line of one row of sample wells in microplate 200 because the center line between two rows of sample wells in microplate 300 as the density of wells is quadrupled.

Sample wells 304 in microplate 300 are similar to sample wells 204 in microplate 200. Sample wells 304 may be characterized by a top diameter $D_{T,384}$, a bottom diameter $D_{B,384}$, a height $H_{384}$, and a cone angle $\theta_{384}$. The preferred values of $D_{B,384}$ and $\theta_{384}$ for microplate 300 are substantially similar to the preferred values of $D_{B,96}$ and $\theta_{96}$ for microplate 200. However, the preferred value for $D_{T,384}$, which is about 4.7 mm, is smaller than the preferred value for $D_{T,384}$, which is about 6.7 mm. In microplate 300, the upper diameter must be smaller than the upper diameter of the sample wells in microplate 200, because the sample wells are close packed, leaving no more interwell spacing than necessary for moldability. In turn, the preferred value for $H_{384}$ is about 4.7 mm, so that the wells are elevated by about 7.3 mm. Sample well 304 has a total volume of about 25 μL, and a smallest practical working volume of about 1–12 μL.

Reference fiducial 306 in microplate 300 may be essentially identical to reference fiducial 206 in microplate 200.

C. 1536-Well Microplates

FIGS. 24–28 are views of a 1536-well microplate 350 constructed in accordance with aspects of the invention. Microplate 350 is similar in many respects to microplates 200 and 300, and includes a frame 352 and a plurality of sample wells 354 disposed in the frame. The pitch in microplate 350 is about 2.25 mm, or about one-half the pitch in microplate 300 and about one-fourth the pitch in microplate 200. This pitch corresponds to a density of wells of about sixteen wells per 81 mm².

Sample wells 354 may be exclusively frusto-conical, like sample wells 204 in microplate 200 and sample wells 304 in microplate 300. However, due to spatial constraints, the volume of such wells would have to be small, about 1–2 μL. Alternatively, sample wells 354 may have a frusto-conical lower portion 306 coupled to a cylindrical upper portion 308. The volume of such wells may be larger, for example, about 7–8 μL. The larger wells permit use of smaller or larger sample volumes. Larger sample volumes may be useful if the microplate is used in conjunction with standard fluid dispensing equipment, or if reagents are to be added to the well from stock solutions, such as 100×DMSO or DMF stock solutions.

Reference fiducials in microplate 350 may be essentially identical to reference fiducials 206 in microplate 200 and reference fiducials 306 in microplate 300.

D. Miscellaneous Microplates

The invention also may provide additional new microplate designs that are useful for high-efficiency sample analysis in luminescence polarization assays. These designs include:

(i) A microplate having a frame portion and a top portion, where an array of wells is formed in the top portion. The wells are organized in a density of at least about 4 wells per 81 mm². Each well has a bottom wall that is elevated at least about 7 millimeters above a plane defined by a bottom edge of the frame.

(ii) A microplate having an array of conical wells organized in a density of at least about 4 wells per 81 mm².

(iii) A microplate having an array of conical wells, where each well has a maximum volume capacity of less than about 55 microliters. A preferred small-volume well design has a volume capacity of 1–20 microliters.

(iv) A microplate having an array of wells in the top portion, where each well has a maximum volume capacity of less than about 55 microliters and a well bottom that is elevated at least about 7 millimeters above a plane defined by a bottom edge of the frame.

(v) A microplate having an array of wells in a top portion, organized in a density of at least about 4 wells per 81 mm², where each well has a conical portion characterized by a cone angle of at least about 8°.

(vi) A microplate having an array of conical wells characterized by a cone angle $\theta$, where $\theta = 2\arcsin(NA/n)$ and NA is equal to or greater than about 0.07.

(vii) A microplate having an array of wells organized in a density of at least about 16 wells per 81 mm², where each well has a frusto-conical bottom portion and a substantially cylindrical upper portion.

(viii) A microplate comprising a same and a plurality of frusto-conical sample wells disposed in the frame, where the sample wells are characterized by a cone angle of at least about 8°. The microplate further may include a reference fiducial that provides information to facilitate sample analysis.

8. Application of Sensed Volumes

Microplates are a preferred sample holder in luminescence assays. However, sample wells in standard microplates and other luminescence sample holders may have regions that are optically inaccessible, from which luminescence can be neither excited not detected. Sample in such regions effectively is wasted because it does not contribute to the analysis. Wasted sample can translate into significant extra cost, particularly for assays that are performed in large numbers, that use expensive reagents, and/or that are inhomogeneous, requiring washing. Sample wells also may have walls or other regions that are themselves detectable optically, increasing background if such regions luminesce.

Aspect of the invention may address some or all of these shortcomings by using (1) an optical device capable of detecting light substantially exclusively from a sensed volume, and (2) a sample holder configured to support a sample so that the shape of the sample conforms to the shape of at least a portion of the sensed volume. The sample holder may be a sample well in a microplate and may have a conical or frusto-conical shape, so that the sample conforms to a portion of an hourglass-shaped sensed volume.

Figure 29:
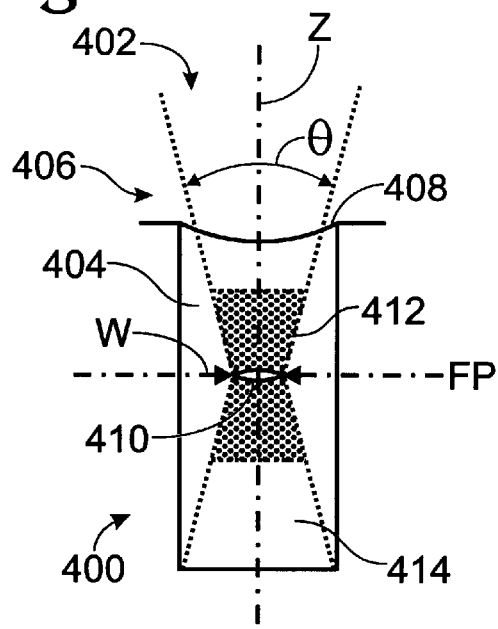
FIG. 29 is a partially schematic cross-sectional view of a standard microplate well.

FIG. 29 is an enlarged cross-sectional view of a standard cylindrical or square microplate well 400, showing air 402 above the sample well, a sample 404 within the sample well, and a light beam 406 passing through the sample well. The interface between air 402 and sample 404 is termed a meniscus 408 and may be convex, plan, or concave.

Light beam 406 is created by an optical device, such as luminescence apparatus 90 described above. The optical device focuses the light so that the light beam has an hourglass shape along a cone or optical axis Z. Light beam 406 is narrowest at its "waist" 410, which has a diameter W and which is located in a focal plane FP of the optical device. Light beam 406 increases in width monotonically above and below waist 410, having a total included angle θ. Angle θ is the cone angle of the "maximum cone" defined by the "marginal rays" of the optical device, and is twice the angle between the marginal rays and the optical axis Z. The marginal rays trace the path of the most outlying light rays normally detectable by the system. The maximum cone defines the outer boundary of the hourglass-shaped light beam and is the volume into which light may be delivered and from which light may be transmitted by the optical device. Angle θ also is the angle subtended at focal plane FP by the light-gathering components (e.g., the objective lens) of the optical device.

Values of W and θ depend on components and properties of the optical device and may be varied by varying these components. For example, cone angle θ is given by the formula $\theta = 2\arcsin(NA/n)$, where "NA" is the numerical aperture of the optical device, and "n" is the index of refraction of the medium adjacent the optical device. Generally, the numerical aperture lies in the range 0.07–1.4, with a preferred range of 0.1 to 0.5 and a preferred value of NA=0.22, corresponding to the numerical aperture of a low-luminescence fused-silica fiber optic cable, The value NA=0.22 is a good compromise, creating a sensed volume that fits into sample wells in a 384-well microplate without hitting walls, and creating a sensed volume that can read to the bottom of microplates conforming to Society of Biomolecular Screening size standards. Generally, the index of refraction lies in the range 1.0–1.6, with a preferred value of n=1.0 corresponding to the index of refraction of air. The preferred numerical aperture and preferred index of refraction correspond to a cone angle of about 25.4°.

The portion of the hourglass to which light may be delivered and from which light may be transmitted further may be limited by one or more confocal optics elements within the optical device. Such confocal optics elements may include apertures placed in image planes of the optical device, conjugate to focal plane FP.

The maximum cone and the confocal optics elements combine to create a sensed volume 412. The shape of sensed volume 412, indicated in FIG. 29 by stippling, may differ in directions parallel and perpendicular to the optical axis Z. Parallel to optical axis Z, the shape may be a Lorentzian, among others. Perpendicular to optical axis Z, the shape may be a Gaussian, or it may be a rounded pulse function, among others. A laser beam might give rise to a Gaussian, whereas a fiber optic bundle might give rise to a rounded pulse function. Generally, lower numerical apertures will create sensed volumes shaped more like cylinders, whereas higher numerical apertures will create sensed volumes shaped more like hourglasses.

Outside the hourglass-shaped beam and sensed volume 412 are optically inaccessible regions 414, from which luminescence is neither excited nor detected. Sample in these regions effectively is wasted, because it does not contribute to the signal. To reduce such waste, the shape and volume of the sample holder may be chosen or designed to conform to the shape and volume of the sensed volume.

Figure 30:
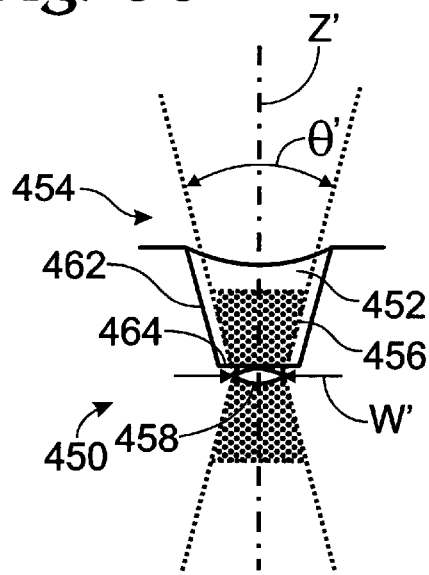
FIG. 30 is a partially schematic cross-sectional view of a sample holder constructed in accordance with the invention.

FIG. 30 is a partially schematic cross-sectional view of a sample holder 450 constructed in accordance with the invention. Sample holder 450 supports a sample 452 illuminated by a light beam 454 forming a sensed volume 456. Sensed volume 456 is shaped substantially like an hourglass, having a waist 458 with diameter W' and conical margins 460 characterized by a cone angle θ' and a cone or optical axis Z'.

Sample holder 450 is configured to support sample 452 so that the shape of the sample conforms to the shape of at least a portion of sensed volume 456. Light is delivered to a sensed volume of the sample from a light source, and transmitted from a sensed volume to a detector. Here, sample holder 450 hag a frusto-conical shape configured to conform to substantially one-half of the hourglass shape of sensed volume 456. Specifically, sample holder 450 has conical wall portions 462 that substantially conform to conical margins 460 of sensed volume 456, and a planar bottom portion 464 that substantially conforms to waist 458 of sensed volume 456. For example, the cone angle associated with conical margins 462 substantially equals cone angle θ' of sensed volume 456. In other embodiments, the sample holder may have a purely conical shape or an hourglass shape, so that it conforms to a larger portion of the sensed volume. In yet other embodiments, the sample holder may have yet other shapes, to conform to alternatively shape sensed volumes. Optically inaccessible regions within sample holder 450 are reduced, so that most of the sample contributes to the analysis, reducing sample waste.

Figure 31:
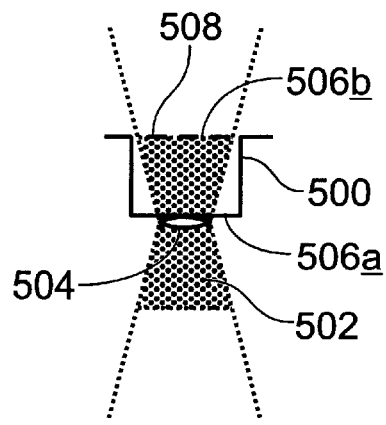
FIG. 31 is a partially schematic cross-sectional view of an alternative sample holder constructed in accordance with the invention.

FIG. 31 is a partially schematic cross-sectional view of an alternative sample holder 500 constructed in accordance with the invention. Sample holder 500 is configured to match substantially half of an hourglass-shaped sensed volume 502. Sample holder 500 is dimensioned go that the waist 504 of the sensed volume may be aligned with the bottom 506a of the sample holder, with the top 508 of the sensed volume substantially aligned with the top 506b of the sample holder. This embodiment may be especially useful for very small sample volumes, such as may be used in 1536-well microplates, because it may increase the sample volume to an amount that may be handled and dispensed more easily.

Figure 32:
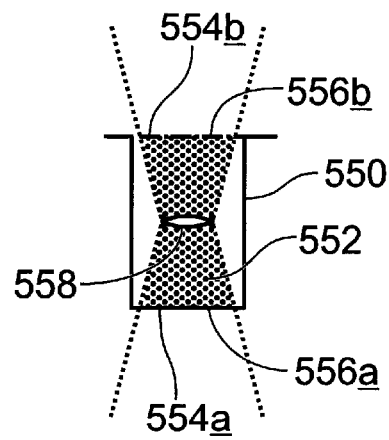
FIG. 32 is a partially schematic cross-sectional view of another alternative sample holder constructed in accordance with the invention.

FIG. 32 is a partially schematic cross-sectional view of another alternative sample holder 550 constructed in accordance with the invention. Sample holder 550 is configured to match substantially all of an hourglass-shaped sensed volume 552. Sample holder 550 is dimensioned so that the bottom and top 554a,b of the sensed volume may be aligned with the bottom and top 55a,b of the sample holder, with the waist 558 of the sensed volume substantially in between. This embodiment also may be especially useful for very small sample volumes.

Preferred sample wells are chosen to optimize lower detection limit, signal-to-noise ratio, and signal-to-background ratio, and to minimize sample volume, for a given sensed volume. Lower detection limit is the lowest concentration of sample that can be measured. Signal-to-noise ratio is the signal from the sample divided by variations in the signal due to noise. Signal-to-background ratio is the signal from the sample divided by the signal from contaminants in the sample, the sample holder, and components of the optical system.

In these wells, the cone angle of the sample holder substantially conforms to the approximately 25° cone angle of the sensed volume of the ANALYST optical device. For frusto-conical wells, optimal cone angles and well bottom diameters will depend on the cone angle and waist diameter of the sensed volume. Cone angles may range from about 8° for a low (0.07) NA optical system, on up. Such cone angles significantly exceed the slight 1–2° angle introduced into molded cylindrical sample holders to permit removal of the sample holder from the molding tool. Bottom diameters may range from about 1 μm for a high NA optical system, on up, though typical values might be 1 mm or 1.5 mm.

The smallest practical working volume for frusto-conical and other sample holders is the volume for which there still is sufficient sample volume to enclose the portion of the sensed volume contained within the sample well, or at least to enclose a sufficient portion of the sensed volume to yield acceptable signal-to-noise and signal-to-background ratios.

If the apparatus is sufficiently flexible, the shape and volume of the sensed volume produced by the apparatus may be adapted like a probe to match the shape and volume of the sample holder. In this way, the sensed volume may be expanded for maximum signal in a large sample holder, and contracted to avoid nearby walls in a small sample holder.

Alternatively, the shape and volume of the sensed volume may be held constant, and the position of the sensed volume varied to match the sample holder and/or assay. In this way, the sensed volume will report on equal volumes of each composition analyzed, so that the apparatus effectively reports "intensive" quantities. Intensive quantities do not depend on the amount of composition in a sample holder; in contrast, extensive quantities do depend on the amount of composition in the sample holder. This approach can be used to facilitate comparison of results obtained from different-sized sample wells. This approach also can be used to facilitate comparison of results obtained from like-sized sample wells containing different volumes of solution.

FIG. 33 shows how the sensed volume can be directed to different regions of a standard microplate well, and how directing the sensed volume affects signal-to-noise and signal-to-background ratios.

In homogeneous assays (Panel B), photoluminescent molecules are distributed uniformly throughout the composition, and the optimum signal-to-noise and signal-to-background ratios are obtained regardless of well geometry when the sensed volume is positioned in the middle of the composition Panel A), so that the sensed volume does not overlap with the meniscus or the bottom or sides of the well. If the meniscus is in the sensed volume, light reflected from the meniscus will be detected. This will decrease sensitivity by increasing background and decreasing signal. If the bottom of the well is in the sensed volume, light reflected from the well bottom will be detected. Moreover, noncomposition photoluminescence arising from fluorescent and other photoluminescent materials that are commonly included in the microplate or adsorbed to the walls of the microplate also will be detected. These two effects will decrease sensitivity by increasing background and decreasing signal. Luminescence measured from the microplate walls will lead to spuriously high luminescence intensities and luminescence polarizations.

In cell-based assays panels C and D), photoluminescent molecules are concentrated in or near cells growing at the bottom of tie well, and the optimum signal-to-noise and signal-to-background ratios are obtained when the sensed-volume is centered about the bottom of the well (Panel A). Such centering may be accomplished either using top optics (Panel C) or bottom optics (Panel D).

For some cell-based assays, microplate wells having a frusto-conically-shaped portion may be particularly advantageous. The conical shape of the well tends to focus cells into a smaller area defined by the substantially flat bottom wall. The conical shape of the well and the selected confocal optics allow substantially all of the cells at the bottom of the well to be detected in the sensed volume, thus maximizing signal sensitivity and reagent utilization regardless of whether the cells are uniformly distributed across the bottom of the well. The conical geometry of the wells also makes it possible to perform cell-based assays from the top without requiring transmission of light through the bottom wall of the well. The geometry is also useful for performing luminescence polarization assays that may be based on receptor/ligand binding to the bottom of the well.

The shape and position of the sensed volume within We well may be affected by (1) the meniscus and (2) the geometry of the sample well, among other factors.

FIG. 34 shows how the meniscus affects the shape and position of the sensed volume within a sample well. The meniscus affects the sensed volume because light is refracted as it crosses the meniscus boundary between the air and the composition. Specifically, light passing from air (with its lower index of refraction) into the sample (with its higher index of refraction) bends toward the normal, as described by Snell's law. Here, the normal is the direction perpendicular to the surface of the meniscus at a given point. If there is no fluid and hence no meniscus, the beam has a nominal undistorted shape (Panel A). If the meniscus is everywhere perpendicular to the light beam, then light passing through the meniscus will not bend, and the beam will retain its nominal undistorted shape (Panel B). For a converging beam, this will occur when the meniscus is appropriately convex. If the meniscus is more than appropriately convex, light will bend toward the middle of the well as it passes through the meniscus, and the sensed volume will be compressed and raised (Panel C). If the meniscus is less than appropriately convex, flat, or concave, light will bend away from the middle of the well as it passes through the meniscus, and the sensed volume will be stretched and lowered (Panel D).

Sample wells can be configured to account for these changes in the shape and position of the sensed volume created as excitation and emission light passes through the meniscus. The invention includes shaping the sample well to account for changes in the shape and position of the sensed volume, and shaping and treating the sample well to alter the shape of the meniscus, as appropriate.

Figure 35:
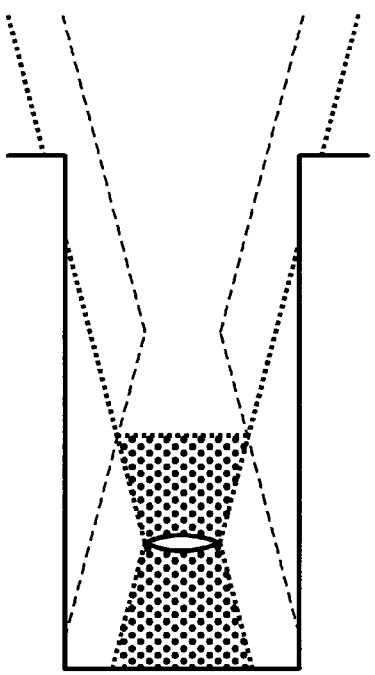
FIG. 35 is a partially schematic cross-sectional view of a sample well, showing how the geometry of the sample well affects the position of the sensed volume.
Figure 36:
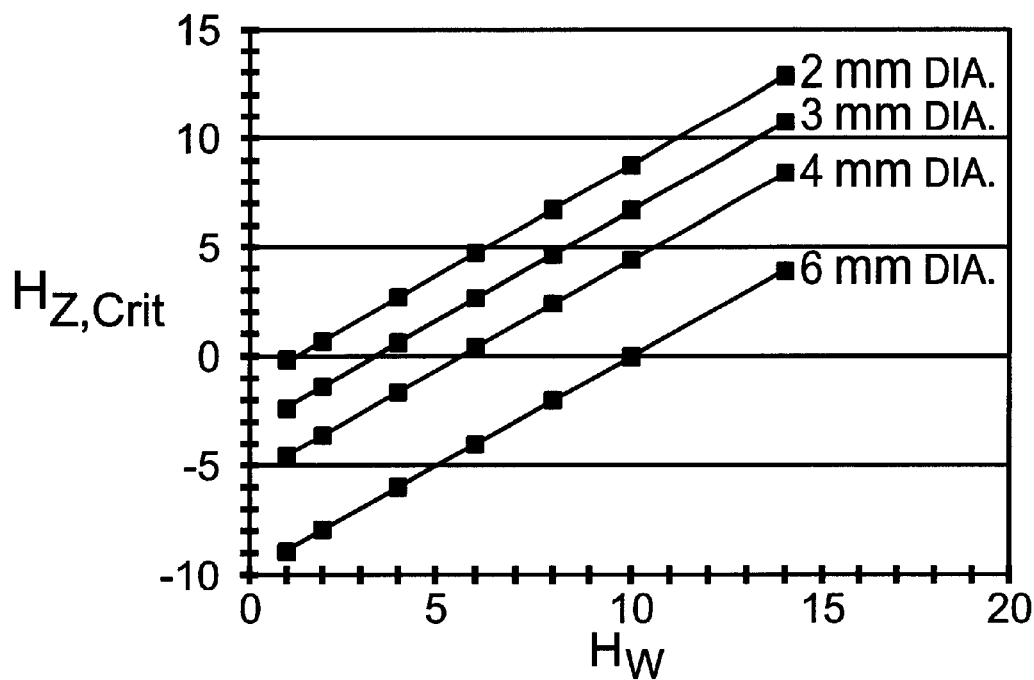
FIG. 36 is a graph showing the relationships between critical Z-height and microplate well height.

FIGS. 35 and 36 show how the geometry of the sample well affects the position of the sensed volume. In particular, if the well is sufficiently narrow relative to the diameter of the beam, or if the well is sufficiently deep relative to the angle made by the beam, then the light beam may impinge upon the top walls of the well. In these cases, setting the Z-height too low can reduce sensitivity (1) by decreasing the desired signal because less light enters the well, and (2) by increasing the background because the light beam illuminates the tops of wells. Many microplates are made from materials that are fluorescent or otherwise photoluminescent, and the instrument will detect this photoluminescence from materials at the tops of wells.

Because beam position is a critical determinant of signal to noise, Z height must be appropriately maintained; Z height should be kept above a critical focal height, $H_{Z,Crit}$. The height at which the beam first impinges on the walls of the well is the critical focal height, $H_{Z,Crit}$. FIG. 36 shows how $H_{Z,Crit}$ depends on the well height $H_W$ and well diameter $D_W$, for a beam of diameter 1.5 millimeters (mm) and a beam angle 25.4°. Similarly, Table 1 shows how $H_{Z,Crit}$ depends on well height and well diameter for four commercially available microplates.

| Plate Type | Well Height (mm) | Well Diameter (mm) | $H_{Z,Crit}$ (mm) |
| --- | --- | --- | --- |
| Costar Black Flat Bottom 96 - Well 3915 | 10.71 | 6.71 | −0.85 |
| Dynatech MicroFluor Round Bottom | 9.99 | 6.78 | −1.72 |
| Costar Black 384-Well 3710 | 11.55 | 3.66 | 6.76 |
| Packard White 384-Well #6005214 | 11.57 | 3.71 | 6.67 |

The increase in $H_{Z,crit}$ shows that for a microplate having a standard height and XY area, as the aspect ratio (length/diameter) and density of wells increases, the ability of a confocal optic system to read small volumes in standard straight-walled wells decreases. This may require reading through the bottom of the well for cell-based assays, which is not always convenient or practical.

Z-height can be optimized for a particular microplate and assay by (1) preparing a test microplate with representative assay (e.g., blanks, positive and negative controls, dilution series), (2) and reading the microplate multiple times at different Z-heights to determine the Z-height that gives the best signal-to-background data. Some combinations of assay and microplate are relatively insensitive to Z-height, while others demonstrate a distinct optimum.

9. Background Subtraction

Optical spectroscopic assays are subject to artifacts that alter the apparent luminescence of the analyte and thus the accuracy, repeatability, and reliability of the assay. Some artifacts increase the apparent luminescence of the analyte, causing intensity-based assays to overreport the amount of light emitted by the analyte. Such artifacts include background. Other artifacts decrease the apparent luminescence of the analyte, causing intensity-based assays to underreport the amount of light emitted by the analyte. Such artifacts include scattering and absorption. Such artifacts also include changes in the composition that change the optical transfer function (photons collected/photons injected), including changes in index of refraction and surface tension.

Optical spectroscopic assays also are subject to artifacts that alter the apparent polarization of the analyte. Such artifacts also include background, scattering, and absorption, among others, and can increase or decrease the apparent polarization.

Among artifacts that alter polarization while increasing the apparent luminescence of the analyte, background is especially significant. Background refers to light and other signals that do not arise from the analyte, but that can be confused with light that does arise from the analyte. Background may arise from non-analyte luminescent components of the sample (e.g., library compounds, target molecules, etc.). Background also may arise from luminescent components of the sample container and detection system (e.g., microplates, optics, fiber optics, etc.). Background also may arise from scattered excitation light that leaks through the optical filters, which is equivalent to luminescence with a zero lifetime, and from room light.

There is no way to eluted every source of background, so methods must be used to discriminate between analyte and background. If the analyte and background have different spectra, background may be at least partially discriminated using appropriate optical filters, which pass light emitted by the analyte but block background. If the analyte and background have overlapping spectra, background may be at least partially discriminated in two ways. First, background may be discriminated using a blank. In this method, data such as intensity data are collected for the sample and for a blank that lacks analyte but otherwise resembles the sample. Background is at least as partially discriminated by subtracting the data obtained from the blank from the data obtained from the sample. Second, background may be discriminated by gating. In this method, data are collected from the sample only at times when the background is low or nonexistent.

Unfortunately, these methods of rejecting background suffer from a number of shortcomings, especially if the analyte and background have overlapping spectra. The use of blanks requires making two measurements for every sample, at least if the background is different for each sample. Background may be different for each sample if each sample is housed in a different container and/or if each sample contains a different, intrinsically luminescent target molecule, such as a peptide, protein, or nucleic acid, among others. The use of gating requires knowledge of the lifetime and intensity of the background. The use of gating also requires collecting data only over limited times, so that data collection is slowed and potentially useful data is discarded. Gating is especially problematic for short-lifetime background, because luminescence from the analyte is most intense for short times after excitation.

Among artifacts that alter polarization while decreasing the apparent luminescence of the analyte, scattering and absorption are especially significant. Scattering can arise if the composition containing the analyte is turbid, so that excitation and/or emission light are scattered out of the optical path and therefore not detected. Absorption can arise if non-analyte components of the composition can absorb excitation and/or emission light. Absorption of excitation light reduces luminescence indirectly, by reducing the amount of light available to excite luminescence. Absorption of emission light reduces luminescence directly. Collectively, absorption of excitation and emission light is termed "color quenching." Scattering and color quenching may vary from sample to sample and therefore be difficult to characterize.

There is no way to eliminate every source of scattering and absorption. This is especially true in compositions containing biological molecules, because biological molecules such as nucleic acids and proteins may absorb light having wavelengths commonly used in luminescence assays.

Background, scattering, absorption, and other artifacts affecting apparent luminescence are significant shortcomings, even for single measurements. However, they are potentially crippling shortcomings in high-throughput genomics applications, where tens or hundreds of thousands of samples may be analyzed each day. In genomics applications, the use of blanks may double the consumption of reagents and the time required for sample preparation and data collection, as well as associated costs. Moreover, in genomics applications, biological molecules that scatter and absorb light often must be employed.

The invention provides methods and apparatus for improving signal resolution in hybridization assays. These improvements may be obtained without using information from a blank, and/or without requiring a determination of the lifetime or intensity of the background. These improvements also may be obtained irrespective of whether a significant amount of the background is being detected by the detector at the same time that light emitted by the analyte is being detected. Consequently, the invention permits discrimination between analyte and background and/or other non-analyte emitters in measurements performed in a single sample container. The invention also permits light to be detected and analyzed continuously, so that signal is not wasted and data collection is not slowed.

A. Overview

In many applications, background can be represented as a combination of (1) a relatively constant background luminescence (from well to well in microplate experiments) having a relatively constant anisotropy and (2) random fluctuations in both the luminescence level and its anisotropy caused by luminescent contamination ("hot wells" in microplate experiments). This background can be reduced or subtracted using various methods, including:

1. Conventional background subtraction using control wells, which generally is not effective in reducing background from hot wells.
2. Premeasuring background from the microplate and subtracting the background after the reagents are added and the measurement is completed.
3. Using FLARe technology to perform the measurement and FLAMe methods to subtract background in polarization measurements, which is effective in reducing variable background from "hot wells," if the background has an average lifetime distinct from the analyte lifetime.
4. Premeasuring the background amsotropy; performing a total intensity measurement on each well; using the average value of the total intensity for all wells to determine the fractional intensity of the background of each well, because all wells should have the same total intensity; and using the anisotropy-based method for background-subtraction of polarization data described below to perform the background subtraction.

The latter methods may involve converting detected light to a signal, and discriminating between a first portion of the signal that is attributable to light emitted by the luminophore and a second portion of the signal that is attributable to a background. The discriminating step may be performed using a processor. The processor may discriminate between the first and second portions of the signal without requiring a determination of the lifetime or intensity of the background, or without requiring the use of information obtained from a blank (irrespective of whether a significant amount of the background is being detected by a detector at the same time that light emitted by the analyte is being detected). The processor also may discriminate between the first and second portions in the frequency domain without requiring a determination of the intensity of the background, or without requiring the use of information obtained from a blank.

Intensity-based method. The following intensity-based method may be used to analyze polarization results:

1. Take polygon measurements on all wells on plate.
2. Identify buffer (background) wells on plate.
3. Determine average intensities of background wells for both $\parallel$ and $\perp$ channels.
4. Subtract average background $\parallel$ and $\perp$ channel intensities from all wells.
5. Calculate polarization for each well using G factor and background-subtracted $\parallel$ and $\perp$ intensities.

Here, step 5 is carried out using the following relation between intensity and polarization:

$$P = \frac{(I_\parallel - I_{\parallel 0}) - G(I_\perp - I_{\perp 0})}{(I_\parallel - I_{\parallel 0}) + G(I_\perp - I_{\perp 0})}, \tag{6}$$

where the $\parallel$ and $\perp$ subscripts indicate the $\parallel$ and $\perp$ intensities, respectively, and the 0 subscript indicates a background intensity.

Anisotropy-based method. A novel alternative anisotropy-based procedure also may be used to analyze polarization results. A basic difference between the intensity-based and anisotropy-based procedures is how the background is subtracted: in the intensity-based procedure, intensifies are subtracted, whereas in the anisotropy-based procedure, anisotropies are subtracted. The anisotropy-based procedure may provide the following benefits: (1) a more robust method for background subtraction, and (2) insight into how hot wells affect polarization measurements, and a mechanism to address them.

Derivation of anisotropy-based method. To simplify the math, the anisotropy-based method is derived in terms of anisotropy rather than polarization, with the understanding that we can readily convert between anisotropy and polarization.

$$R = \frac{2P}{3-P}, \quad P = \frac{3R}{2+R}, \quad \frac{2}{R} = \frac{3}{P} - 1. \tag{7}$$

The underlying assumption for this analysis is that the assay system can be decomposed into two components: (1) the label of interest, and (2) everything else, which is lumped together as background. This typically would include autoluminescence from the microplate or other substrate and from the optical elements of the light detection device. (The same assumption is used in the intensity-based background-subtraction analysis.) The average anisotropy for the system is then given by the following expression:

$$R_T = f_L R_L + f_O R_O. \tag{8}$$

where the multiplier f indicates the fractional intensity of a given component, and the subscripts T, L, and 0 indicate total, label of interest, and background, respectively. Solving for the anisotropy of the label of interest and invoking the relationship $f_L=1-f_0$ yields:

$$R_L = \frac{R_T - f_0 R_0}{f_L} = \frac{R_T - f_0 R_0}{1 - f_0}, \tag{9}$$

The preceding equation indicates that background can be subtracted by manipulating anisotropies rather than intensities. The anisotropy of the label ($R_L$) can be estimated from the total anisotropy ($R_T$) if the background anisotropy ($R_0$) and background relative intensity ($f_0$) are known.

Before proceeding, it is instructive to review typical values for the parameters in this equation. $R_L$ depends on the label of interest; for free fluorescein in PBS, it is about 0.02 (27 mP), and for the antibody-bound tracer in the TKX™ assay kit marketed by LJL BioSystems, it is about 0.1 (140 mP). $R_0$ can range from about 0.400 (500 mP) for PBS in black plates to less than about 0.015 (22 mP) for white plates. $f_0$ has an absolute range of 0.0 to 1.0, but will be small in most applications. For instance, in the TKX assay, the average background intensity is typically about 0.006. In the fluorescein dilution series used to test the light detection device presented above, the buffer wells are roughly the same brightness as 6 pM fluorescein, so that f is about 0.06 when compared with our performance specification of 100 pM.

A potential advantage of the anisotropy-based procedure is that it may be more robust than the intensity-based procedure. If intensities vary for some reason, such as a change in lamp power or alignment, the intensity-based background-subtraction procedure may give erroneous results. However, the anisotropy-based background-subtraction procedure will still give correct results because the background anisotropy and relative background intensity should remain unchanged.

Propagation of error. We want to be sure that anisotropy-based background subtraction does not introduce unacceptably high errors into our results. Error propagation can be estimated by $$\Delta R_L = \sqrt{\left(\frac{1}{1-f_0}\right)^2 (\Delta R_T)^2 + \left(\frac{f_0}{1-f_0}\right)^2 (\Delta R_0)^2 + \left(\frac{R_T - R_0}{(1-f_0)^2}\right)^2 (\Delta f_0)^2} \tag{10}$$

For small $f_0$, this simplifies to $$\Delta R_L = \sqrt{(\Delta R_T)^2 + f_0^2 (\Delta R_0)^2 + (R_T - R_0)^2 (\Delta f_0)^2} \tag{11}$$

This equation shows that:
1. Errors in $R_T$ (instrument errors) translate directly into errors in $R_L$.
2. Errors in the background anisotropy have only a small effect on our determination of $R_L$; for instance, if $f_0$ is 0.01 and $\Delta R_0$ is 0.1 (150 mP), the effect on RL is <0.001 (1.5 mP).
3. Errors in $f_0$ (hot well) give appreciable errors in $R_L$ whenever $R_T$ and $R_0$ are significantly different. For instance, if $R_T=0.1$, $R_0=0.4$ and $\Delta f_0=0.1$, the error in $R_L$ is <0.03 (45 mP).

Note that $\Delta R_L$ skyrockets when the background is bright. For instance, if the background and label have equal brightness ($f_0=0.5$), then $$\Delta R_L = \sqrt{(2\Delta R_T)^2 + (\Delta R_0)^2 + (R_T - R_0)^2 (4\Delta f_0)^2} \tag{12}$$

This may explain why the current lower-detection limit (LDL) of the fluorescein polarization is about 30 pM; because the background has a brightness of about 6 pM, the errors begin to accumulate as we approach this concentration.

Application: treated plates for control of hot wells in polarization. Assume that we an fabricate or treat microplates in such a way that their background anisotropy is controllable. For instance, we could add some titanium dioxide to a black plate to cause scattering, which would reduce background polarization. Specifically, consider a plate designed to work with the TKX assay. In the TKX assay, we look for a decrease in anisotropy from a nominal value of 0.100 (140 mP) to some lower value. The plate is designed with a background anisotropy of about 0.100 (140 mP) so that it provides a background that matches the assay. Now we sec from Equations 8 and 9 that all "non-hit" wells give $R_T=R_L=R_0=0.100$.

Next, look at the behavior of a hot well. It can be extremely bright, say $f_0=05$, but because its anisotropy is the same as background, it is not detected as a "hit," because by Equations 8 and 9 it still gives $R_T=R_L=R_0=0.100$. This hot-well immunity is also evidenced in Equation 12: when $R_T$ and $R_0$ are about the same, errors in $f_0$ (hot wells) do not propagate to $R_L$.

If it is not technically feasible to make microplates with controlled anisotropy, then the same effect might be achieved by adding polarized components to the assay chemistry to achieve the desired background anisotropy.

Experimental results. Six 96-well microplates were filled with PBS (250 μL/well) and read on Analyst S/N E003. The following table shows intensity and polarization data for each plate.

| Plate | ∥ Channel cps | | ⊥ Channel cps | | Polarization (mP) | |
|---|---|---|---|---|---|---|
| | Avg | StDev | Avg | StDev | Avg | StDev |
| white plate | 616624 | 20276 | 637303 | 19092 | 8 | 14 |
| black plate 1 | 49303 | 2272 | 17369 | 1212 | 498 | 18 |
| black plate 2 | 48805 | 1257 | 16718 | 525 | 508 | 14 |
| black plate 3 | 48907 | 1471 | 16984 | 799 | 503 | 18 |
| black plate 4 | 48401 | 1122 | 16647 | 478 | 506 | 14 |
| black plate 5 | 48581 | 1484 | 16833 | 810 | 504 | 17 |

The data indicate that:
1. The background polarization of the of the black plates is very high (about 500 mP).
2. The background polarization of the of the black plates is consistent from plate to plate.
3. The background polarization of the white plate is very low.

These data indicate that background anisotropy could be measured less frequently. Moreover, the consistency in the ∥ and ⊥ intensities suggests that a similar approach could be implemented with our current intensity-based background-subtraction methodology. That is, ∥ and ⊥ channel background intensities could be measured less frequently than every plate.

In other experiments, the background (buffer well) intensity was compared with that of fluorescein. Four different plates were read on 4 different Analyst units. In all cases, the brightness was similar (about 6 pM fluorescein), even though different instruments were used.

|  | Buffer brightness (pM) | |
|---|---|---|
| Unit | 96 wells | 384 wells |
| AN0085 | 4.8 | 4.0 |
| AN0086 | 7.8 | 4.9 |
| AN0088 | 5.1 | 4.5 |
| AN0090 | 6.8 | 6.4 |

FLAMe method. Another method to remove unwanted fluorescence background is to employ the fluorescence lifetime anisotropy method (FLAMe). This method can eliminate the effect of background fluorescence in a polarization assay if the background has an average lifetime distinct from the analyte lifetime.

FLAMe uses the time-resolved fluorescence anisotropy measured in the frequency domain to distinguish the long and short lifetime components. The measurement is then manipulated to establish the ratio of bound probe molecules to the sum of the bound and free molecules (the faction of bound molecules). The goal of the method is to establish a way to measure the fraction of bound molecules (or free ones) without interference from other fluorescing compounds.

Derivation of the FLAMe method. The lifetime discriminated intensity (LDI) may be used for the rejection of short lifetime background when a long lifetime analyte is used (also the reverse is possible). The LDI can be substituted anywhere a conventional intensity would be used. For a polarization assay, the LDI of the parallel intensity and the LDI of the perpendicular intensity can replace the parallel and perpendicular intensity values used to calculate the polarization (or anisotropy).

$$P = \frac{(LDI_\parallel) - G(LDI_\perp)}{(LDI_\parallel) + G(LDI_\perp)} \quad (13)$$

Figure 37:
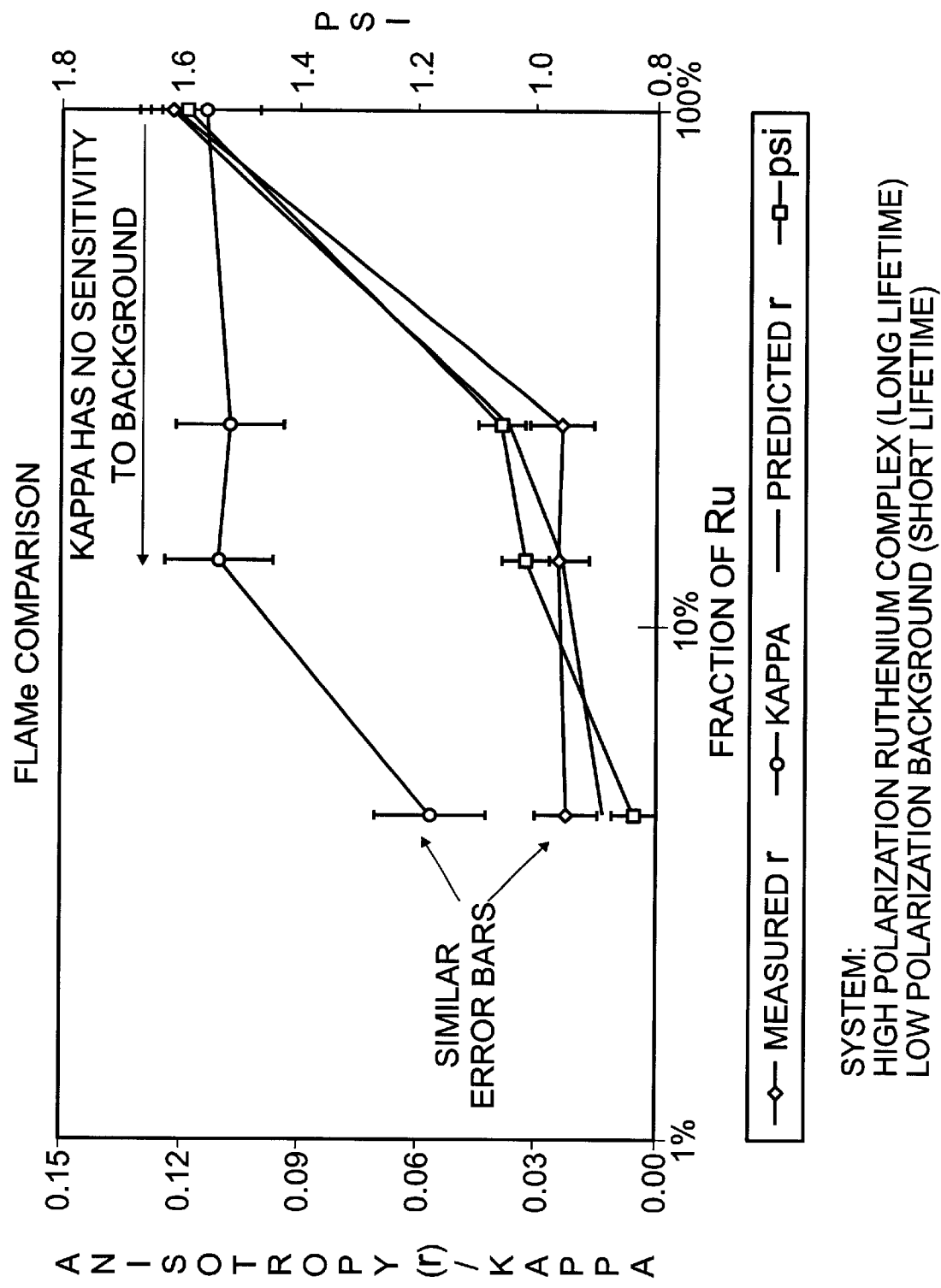
FIG. 37 is a graph of experimental results showing that short-lifetime background with low polarization docs not significantly affect performance of FLAMe methods.

FIG. 37 shows using experimental results that short-lifetime background with low polarization does not significantly affect performance of FLAMe methods.

B. Intensity Assays

The apparatus and methods provided by the invention can be used to discriminate between analyte and background in intensity assays. Background-corrected intensities derived from such intensity assays can be used directly, as intensities, or they can be used indirectly to determine quantities such s polarization and luminescence lifetime. Generally, the invention permits determination of background-corrected intensities for systems having one or more analytes and one or more background components.

Two-component analysis. In systems having two detectable components, such as analyte and background, the contribution of each component to the total intensity can be determined using the intensity, phase, and modulation of the system, measured at a single angular modulator frequency ω. This embodiment of the invention may be termed lifetime-discriminated intensity (LDI).

In the time domain the luminesence of a complex luminophore or of a mixture of luminophores normally decays as a series of exponentials.

$$I(t) = \sum_i \alpha_i e^{-t/\tau_i} \quad (14)$$

Here, I(t) is the time-dependent luminescence intensity, $\alpha_i$ is a preexponential factor, and $\tau_i$ is the luminescence lifetime of the ith component. The fraction of the steady-state luminescence intensity contributed by each component may be found by integrating Equation 14 over time.

$$f_i = \alpha_i \tau_i / \sum_j \alpha_j \tau_j \quad (15)$$

Here, $f_i$ is the fractional intensity of the ith component.

In the frequency domain, the phase and modulation phasor of a complex luminophore or a mixture of luminophores is a vector sum of the phase and modulation of the individual components, weighted by the individual components' fractional contributions to the total intensity.

Figure 38:
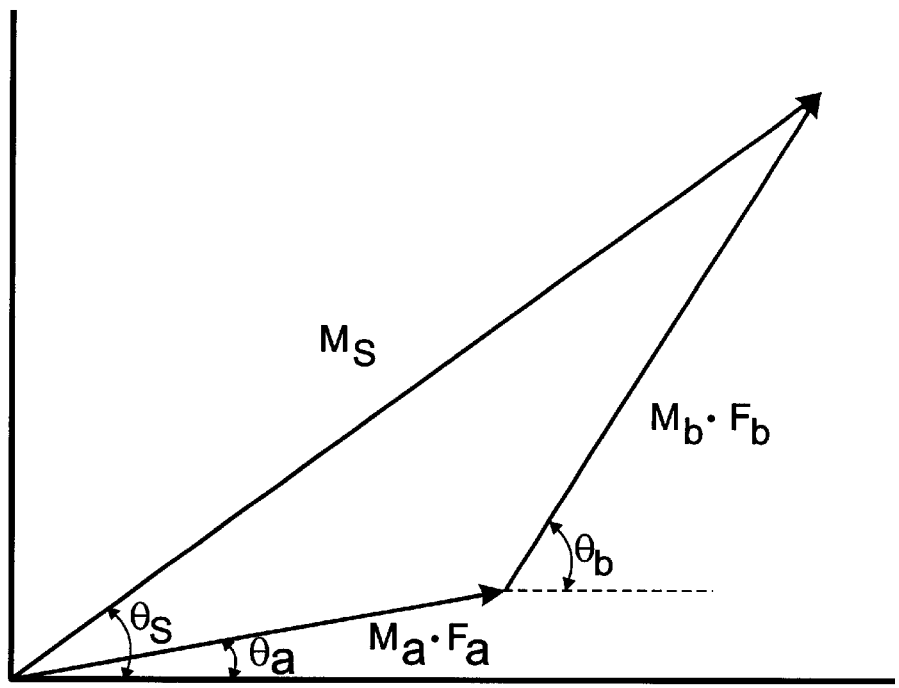
FIG. 38 is a phasor diagram showing phase and modulation phasors for a system having an analyte and background.

FIG. 38 shows phase and modulation for a system containing two luminophores, such as an analyte and background. The phase and modulation of the system can be expressed in terms of X Mnd Y components of the phasor.

$$M_s = \sqrt{M_{s,x}^2 + M_{s,y}^2} \quad (16)$$

$$\phi_s = \arctan\left(\frac{M_{s,y}}{M_{s,x}}\right) \quad (17)$$

Here 's' denotes system, and 'x' and 'y' denote X and Y components. The X and Y components for the system can be expressed in terms of X and Y components for the analyte and background alone.

$$M_{s,x} \equiv M_s \cdot \cos \phi_s = f_a \cdot M_a \cdot \cos \phi_a + (1-f_a) \cdot M_b \cdot \cos \phi_b \quad (18)$$

$$M_{s,y} \equiv M_s \cdot \sin \phi_s = f_a \cdot M_a \cdot \sin \phi_a + (1-f_a) \cdot M_b \cdot \sin \phi_b \quad (19)$$

Here 'a' denotes analyte, and 'b' denotes background.

Equations 18 and 19 can be rearranged to solve for the fractional intensities of the analyte and background. The fractional intensity $f_a$ of the analyte is $$f_a = \frac{M_{b,i} - M_{s,i}}{M_{b,i} - M_{a,i}} \quad (20)$$

Here 'i' denotes x or y, corresponding to X or Y components. To calculate fractional intensity using Equation 15, three quantities must be known: $M_{s,i}$, corresponding to the system; $M_{a,i}$, corresponding to analyte alone; and $M_{b,i}$, corresponding to background alone. $M_{s,i}$ is determined for each sample, by making a measurement on each sample. $M_{a,i}$ is determined for each analyte, not for each sample, either (1) by measuring the modulation phasor using a blank containing the analyte "without" background (possibly at high concentration), or (2) by calculating the modulation phasor using Equations 4–5 and the analyte lifetime as measured above without background. This is applicable in the case where the analyte is the same but the background is different in every sample (as in high-throughput screening (HTS)). $M_{b,i}$ may be estimated for each sample by making a measurement on a blank for each sample. In HTS, $M_{b,i}$ typically varies from sample to sample, because the background includes contribution from the composition. An alterative method leading to larger errors in HTS would be to measure an average background using a single blank ($M_{b,i}$) and to apply this background to each sample.

The apparatus and methods provided by the invention allow a more elegant and accurate solution to background correction, which does not require the use of a blank. Equation 20 can be rewritten as a power series of $\omega\tau_b$ or $1/\omega\tau_b$ (assuming that the background follows a single exponential decay). The motivation for the power series is that the power series can be conveniently truncated if the background has a short lifetime ($\omega\tau_b \ll 1$) or if the background has a long lifetime ($1/\omega\tau_b \ll 1$). If the background has a short lifetime, the analyte fractional intensity is $$f_a = \frac{1-M_{s,x}}{1-M_{a,x}} + \frac{M_{a,x}-M_{s,x}}{(1-M_{a,x})^2} \cdot (\omega\tau_b)^2 + \ldots \xrightarrow{\omega\tau_b \to 0} \frac{1-M_{s,x}}{1-M_{a,x}} \quad (21)$$

If the background has a long lifetime, the analyte fractional intensity is $$f_a = \frac{M_{s,x}}{M_{a,x}} + \frac{M_{s,x}-M_{a,x}}{M_{a,x}^2} \cdot \frac{1}{(\omega\tau_b)^2} + \ldots \xrightarrow{\omega\tau_b \to \infty} \frac{M_{s,x}}{M_{a,x}} \quad (22)$$

Equations 21 and 22 discriminate between light emitted by the analyte and short- or long-lifetime background, based on differences in lifetime, without requiring the lifetime or intensity of the background. If the value of the background lifetime is only known to be short (as compared to the frequency), we =mploy the limiting case of Eq. 21. Likewise, if the background lifetime is only known to be long, we employ the limiting case of Eq. 22. When the background lifetime is better known (yet, still short or long), higher order terms in Eq. 21 and 22 may be calculated and used to yield a better approximation.

Although both the X and Y versions of Eq. 20 are valid, it is more fruitfull to make approximations with the X version because the X expansions only have nonzero terms with even powers of the background lifetime (or inverse lifetime, as appropriate),whereas the Y expansions have all powers of the background lifetime (or inverse lifetime, as appropriate). Thus, when an approximation is made, the order of the first neglected term in the X case always will be equal to or higher than the first neglected term in the Y case. The modulation- and phase-based equations for $f_a$ (not shown) behave in tile same way as the equations in the Y case, in that all powers of the background lifetime are included in the expansion. For example, in a phase-based formulation, if the background has a short lifetime, the analyte fractional intensity is $$f_a = \frac{\tan\phi_s}{M_{a,y}+(1-M_{a,x})\cdot\tan\phi_s} + \frac{M_{a,y}+(2-M_{a,x})\cdot\tan\phi_s}{(M_{a,y}+(1-M_{a,x})\cdot\tan\phi_s)^2} \cdot \omega\tau_b + \ldots \quad (23)$$

However, the phase-based approach has a potential advantage. If only the phase is desired, a device could be optimized to measure just the high-frequency (AC) intensity or phase without measuring the average (DC) intensity. With the elimination of DC electronics, the device is likely to be more stable electronically and to provide a more precise measurement. This increased precision may allow the frequency to be reduced so that the neglected terms in the phase approach (Eq. 23) become comparable to those in the modulation phasor approach (Eq. 21). This increase in precision may even make the phase approach preferable to the modulation phasor approach.

Variations in the excitation intensity and lifetime of the background do not affect the determination of $f_a$, to the extent that the background lifetime remains small or large, as appropriate. This is true even if the background includes multiple components, as long as the lifetime of each component is short (Equations 21 and 23) or long (Equation 22). In these cases, the average or effective lifetime of the background may be used in Equations 21–23 as needed.

Alternative versions of Eq. 21 and 22 can formulated by creating a power series in $\tau_b/\tau_a$ (for short-lifetime background) or $\tau_a/\tau_b$ (for long-lifetime background) from Eq. 20. For example, the short-lifetime expansion is $$f_a = \frac{1-M_{s,x}}{1-M_{a,x}} + \frac{M_{a,x}-M_{s,x}}{M_{a,x}\cdot(1-M_{a,x})} \cdot \left(\frac{\tau_b}{\tau_a}\right)^2 + \ldots \quad (23a)$$

This expansion demonstrates that the lifetime ratio has as much effect on the approximation as does the background lifetime, frequency product. The lifetime ratio expansion also may prove useful if one knows the lifetime ratio better than the absolute lifetime of the background and a second order correction is desired.

Three-component analysis. Sometimes the background has both short- and long-lifetime components. In these cases, the two-component models of Eq. 21–23a will incorrectly report the fractional analyte intensity because the unexpected background (either Ions or short lifetime, depending on the equation) will be mixed with the analyte signal. In such situations, a three-component analysis should be used.

In a system having three detectable components, such as an analyte and both short- and long-lifetime backgrounds, the contribution of each component to the total intensity can be determined using the intensity, phase, and modulation of the system, measured at two angular modulation frequencies ($\omega_1, \omega_2$). In this case, the fractional intensity of the analyte is $$f_a = p(\omega_1) - q(\omega_1) \cdot \frac{p(\omega_2)-p(\omega_1)}{q(\omega_2)-q(\omega_1)} \quad (24)$$

$$p(\omega) \equiv \frac{1-M_{s,x}}{1-M_{a,x}} + \frac{M_{a,x}-M_{s,x}}{(1-M_{a,x})^2} \cdot (\omega\tau_{bs})^2 + \ldots \quad (25)$$

$$q(\omega) \equiv \frac{\frac{1}{(\omega\tau_{bl})^2}-1}{1-M_{a,x}} + \frac{\frac{1}{(\omega\tau_{bl})^2}-M_{a,x}}{(1-M_{a,x})^2} \cdot (\omega\tau_{bs})^2 + \ldots \quad (26)$$

Here 'bs' and 'bl' denote short- and long-lifetime background, respectively. As with the two-component models, we believe that the best mode is the modulation phasor approach with the X component. The reasons for this choice and the benefits are the same as described above. Additionally, the other approaches (such as the phase approach) sXi 1 are valid and would appear to have the same benefits and limitations as described above. If the short- and/or long-lifetime background include multiple components, the average or effective lifetime of the short components and the average or effective lifetime of the long components should be used for $\tau_{bs}$ and $\tau_{bl}$, respectively. This embodiment of the invention may be termed lifetime-resolved fractional intensity.

Practical considerations. The methods to reduce background luminescence outlined above have all determined the fractional intensity of the analyte. In most operations, the quantity of interest is not the analyte fractional intensity but the analyte intensity, which is the total intensity times the fractional intensity. We term the product of the total intensity and the fractional intensity given by Eq. 20–23a (single-frequency, two-component) the lifetime discriminated intensity (LDI). We term the product of the intensity and the fractional intensity given by Eq. 24 (dual frequency, three-component) the lifetime-resolved intensity (LRI).

Figure 39:
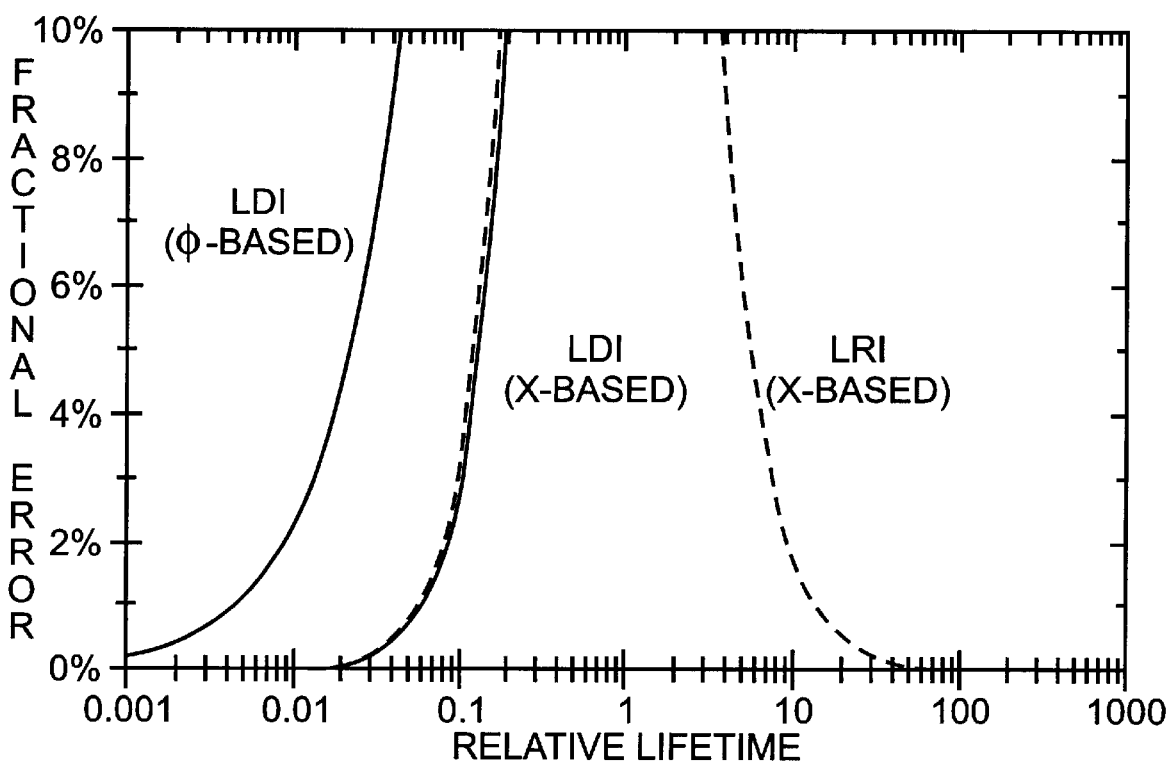
FIG. 39 is a graph of simulation results showing how the invention discriminates between an analyte and background for three zeroth-order embodiments of the invention, as described in Equations 13 (LDI, $M_x$-based), 15 (LDI, φ-based), and 16 (LRI).

FIG. 39 shows simulation results demonstrating the ability of the invention to discriminate between an analytic and a background. Results are shown for three zeroth-order embodiments of the invention, as described in Equations 21 (LDI, $M_x$-based), 23 (LDI, $\phi$-based), and 24 (LRI). The error is determined by the choice of frequency and analyte lifetime. When the lifetimes of the analyte and background differ by more than a factor of ten for the equations based on the X components of the modulation, the error is low enough (<2%) for HTS applications.

The choice of frequency also is important for small systematic errors. In the lifetime-discriminated case (Equation 21), the frequency must be chosen so that the measured quantity ($M_{s,x}$) is useable. The errors in $M_{s,x}$ must not translate into a large uncertainty in the derived fractional intensity. If the fraction of analyte is large, any frequency appropriate for measuring the analyte will suffice. For example, if the analyte has a lifetime of 100 nanoseconds, any frequency in the range of 300 kHz to 8 MHz is appropriate (from ⅕ to 5x the inverse lifetime).

If the fraction of analyte is low, however, the frequency selection is constrained by the fact that $M_{s,x}$ is dominated by the short lifetime background. Its value will be too close to the upper limit (1.000) if the frequency; too small. A normal value for the error in M would be 0.005. With this size error, it is not reasonable to make a precise measurement of M when its value is greater than 0.980. This upper limit will make low frequencies unusable. For a ruthenium-complex analyte having a lifetime of 360 nanoseconds and a background having a lifetime of <5 nanoseconds, a reasonable frequency is 2–3 MHz.

In the lifetime-resolved case (Equation 25), the choice of frequencies is more difficult. Roughly, one frequency is needed to discriminate between the long and intermediate lifetimes, and one frequency is needed to discriminate between the intermediate and short lifetimes. Each frequency may be chosen as for a two-component system. However, using an optimization program to choose the frequencies may be more reliable and robust. The program optimizes the frequencies to minimize systematic error due to finite lifetime 5 of the short and long components, while also minimizing the error due to changes in analyte lifetime.

Experimental verification. The luminescence intensity due to the analyte can be found by multiplying the total intensity by the calculated fractional intensity, using Equations 20 (LDI), 22 (LDI), or Equation 23 (LRI), among others. Total intensity is obtained from the steady-state value of the luminescence emission, without performing a separate experiment. To test these concepts, we built a phase and modulation fluorometer capable of measuring samples in a microplate, as described above. The instrument uses epi-luminescence geometry, an intensity-modulated blue LED, and a gain-modulated PMT.

Experiments were conducted to assess the ability of the apparatus and methods to discriminate between analyte and background. The analyte was $[Ru(bpy)_3]Cl_2$ (ruthenium tris-2,2'-bipyridyl chloride), which has a long lifetime in buffer (measured at 330 nanoseconds at a temperature of 26–28° C. in 20 millimolar PBS, pH 7.4). The background was from the sample container and/or added R-phycoerythrin. R-phycoeydirin was used as an intentional background contaminant because its excitation and emission spectra overlap those of $Ru(bpy)_3$ and because it hag a short lifetime in buffer (measured at 2.9 nanoseconds in 20 millimolar PBS, pH 7.4). All samples were prepared with 20 mM PBS, pH 7.4, and all data were collected with a 400 millisecond integration time in COSTAR-brand flat-black 96-well microplates.

Ruthenium is a good long-lifetime probe for several reasons. First, ruthenium has a long lifetime. Second, ruthenium's lifetime is not extremely sensitive to oxygen concentration, even though ruthenium sometimes is used as an oxygen sensor. This is because ruthenium's lifetime is short relative to good oxygen sensors. In particular, ruthenium's lifetime is not particularly sensitive to normal changes in oxygen content in air-equilibrated buffer, so that no special measures must be taken to remove oxygen from the system. Third, ruthenium is an atomic luminophore, so that it is not subject to the common problem of photobleaching. Finally, the ruthenium complex has a convenient excitation spectrum (460 nanometer peak) and a large (140 nanometer) Stokes' shift. (The Stokes' shift is the separation between maxima in excitation and emission spectra.)

Conventional background subtraction fails when the background concentration is too large due to fluctuations in background intensity and variations from sample to sample. A 1% variation between samples will make it impossible to measure an analyte whose intensity is only 1% of the background signal. To have confidence that a signal exists, a three standard-deviations rule may be used. The minimum resolvable signal is defined as a signal that is three standard deviations larger than the average background.

For a background-subtracted value, our confidence limit translates to a fractional error (or coefficient of variation, CV) of about 47%. (Both sample and background were assumed to have the same error with the difference three times the error; $CV=\sqrt{3/2}$.) Such a large CV is usable only for qualitative measurements. For quantitative measurements, a smaller CV is desired. Typical dispensing errors, concentration errors, and instrument drift can combine to give an error of several percent. Considering these other errors, it is practical to use data with a 10% CV for quantitative work, which may be considered the limit for precise data. These confidence and precision limits allow quantitatively comparison of data from background-subtracted intensity, lifetime-discriminated intensity, and lifetime-resolved intensity measurements.

Figure 40:
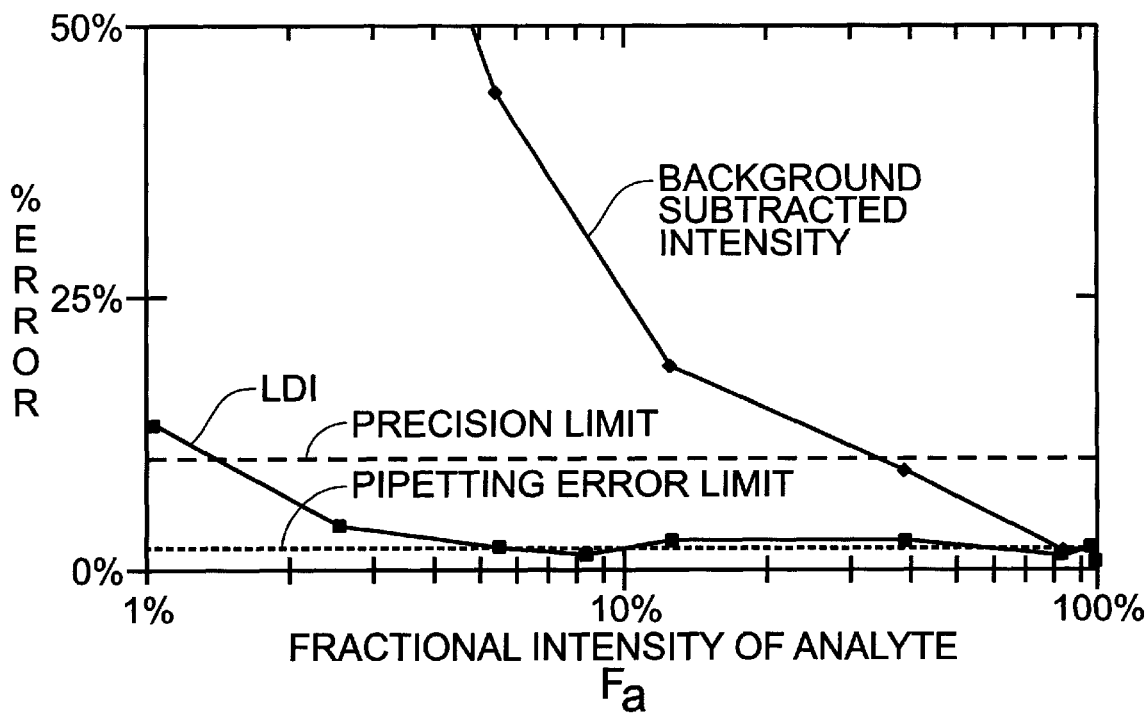
FIG. 40 is a graph of experimental results showing how the invention discriminates between a long-lifetime ruthenium-complex analyte and a short-lifetime R-phycoeiythrin background, for a constant concentration of analyte and an increasing concentration of background. Results are shown for embodiments described under FIG. 39.

FIG. 40 shows experimental results demonstrating sensitivity to background, determined by adding increasing concentrations of R-phycoeiythrin to a constant concentration of $Ru(bpy)_3$. The result was a series of solutions with increasing total intensity but constant analyte intensity. All solutions were prepared in duplicate, and errors in the average were compared with expected values. FIG. 40 shows three curves. LDI corresponds to Equation 21, evaluated at 2.85 MHz. LRI corresponds to Equation 25, evaluated at $f_1$=0.35 MHz and $f_2$=4.33 MHz. BSI corresponds to the background-subtracted intensity, computed using a blank. The ability of a method to discriminate analyte and background is given by the analyte fractional intensity at which measurement error exceeds the confidence limit. The background-subtraction method can discriminate between analyte and background only if the analyte fractional intensity exceeds 17%, hereas LDI and LRI can discriminate between analyte and background if the analyte fractional intensity exceeds 2% and <0.8%, respectively. Therefore, both methods are less than one-tenth as responsive to background luminescence as background subtraction. This reduced responsivity is achieved while reducing experimental complexity. Under the proper conditions, LDI and LRI do not require any measurement of the background luminescence, including its lifetime and intensity. The contribution of background to the measured intensity is removed simply because of its short lifetime.

Figure 41:
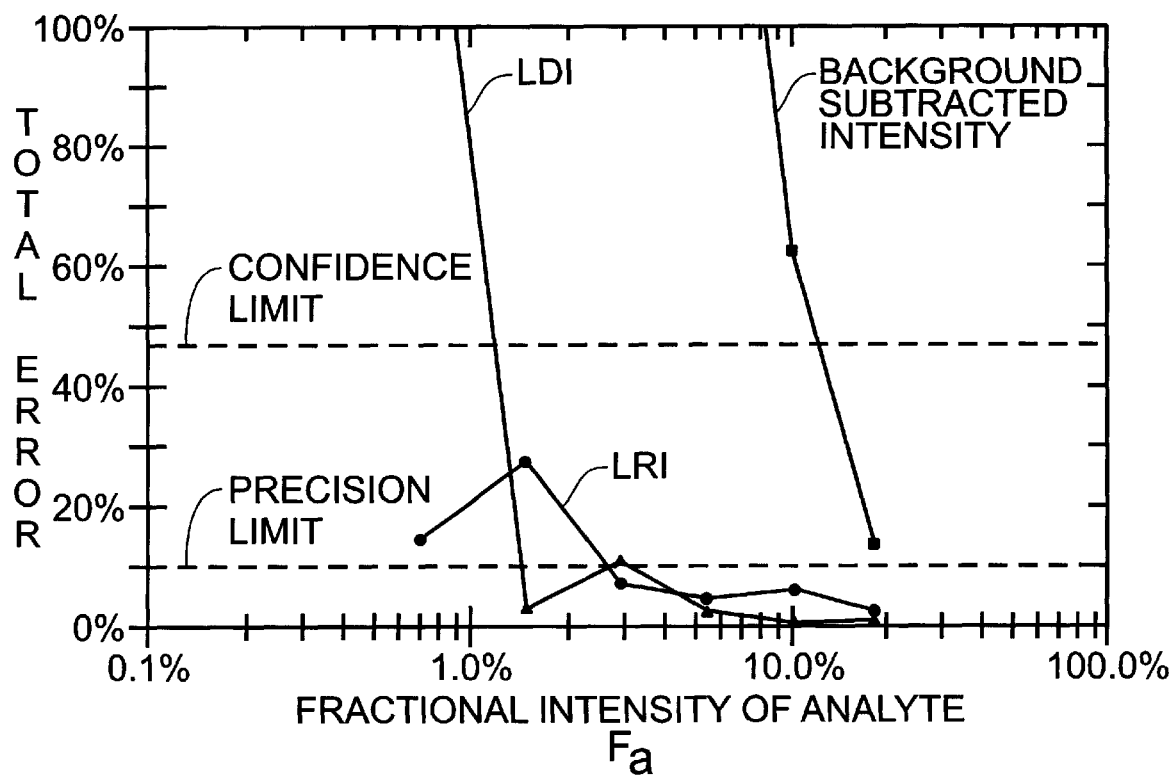
FIG. 41 is a graph of experimental results showing how the invention discriminates between a long-lifetime rutenium-complex analyte and a short-lifefime R-phycoetythrin background, for a constant concentration of background and an increasing concentration of analyte. Results are shown for embodiments described under FIG. 39.

FIG. 41 shows experimental results demonstrating sensitivity to analyte, determined by adding increasing concentrations of Ru(bpy)$_3$ to a constant (1 nanomolar) concentration of R-phycoeyrin. The result was a series of solutions with increasing total intensity but constant background intensity. This setup permits a determination of the minimum resolvable fraction of analyte in the presence of background. All solutions were prepared in duplicate, and errors in the average were compared with expected values. We measured the LDI was measured at 2.85 MHz, and LRI was measured at 0.35 and 2.85 MHz. The difference between methods is again substantial. Background subtraction quickly fails to resolve the analyte (at a fractional intensity of 13% or 100 micromolar of ruthenium complex). LDI reports the correct analyte intensity down to a factional intensity of 1% (10 $\mu$M), while LRI reports the correct intensity down to less than 0.7% (5 micromolar). This is a greater than tenfold increase in the sensitivity to the analyte for either method. These consistent results suggest that LDI and LRI measurements can be a significant improvement over conventional background subtraction.

The invention is robust, simple, and fast, making it ideal for high-throughput screening. LDI is able accurately to distinguish short- and long-lifetime components using phase and modulation at only a single frequency. LRI is able accurately to separate three lifetime components using phase and modulation at two frequencies. Extension to even more components also is possible. Knowledge of the lifetime of one component is used to determine the intensity of each component, without requiring a determination of the lifetime or intensity of the other component.

C. Polarization Assays

The apparatus and methods provided by the invention also can be used to discriminate between analyte and background in polarization assays. Generally, the invention permits determination of background-corrected polarizations for systems having one or more analytes and one or more background components.

Background-corrected steady-state polarizations (or anisotropies) may be determined using Equation 1, where $I_\parallel$ and $I_\perp$ may be determined using appropriate combinations of parallel and perpendicular excitation and emission polarizers, and the apparatus and methods described above for computing background-corrected intensities. Such corrections are important, because steady-state anisotropies are intensity-weighted averages of the anisotropies of all components present, so that background affects the measured anisotropies directly.

Background-corrected time-resolved polarizations (or anisotropies) may be determined using time-domain or frequency-domain techniques. In the time domain, background-corrected polarizations may be determined using Equation 1, where $I_\parallel$ and $I_\perp$ are replaced by $I_\parallel(t)$ and $I_\perp(t)$. In the frequency domain, background-corrected polarizations may be determined using appropriate combinations of parallel and perpendicular phase $\phi_p$ and parallel and perpendicular modulation MP. Here 'p' denotes parallel or perpendicular, corresponding to parallel and perpendicular components. $\phi_p$ and $M_p$ are determined using the same apparatus and methods as $\phi$ and M, with the addition of parallel and perpendicular polarizers, as appropriate. $\phi_p$ and $M_p$ may be rewritten in terms of $\omega$ and $I(t)$.

$$\phi_{p\omega} = \tan^{-1}(N_{p\omega}/D_{p\omega}) \tag{27}$$

$$M_{p\omega} = \sqrt{N^2_{p\omega}+D^2_{p\omega}}/J_p \tag{28}$$

$$J_p = \int_0^\infty I_p(t)\,dt \tag{29}$$

$$N_{p\omega} = \int_0^\infty I_p(t)\sin(\omega t)\,dt \tag{30}$$

$$D_{p\omega} = \int_0^\infty I_p(t)\cos(\omega t)\,dt \tag{31}$$

Experimental results may be interpreted using a differential phase angle $\Delta_\omega$ and a ratio $\Lambda_\omega$ of he parallel and perpendicular AC components of the polarized emission.

$$\Delta_\omega = \phi_{\perp\omega} - \phi_{\parallel\omega} \tag{32}$$

$$\Lambda_\omega = \frac{AC_\parallel}{AC_\perp} = \frac{\sqrt{N^2_{\parallel\omega}+D^2_{\parallel\omega}}}{\sqrt{N^2_{\perp\omega}+D^2_{\perp\omega}}} \tag{33}$$

$\Lambda_\omega$ may be used to define a frequency-dependent quantity $r_\omega$, called the modulated anisotropy.

$$r_\omega = \frac{\Lambda_\omega - 1}{\Lambda_\omega + 2} \tag{34}$$

$r_\omega$ tends to the fundamental anisotropy $r_o$ at high frequency and to the steady-state anisotropy $r_{ss}$ at low frequency.

Frequency-domain time-resolved polarization may be used to investigate the motional properties of biological molecules in more detail than steady-state polarization. For example, a biophysical model may be used to generate functional forms of $I_\parallel(t)$ and $I_\perp(t)$, using parameters such as lifetimes and rotational correlation times. This model can be used to predict $\Delta_\omega$ and $\Lambda_\omega$. Experiments then can be done to measure $\Delta_\omega$ and $\Lambda_\omega$, at one or more modulation frequencies. Experimental results may be fitted to the model by adjusting the parameters to give the best fit between predicted and observed values of $\Delta_\omega$ and $\Lambda_\omega$ or $r_\omega$, for example, by using nonlinear least-squares optimization algorithms.

Alternatively, a simpler approach may be used, in which experiments are conducted at one or a few modulation frequencies, and experimental results are interpreted without resort to fitting to detailed models. Such an approach may be sufficient quickly to assay for significant changes in molecular mobility, for example, as occurs upon binding. Such binding may be to a target molecule as part of an assay, or to walls of the sample container, among others.

Figure 42A:
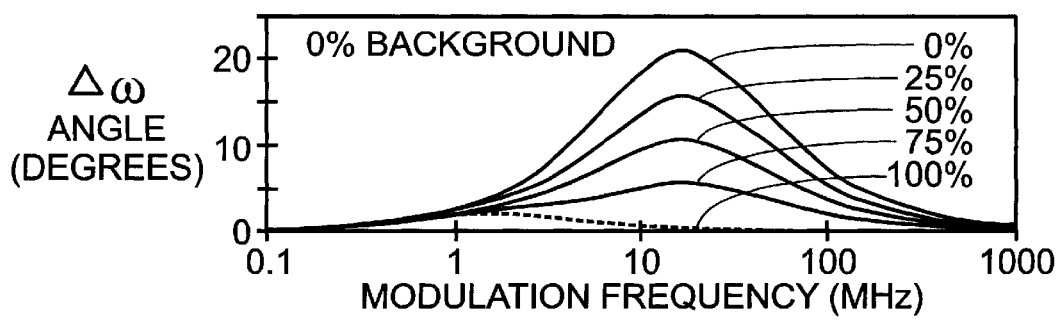
FIG. 42 is a graph of simulation results showing how binding affects differential phase (Panel A) and modulated anisotropy (Panel B) in the presence of 0% background in a frequency-domain binding experiment, for 0–100% binding as shown.
Figure 42B:
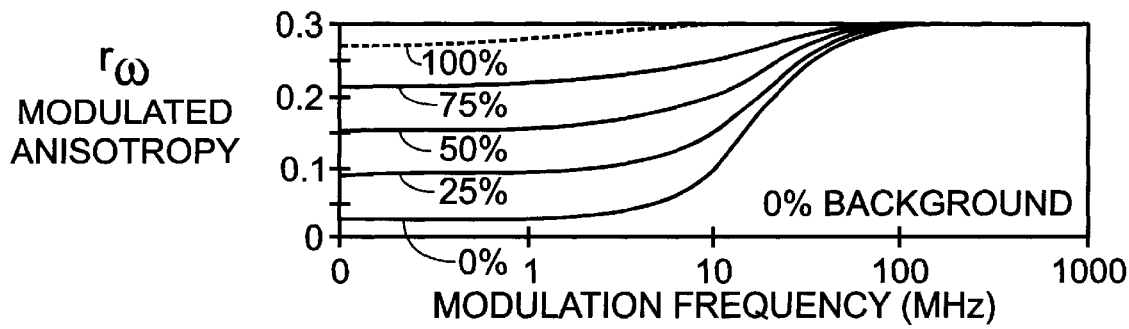

FIG. 42 shows how $\Delta_\omega$ (Panel A) and $r_\omega$ (Panel B) depend on $\omega$ for a simple binding system in the absence of background. Here, the labeled molecule has a fundamental anisotropy $r_o$=0.3, a luminescence lifetime $\tau$=100 nanoseconds, and a rotational correlation time $\tau_{rot}$=10 nanoseconds in the free state and 1000 nanoseconds in the bound state. FIG. 42 shows results for 0%, 25%, 50%, 75%, and 100% binding. The extent of binding of the labeled molecule can be determined quickly and sensitively by measuring $\Delta_\omega$ and $r_\omega$ at a single suitable frequency (e.g., ~20 MHz for $\Delta_\omega$, and <~10 MHz for $r_\omega$), and then reading off the extent of binding from an empirical calibration curve. Alternatively, binding could be determined using LDI and LRI, among others, if the binding is associated with a change in analyte lifetime.

Figure 43A:
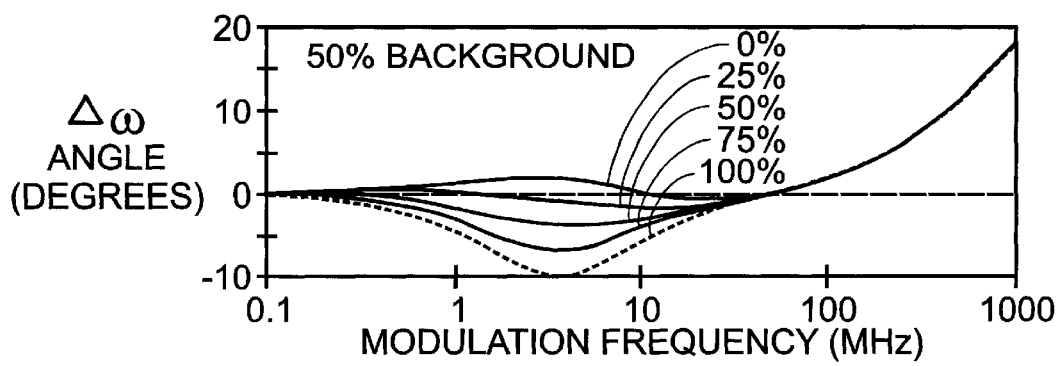
FIG. 43 is a graph of simulation results showing how binding affects differential phase (Panel A) and modulated anisotropy (Panel B) in the presence of 50% background in the frequency domain binding experiments shown in FIG. 42.
Figure 43B:
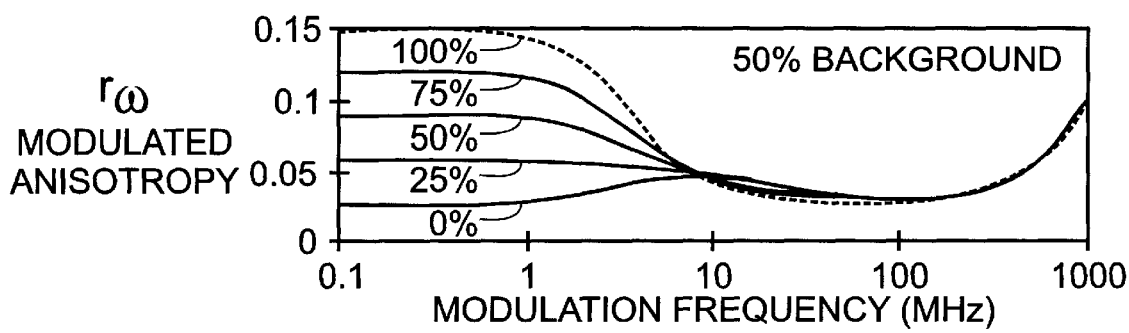

FIG. 43 shows how $\Delta_\omega$ (Panel A) and $r_\omega$ (Panel B) depend on $\omega$ for a simple binding system in the presence of 50% background. Here, the background has a fundamental anisotropy $r_o$=0.3 a luminescence lifetime $\tau$=1 nanosecond, and a rotational correlation time $\tau_{rot}$=0.1 nanosecond. These conditions correspond to compositions having a long-lifetime analyte and a short-lifetime background; the effective luminescence lifetime of the background usually is short, probably 0.1 to 10 nanoseconds. Unfortunately, a comparison of FIGS. 42 and 43 shows that there are no frequencies at which either $\Delta_\omega$ or $r_\omega$ is unaffected by the background. This greatly diminishes the utility of $\Delta_\omega$ or $r_\omega$, especially because background varies from sample to sample, and so generally cannot be included in a calibration curve.

These shortcomings are addressed by the invention, which provides alternative functions that better discriminate between analyte and background, without requiring information from a blank and without requiring a determination of the lifetime or intensity of the background. Two such functions, denoted "psi" and "kappa" fictions, are described below.

Psi function. The psi function, or $\Psi_\omega$, is a ratio of the parallel and perpendicular AC intensities, weighted by the sines of the parallel and perpendicular phases, respectively.

$$\Psi_\omega = \frac{AC_\| \sin(\phi_{\|\omega})}{AC_\perp \sin(\phi_{\perp\omega})} \tag{35}$$

$\Psi_\omega$ may be shown to be a ratio of the sine Fourier transforms $N_{p\omega}$ of the intensity decays in associated parallel and perpendicular measurements. To see this, simple trigonometry and the relationship $\phi_{p\omega}=\tan^{-1}(N_{p\omega}/D_{p\omega})$ give $$\sin(\phi_{p\omega}) = \frac{N_{p\omega}}{\sqrt{N_{p\omega}^2 + D_{p\omega}^2}} \tag{36}$$

Then, using Equation 36 defining $\Lambda_\omega$ gives $$\Psi_\omega = \frac{AC_\| \sin(\phi_{\|\omega})}{AC_\perp \sin(\phi_{\perp\omega})} = \frac{\sqrt{N_{\|\omega}^2 + D_{\|\omega}^2}}{\sqrt{N_{\perp\omega}^2 + D_{\perp\omega}^2}} \frac{\sin(\phi_{\|\omega})}{\sin(\phi_{\perp\omega})} = \frac{N_{\|\omega}}{N_{\perp\omega}} \tag{37}$$

Figure 44:
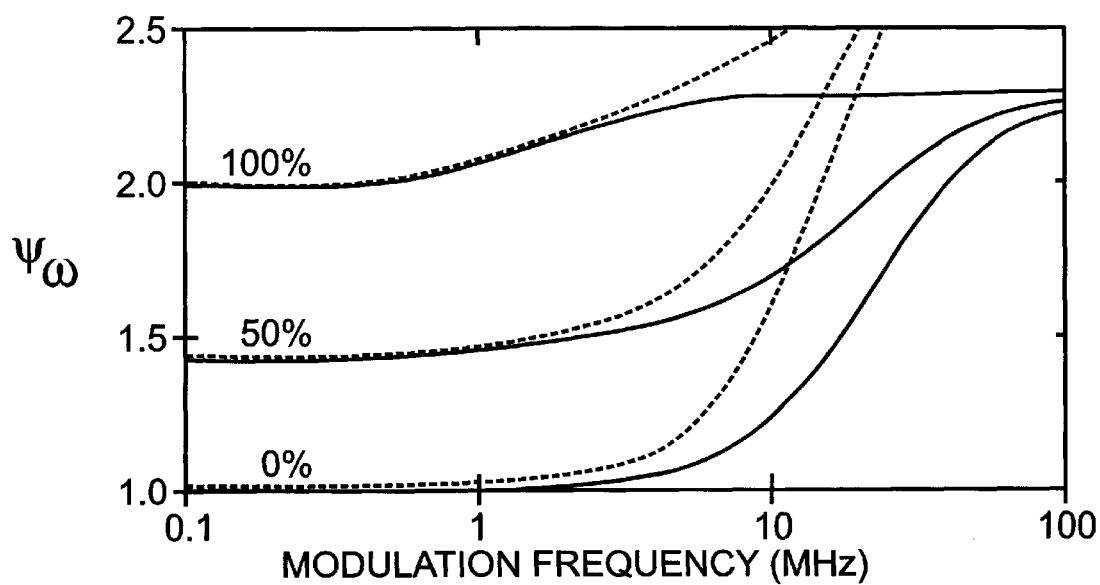
FIG. 44 is a graph of simulation results showing how binding affects $\Psi_\omega$ in the presence of 0% (solid lines) and 50% (dashed lines) background in the frequency-domain experiments of FIG. 42, for 0–100% binding as shown. $\Psi_\omega$ is defined and evaluated in accordance with the invention"

FIG. 44 shows how $\Psi_\omega$ depends on $\omega$ for the system of FIGS. 42 and 43, in the presence of 0% (Panel A) and 50% (Panel B) background. Generally, the lower the frequency, the less $\Psi_\omega$ is affected by the (short-lifetime) background. In particular, below $\omega$~10 MHz, $\Psi_\omega$ is much less affected by background than $\Delta_\omega$ and $r_\omega$. However, as $\omega$ becomes small, $\theta_p$ also becomes small, and measurement of the sine becomes imprecise. The optimum modulation frequency will be determined by a balance of these factors, among others.

The behavior of $\Psi_\omega$ for short-lived signals can be understood as follows. Assume that there are n molecular components, each with a single luminescence lifetime $\tau_i$ and a single rotational correlation time $\tau_{rot,i}$. The fraction of the steady-state luminescence intensity (no polarizers) contributed by each component is given by Equation 8. In the time domain, the anisotropy of each component is given by $$r_i(t) = r_{oi} e^{-t/\theta_1} \tag{38}$$

Then by the standard relationships $$I_\|(t) = \tfrac{1}{3}I(t)(1+2r_i(t)); \quad I_\perp(t) = \tfrac{1}{3}I(t)(1-r_i(t)) \tag{39}$$

Taking the sine Fourier transform gives $$N_{\|\omega} = \frac{1}{3}\left\{\sum_i \alpha_i \tau_i \left[L(\omega\tau_i) + 2r_{oi}\frac{\sigma_i}{\tau_i}L(\omega\sigma_i)\right]\right\} \tag{40}$$

$$N_{\perp\omega} = \frac{1}{3}\left\{\sum_i \alpha_i \tau_i \left[L(\omega\tau_i) - r_{oi}\frac{\sigma_i}{\tau_i}L(\omega\sigma_i)\right]\right\} \tag{41}$$

Here, $L(x)=x(1+x^2)$. For $|x|\ll 1$, $L(x)\sim x$ and $L(0)=0$. $L(x)$ reaches a maximum value of ½ at x=1. For $|x|\ll 1$, $L(x)\sim 1/x$, and $L(\infty)=0$. The rotational correlation time enters the system only through $$\sigma_i = \frac{\tau_i \theta_i}{\tau_i + \theta_i} \tag{42}$$

Because ½ min($\tau_i$, $\theta_i$)$\leq \sigma_i <$min($\tau_i$, $\theta_i$), $\sigma$ always is smaller than either $\tau$ or $\sigma$. The ratio $\sigma_i/\tau_i=\theta_i/(\tau_i+\theta_i)<1$. $\Psi_\omega$ can formed by taking a ratios of the N's and recalling that $$\alpha_i \tau_i = f_i \sum_j \alpha_j \tau_j.$$

$$\Psi_\omega = \frac{N_{\|\omega}}{N_{\perp\omega}} = \frac{\sum_i f_i \left[L(\omega\tau_i) + 2r_{oi}\frac{\sigma_i}{\tau_i}L(\omega\sigma_i)\right]}{\sum_i f_i \left[L(\omega\tau_i) - r_{oi}\frac{\sigma_i}{\tau_i}L(\omega\sigma_i)\right]} \tag{43}$$

Here, the normalizing sum canceled out of all the terms.

Based on the behavior of L(x) for small x, $\Psi_\omega$ gives small weight to signals from short-lived species ($\omega\tau_i$, or $\omega\sigma_i\ll 1$), in comparison to signals for which $\omega\tau_i$ or $\omega\sigma_i\sim 1$. $\Psi_\omega$ also gives small weight to the anisotropy contributions of long-lived components that have extremely short rotational correlation times (i.e., $\omega\sigma_i\ll 1$, $\sigma_i/\tau_i\ll 1$).

Kappa function. The kappa function, or $K_\omega$, is a ratio involving the parallel and perpendicular AC intensities, weighted in part by the cosines of the parallel and perpendicular phases, respectively.

$$K_\omega = \frac{I_\| - AC_\| \cos\phi_{\|\omega} - (I_\perp - AC_\perp \cos\phi_{\perp\omega})}{I_\| + AC_\| \cos\phi_{\|\omega} + 2(I_\perp + AC_\perp \cos\phi_{\perp\omega})} \tag{44}$$

$K_\omega$ may be shown to be a ratio involving lifetime-discriminated intensities, as defined above, in associated parallel and perpendicular measurements.

$$K_\omega = \frac{LDI_\parallel - LDI_\perp}{LDI_\parallel + 2LDI_\perp} \quad (45)$$

Equation 45 is analogous to anisotropy, a may be seen by comparing Equation 45 for $K_\omega$ with Equation 2 for r.

Figure 45:
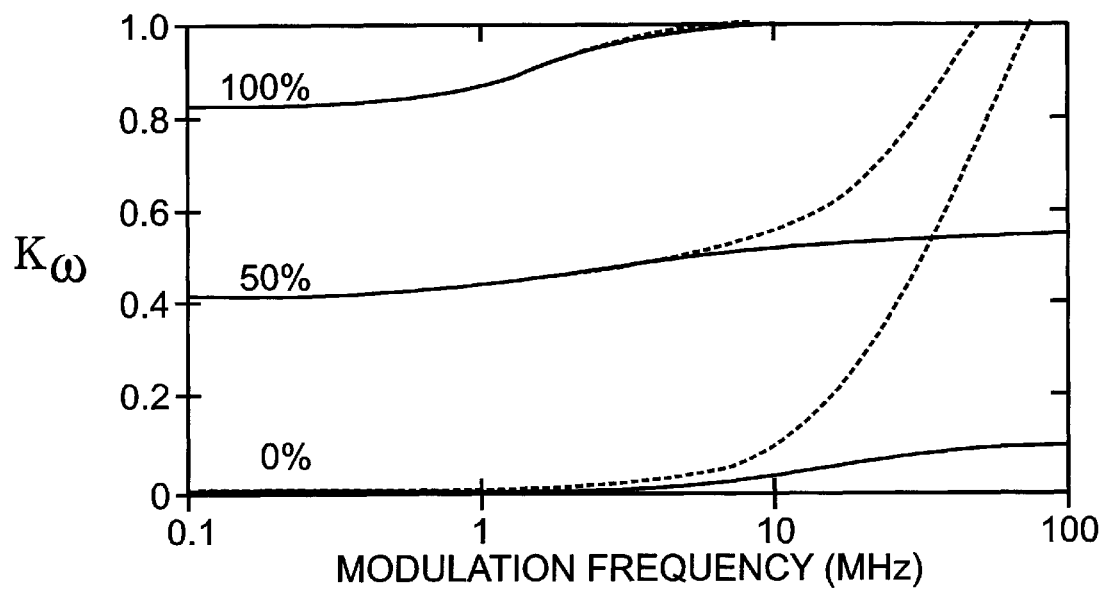
FIG. 45 is a graph of simulation results showing how binding affects $K_\omega$ in the presence of 0% (solid lines) and 90% (dashed lines) background in the frequency-domain binding experiments of FIG. 42. $K_{107}$ is defined and evaluated in accordance with the invention.

FIG. 45 shows how $K_\omega$ depends on $\omega$ for the system of FIGS. 42 and 43, in the presence of 0% (solid lines) and 90% (dashed lines) background. Results for $K_\omega$ are similar to results for $\Psi_\omega$, except that $K_\omega$ may be less sensitive than $\Psi_\omega$ to frequency for low frequencies, and to binding for high binding. Neither the kappa nor the psi function depends on properties of the background, so neither function requires use of a blank or a determination of the lifetime or intensity of the background.

D. Additional Methods

The invention provides additional new methods for discriminating between analyte and background in intensity (and thus indirectly in polarization) assays. Generally, these methods permit determination of background-corrected intensities for systems having one or more analytes and one or more background components. The remainder of this section is divided into three sections, which describe different methods provided by the invention: (A) "exact" algorithms for analyzing FLARe™ data, (B) correction of lifetime measurements for short-lived background, and (C) third-order FLDI (fluorescence lifetime discriminated intensity) algorithm for analyzing FLARe™ data.

"Exact" Algorithms for Analyzing FLARe™ Data. A sample in a fluorometric assay may contain multiple fluorescent components. Some are present intentionally, and the characteristics of their emissions form the basis of the assay. Others constitute background and interfere with the interpretation of the assay. Sources of background include the optical components of the detection instrument, contaminants in the sample container, and various components of the assay solution. Where the background is the game in every sample being assayed (e.g., a predictable emission from the sample container), a separate measurement coupled with background subtraction can sometimes improve performance. However, a particular problem occurs during high-throughput screening for new pharmaceuticals, where the library compound being assayed is fluorescent. Background subtraction would necessitate doubling the number of assays performed (true measurement and background measurement for each compound), and background subtraction is in any event of limited utility.

Here we describe how arbitrarily accurate solutions to realistic models for the time-dependent fluorescence of mixtures of fluorophores can significantly reduce the effects of background without requiring the preparation of additional samples containing library compounds for background analysis.

We retain the fairly standard nomenclature that we have used in previous patent applications involving FD measurements of the type discussed here:

$\nu$ modulation frequency in Hz
$\omega$ modulation frequency in radians/s,$=2\pi\nu$
$\tau$ lifetime in ns or s
$\theta$ phase angle (equivalent to $\phi$ above)
M modulation
n number of spectroscopically distinct types of fluorophores in the sample
$f_i$ fraction of the steady-state fluorescence contributed by the $i^{th}$ fluorophore For an FD measurement, we define the quantities:

$$N = f_1\omega\tau_1/[1+(\omega\tau_1)^2] + f_2\omega\tau_2/[1+(\omega\tau_2)^2] + \ldots f_n\omega\tau_n/[1+(\omega\tau_n)^2] \quad (46)$$

$$D = f_1/[1+(\omega\tau_1)^2] + f_2/[1+(\omega\tau_2)^2] + \ldots f_n/[1+(\omega\tau_n)^2] \quad (47)$$

Then it can be shown (see J. Lakowicz, *Principles of Fluorescence Spectroscopy*, $2^{nd}$ Ed., 1999) that the observed phase and modulation are:

$$\theta = \arctan(N/D); \quad (48)$$

$$M = (N^2 + D^2)^{1/2} \quad (49)$$

Estimates of the intensity and lifetime parameters can be extracted from phase and modulation measurements by, e.g., nonlinear least-squares fitting of predicted to observed data.

For this to work, the number of unknowns must in general not exceed the number of independent data points. There are at most 2n–1 unknowns (fractional intensities and lifetimes, reduced by one because the fractions must sum to unity). If reference measurements have already determined the values of parameters for individual components or subsets of components, this number can be reduced. The number of independent data points can be increased by making measurements at multiple modulation frequencies. For example, using two modulation frequencies generates four data points ($\theta$ and M each at two values of $\omega$).

In general, these solutions are numerical rather than analytical, and generating them may be time consuming computationally. Simplifications can result from the fact that it is not necessary to determine the parameters for background components, only to correct for the effects of background on the signal of interest. Various approximations in the equations can also simplify the computational task.

Correction of Lifetime Measurements for Short-Lived Background. A single FD measurement with angular modulation frequency $\omega$ gives, in addition to FLINT, modulation M and phase $\theta$ that can be used (starting from Equations 4 and 5) to calculate a mean lifetime $\tau$ for the sample:

$$\tau = \tan(\theta)/\omega \quad (50)$$

$$\tau = \sqrt{1/M^2 - 1}/\omega \quad (51)$$

If the fluorescence signal is produced by a single fluorophore exhibiting a single-exponential decay, these two equations yield the same value of the lifetime, the time constant for the decay.

When the fluorescence signal is more complicated, the two equations typically give different values of $\tau$. Relating the measurement to the underlying molecular processes is more complicated and in general requires measurements at multiple wavelengths or modulation frequencies that are interpreted by fitting to some model. For example, when there are two fluorophores with distinct lifetimes, the measured values of phase and modulatifon are weighted averages of the phase and modulation results that would be obtained in experiments on the separate components. Moreover, the weighting is different for phase and modulation. Two seperate FD measurements at appropriately chosen modulation frequencies are required to resolve the lifetimes and relative contributions to the FLINT of the two components.

The need to make multiple measurements on a sample slows the analytical process and is a disadvantage in applications, such as high-throughput screening, where it is important to minimize the assay time. Under some conditions, however, it is possible to resolve some of the molecular information from a complex sample with a single measurement.

For example, as shown above, it is possible to resolve the FLINT contributed by a long-lived label of interest in the presence of short-lived fluorescence background in a single FD measurement. This case has practical utility, because most fluorophores that contribute to contaminating background fluorescence in drug-discovery applications have lifetimes that are shorter than those of some of the available labels (especially metal-ligand complexes involving transition metals such as Ru, Os, and Re without limitation).

Here we report that under similar conditions, i.e., a label with a lifetime that is significantly longer than the lifetimes of all other contaminating signals, it is possible resolve the lifetime of that label in a single FD measurement, relatively free of interference from short-lived contaminants. This is contrasted with our previous work, which showed only that the FLINT of the label could be resolved from interference due to short-lived background.

The lifetime-measurement method that we describe here, which we call Fluorescence Lifetime Discriminated Lifetime (FLDL), is an approximation that works best when the ratio of background to label lifetimes is small and the ratio of background to label FLINT is small. However, when the lifetimes are well separated it is possible to resolve the label lifetime to a good approximation even when the FLINT from the background is significantly greater than that of the label.

Following is the theoretical development of the method.

Signals from an analyte A and background B combine to give the signal from the total system S. The lifetime of the analyte is $\tau_A$, and that of the background $\tau_B$. We assume that $\tau_B < \tau_A$, preferably $\tau_B << \tau_A$. We treat the background as a single component without significant loss of generality as long as the assumptions about lifetimes apply to all the background components (in which case the representation is of an averaged background).

Further definitions are: the fraction of the FLINT from the analyte is $f_A$. We define the quantities $X_i = M_i \cos(\theta_i)$ and $Y_i = M_i \sin(\theta_i)$, where i can equal A, B, or S. The values of $M_A$, $\theta_A$, $M_B$, and $\theta_B$ are those that would obtain if the A and B components were present separately.

From above, we know that under the restrictions on relative lifetimes imposed above the following two expressions hold to a good approximation:

$$f_A = (1-X_S)/(1-X_A) \tag{52}$$

and $$\tan(\theta_A) = Y_S/(X-1+f_A) \tag{53}$$

Substituting Equation 52 into Equation 53 gives $$\tan(\theta_A) = [Y_S/(1-X_S)] \cdot [(1-X_A/X_A)] \tag{54}$$

Now from elementary trigonometry and Equation 50 we hate $$\cos(\theta_A) = (1+(\omega\tau_A)^2)^{-1/2} \tag{55}$$

and $$M_A = (1+(\omega\tau_A)^2)^{-1/2} \tag{56}$$

so that $$X_A = (1+(\omega\tau_A)^2)^{-1} \tag{57}$$

and $$1-X_A = (\omega\tau_A)^2/(1+(\omega\tau_A)^2) \tag{58}$$

Substituting Equation 50 for component A along with Equations 57 and 58 into Equation 54 and rearranging to solve for $\tau_A$, we finally have $$\tau_A = (1-X_S)/Y_S = (1-M_S\cos(\theta_S))/(M_S\sin(\theta_S)) \tag{59}$$

In other words, we have an expression for the label lifetime $\tau_A$ purely in terms of quantities that can be obtained in a single FD measurement on the system that contains both analyte and background.

Figure 46:
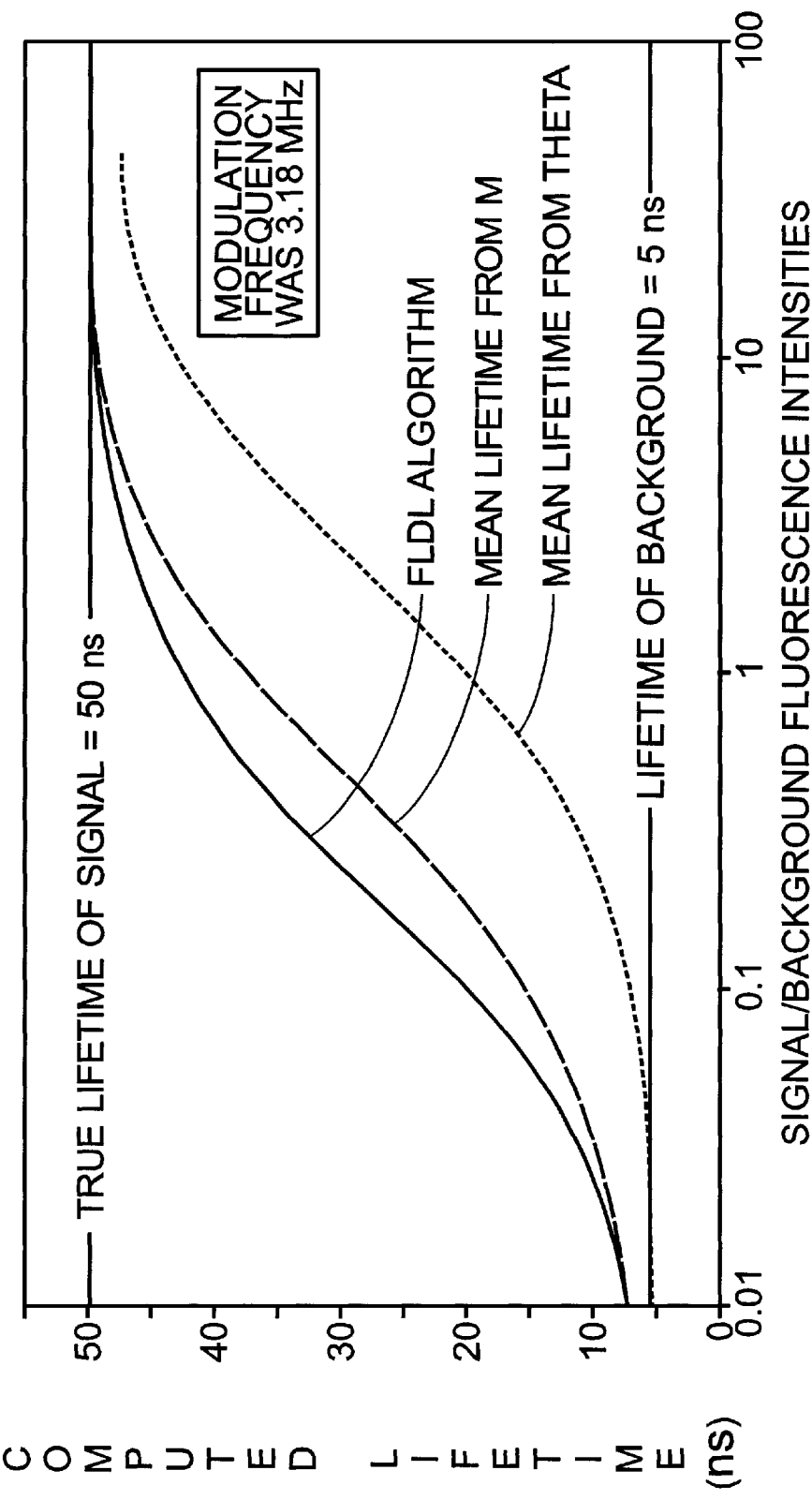
FIG. 46 is a graph of computed lifetime versus signal-to-background fluorescence intensities for simulated parameters, showing how the FLDL method improves the accuracy of lifetime measurement with strong backgrounds.

FIG. 46 shows the performance that can be expected of the algorithm, obtained using a simulation of FD experiments on a two-component system containing analyte (fluorescent label) and a fluorescent background in varying proportions. The FLDL algorithm demonstrates its superiority to the application of Equations 50 or 51 in that the lifetime of the analyte calculated with FLDL is much closer to the true value than the lifetime calculated with Equation (4) or (5) when there is appreciable background fluorescence.

Third-order FLDI (Fluorescence Lifetime Discriminated Intensity) Algorithm for Analyzing FLARe™ Data The goal of this work is to derive methods to improve the accuracy of fluorescence-intensity and fluorescence-lifetime measurements of compounds of interest (called analytes, or, equivalently, labels) in the presence of unwanted background fluorescence. Among the fields in which these methods can be applied is drug discovery, particularly in high-throughput screening assays.

Our previous FLDI methods were based on measuring fluorescent systems, containing fluorescence both from analyte, A, and background, B. An expression for the fraction $f_A$ of the fluorescence intensity contributed by A was obtained as a series expansion in $\omega\tau_B$, where this product was <1. This expansion contained only even powers of the product. Truncating before the second-order term thus gave an expression that was good to first order in $\omega\tau_B$. A benefit of this method is that there is no need to determine the value of $\tau_B$.

The present invention truncates the expansion before the fourth-order term and thus is good to third order in $\omega\tau_B$. This improves the ability of the method to determine analyte intensity in the presence of background fluorescence. In contrast to previous work, however, $\tau_B$ now appears in the formulas and must be measured explicitly or implicitly.

This can be done by making measurements at two modulation frequencies, $\omega_1$ and $\omega_2$. The series expansion can then be used to generate two equations (on for each frequency) in two unknowns ($f_A$ and $\tau_B$). Elimination of the lifetime yields an equation for $f_A$.

Here are the details. The earlier series expansion can be written in the form:

$$f_A = \alpha(\omega) + \beta(\omega)\tau_B^2 \tag{60}$$

Here $\alpha(\omega)$ and $\beta(\omega)$ are the following expressions, where dependence on $\omega$ is written explicitly:

$$\alpha(\omega) = [1-X_S(\omega)]/[1-X_A(\omega)] \tag{61}$$

$$\beta(\omega) = \omega^2[X_A(\omega)-X_S(\omega)]/[1-X_A(\omega)]^2 \tag{62}$$

Eliminating $\tau_B^2$ yields the expression:

$$f_A = [\alpha(\omega_1)\beta(\omega_2) - \alpha(\omega_2)\beta(\omega_1)]/[\beta(\omega_2)-\beta(\omega_1)] \tag{63}$$

This form of the equation requires measurement of the analyte fluorescence in the absence of background, which is generally not difficult and, moreover, can be done once and stored for reference and inclusion in the analysis of many samples.

Despite being based on a truncated power series in $\tau_B^2$, this result gives accuracy comparable to that obtained with much more complicated expressions derived from exact equations for the behavior of two-component systems.

E. Reference Compounds

The apparatus, methods, and compositions of matter provided by the invention also can be used to correct for modifications in analyte signal from scattering, absorption, and other modulators, including background, through use of a reference compound. These modifications may affect intensity and polarization, among others.

The compositions of matter provided by the invention may include first and second luminophores having emission spectra that overlap significantly, but luminescence emissions that may be resolved using lifetime-resolved methods. The first and second luminophores may include an analyte and a reference compound. The analyte may be designed to participate in an assay, and the reference compound may be designed to participate in an assay, and the reference compound may be designed to be inert and constant from assay to assay.

The apparatus provided by the invention may include a stage, light source, detector, processor, and first and second optical relay structures. These components are substantially as described above, especially in supporting and inducing an emission from a composition, and in detecting and converting the emission to a signal. The emission may include fluorescence or phosphorescence.

The processor may use information in the signal to determine the intensity of the light emitted by the analyte and the intensity of the light emitted by the reference compound. The analyte and reference compound have luminescence lifetimes that are resolvable by lifetime-resolved methods, so that the intensities of the analyte and reference compound may be determined using lifetime-resolved methods. These methods may include frequency-domain methods, such as those described above for distinguishing analyte and background.

In the presence of a signal modulator, such as scattering or absorption, the apparent intensity $I_c'$ of light detected from a composition will equal the product of a transmission factor T and the true intensity $I_c$ of the light emitted from the composition.

$$I_c' = T \cdot I_c \tag{64}$$

The transmission factor may include contributions from changes in the excitation light and changes in the emission light. The transmission factor typically (but not always) will range from zero to one.

If the composition contains both an analyte and a reference compound, the apparent intensity of the composition will equal the product of the transmission factor and the sum of the true intensity $I_A$ of the analyte and the true intensity $I_R$ of the reference compound.

$$I_c' = T \cdot (I_a + I_r) \tag{65}$$

The apparent intensity $I_a'$ of the analyte will equal the apparent intensity of the composition minus the apparent intensity of the reference compound. Similarly, the apparent intensity $I_r'$ of the reference compound will equal the apparent intensity of the composition minus the apparent intensity of the analyte.

These intensities may be computed using LDI or LRI methods, among others. For example, a typical experiment may include a short-lifetime analyte and a long-lifetime reference compound, although other combinations also may be used. In this case, the apparent intensity of the analyte may be calculated using Equation 22, where the reference compound effectively is treated as long-lifetime background.

$$I_a' = T \cdot I_a = T \cdot (I_c - I_r) = I_c' \cdot \left(1 - \frac{1 - X_c}{1 - X_r}\right) \tag{66}$$

Similarly, the apparent intensity of the reference compound may be calculated using Equation 21, where the analyte effectively is treated as short-lifetime background.

$$I_r' = T \cdot I_r = T \cdot (I_c - I_a) = I_c' \cdot \frac{1 - X_c}{1 - X_r} \tag{67}$$

The processor also uses information in the signal to calculate a quantity that expresses the intensity of the analyte as a function of the intensity of the reference compound. This quantity may be a ratio of the intensity of the analyte to the intensity of the reference compound, among others.

$$\frac{I_a}{I_r} = \frac{I_a'}{I_r'} = \frac{X_c - X_r}{1 - X_c} \tag{68}$$

Such a ratio is independent of the degree of modulation in the sample, and thus will be comparable for every sample in a family of samples, if for example every sample has the same concentration of reference compound.

The processor also is capable of discriminating between the light emitted by the analyte, the light emitted by a reference compound, and a background, if all three have different lifetimes, using the dual-frequency lifetime-resolved methods described above (e.g., Equation 25).

The methods provided by the invention may include various steps, including (1) providing a composition that includes the analyte and a reference compound, (2) illuminating the composition, so that light is emitted by the analyte and reference compound, (3) detecting the light emitted by the analyte and reference compound and converting it to a signal, (4) processing the signal to determine the intensity of the light emitted by the analyte and the intensity of the light emitted by the reference compound, and (5) calculating a quantity that expresses the intensity of the analyte as a function of the intensity of the light emitted by the reference compound. The methods also may include additional or alternative steps. The methods may be practiced using the apparatus described above.

The invention may handle a variety of analytes, reference compounds, and backgrounds. Generally, the excitation and emission spectra of the reference compound should be the same as the excitation and emission spectra of the analyte, so that the intensity of the reference compound will be modulated by the same amount as the intensity of the analyte. (Because the factors that modulate detection of luminescence are generally wavelength dependent, reference compounds having different spectra than the analyte provide only a partial solution, at best.) For optimal resolution, the lifetime of the reference compound should be significantly larger or significantly smaller than the lifetime of the analyte, and the lifetimes of the reference compound and analyte should be greater than the lifetime of the background. Also for optimal resolution, the specific lifetime of the background should be confined to a range. These conditions apply for most assays of commercial interest; for example, in most high-throughput assays, the background from the microplate and assay components is under 10 nanoseconds. These are preferred conditions; because the lifetime-resolved methods described above are so sensitive, the composition actually need include only a small amount of the reference compound (roughly 2% of the total intensity), and the lifetimes of analyte, reference compound, and background can be reasonably similar.

The reference compound may be associated with the composition using a variety of mechanisms. The reference compound may be associated with the composition directly, for example, by dissolving or suspending (e.g., as a micelle) the reference compound in the composition. The reference compound also may be associated with the composition indirectly, for example, by incorporating the reference compound into or onto beads, other carriers, or sample containers associated with the composition.

Associating the reference compound with beads or other carriers has a number of advantages. The carriers may be suspended in the composition or allowed to sink to the bottom of the sample container holding the composition. The carriers also may be attached to the walls or bottom of the sample container, for example, by chemical linkages such as biotin-streptavadin. The carriers also may be rendered magnetic, so that they may be pulled to one part of the sample container (e.g., a side or bottom) to permit the composition to be analyzed with and without the reference compound.

Associating the reference compound with the sample container also has a number of advantages. The reference compound may be layered onto the surface of the sample container, or formed into the plastic or other material used to form the sample container. Such approaches eliminate the need to add the reference compound to the composition, and they may prevent the reference compound from interacting with components of the composition and affecting the associated assay.

Although the invention has been disclosed in its preferred forms, the specific embodiments thereof as disclosed and illustrated herein are not to be considered in a limiting sense, because numerous variations are possible. Singular terms used herein do not preclude the use of more than one of the associated element, and embodiments utilizing more than one of a particular element are within the spirit and scope of the invention. Applicants regard the subject matter of their invention to include all novel and nonobvious combinations and subcombinations of the various elements, features, functions, and/or properties disclosed herein. No single feature, function, element or property of the disclosed embodiments is essential. The following claims define certain combinations and subcombinations of features, functions, elements, and/or properties that are regarded as novel and nonobvious. Other combinations and subcombinations may be claimed through amendment of the present claims or presentation of new claims in this or a related application. Such claims, whether they are broader, narrower, equal, or different in scope to the original claims, also are regarded as included within the subject matter of applicants' invention.

We claim:

1. A method of detecting a nucleic acid target, the method comprising:
   locating a sample containing nucleic acid material at an examination site between sample boundary interfaces located at different points along a Z-axis,
   illuminating the sample with polarized light,
   detecting polarized light emitted substantially exclusively from a sensed volume in the sample, the sensed volume being spaced substantially away from both of the sample boundary interfaces, and
   determining the presence or absence of nucleic acid target in the sample as a function of the extent of polarization of the light emitted from the sample.

2. The method of claim 1, wherein the illuminating step includes the step of directing light from a high color temperature continuous light source toward the sample.

3. The method of claim 1 further comprising:
   automatically adjusting the position of the sensed volume along the Z-axis to maximize signal-to-noise.

4. The method of claim 1 further comprising:
   adjusting the position of the sensed volume along the Z-axis so that the sensed volume is substantially centered within the sample.

5. The method of claim 1, wherein the locating step includes the step of containing the nucleic acid material in a microplate well among a plurality of wells.

6. The method of claim 1, wherein the illuminating step includes the step of directing light through a confocal optical relay structure.

7. A method of detecting a nucleic acid target, the method comprising:
   locating a sample containing nucleic acid material at an examination site between sample boundary interfaces at least partially defined by the walls of a sample well,
   illuminating the sample with polarized light,
   detecting polarized light emitted substantially exclusively from a sensed volume in the sample, the sensed volume being spaced substantially away from the sample boundary interfaces, and
   determining the presence or absence of nucleic acid target in the sample as a function of the extent of polarization of the light emitted from the sample.

8. The method of claim 7, wherein the illuminating step includes the step of directing light through a confocal optical relay structure.

9. The method of claim 7, wherein the illuminating step includes the step of directing light from a high color temperature continuous light source toward the sample.

10. The method of claim 7, wherein the locating step includes the step of containing a nucleic acid material in a microplate well among a plurality of wells organized in a density of at least about 4 wells per 81 mm$^2$.

11. The method of claim 7, wherein the detecting step includes the step of sensing polarized light emitted substantially exclusively from an hourglass-shaped sensed volume in the sample.

12. The method of claim 7, wherein the detecting step includes the step of sensing polarized light emitted substantially exclusively from a sensed volume located substantially in the middle of the sample.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 51 base pairs
      (B) TYPE: nucleic acid
      (C) STRANDEDNESS: single strand
      (D) TOPOLOGY: linear (ii) MOLECULE TYPE: synthetic DNA (vi) ORIGINAL SOURCE:
      (A) ORGANISM: Homo sapiens (ix) FEATURE:
      (A) NAME/KEY:
      (B) LOCATION:1..51

(xi) SEQUENCE DESCRIPTION: SEQ ID NO: 1:

GCTGGGCGCG GACATGGAGG ACGTGNGCGG CCGCCTGGTG CAGTACCGCG G      51

(2) INFORMATION FOR SEQ ID NO: 2:

(i) SEQUENCE CHARACTERISTICS:
      (A) LENGTH: 25 bases
      (B) TYPE: nucleic acid
      (C) STRANDEDNESS: single
      (D) TOPOLOGY: linear (ii) MOLECULE TYPE: synthetic DNA -continued (xi) SEQUENCE DESCRIPTION: SEQ ID NO: 2:

CCGCGGTACT GCACCAGGCG GCCGC                                    25